United States Patent [19]

Horning et al.

[11] 4,171,438

[45] Oct. 16, 1979

[54] 0-2-ISOCEPHEM-4-CARBOXYLIC ACID DERIVATIVES AS ANTIBACTERIAL AGENTS

[75] Inventors: Donald E. Horning, Belleville; Leeson R. Morris, Calgary; James L. Douglas, Montreal, all of Canada

[73] Assignee: Bristol-Myers Company, New York, N.Y.

[21] Appl. No.: 928,499

[22] Filed: Jul. 27, 1978

Related U.S. Application Data

[62] Division of Ser. No. 763,454, Jan. 27, 1977, Pat. No. 4,118,566, which is a division of Ser. No. 598,461, Jul. 23, 1975, Pat. No. 4,013,648.

[51] Int. Cl.$^2$ .......................................... C07D 265/34
[52] U.S. Cl. .................................................. 544/105
[58] Field of Search ................................. 544/105, 90

[56] References Cited

U.S. PATENT DOCUMENTS

| | | | |
|---|---|---|---|
| 4,011,216 | 3/1977 | Menard et al. | 544/105 |
| 4,012,383 | 3/1977 | Belleau et al. | 544/105 |
| 4,065,622 | 12/1977 | Horning et al. | 544/105 |
| 4,065,623 | 12/1977 | Belleau et al. | 544/105 |
| 4,066,832 | 1/1978 | Menard et al. | 544/105 |
| 4,068,066 | 1/1978 | Horning et al. | 544/105 |
| 4,068,075 | 1/1978 | Menard et al. | 544/105 |
| 4,068,078 | 1/1978 | Menard et al. | 544/105 |
| 4,068,080 | 1/1978 | Menard et al. | 544/105 |
| 4,118,566 | 10/1978 | Horning et al. | 544/105 |

FOREIGN PATENT DOCUMENTS 2355209  5/1974  Fed. Rep. of Germany ............. 544/90

OTHER PUBLICATIONS

Cama et al., J. Am. Chem. Soc., vol. 96, pp. 7582-7584 (1974).
Firestone et al., J. Med. Chem., vol. 20, pp. 551 to 556 (1977).
Brunwin et al., J. Chem. Soc. (c), pp. 3756-3762 (1971).
Brunwin et al., J. Chem. Soc., Perkins I, pp. 1321-1328 (1973).

Primary Examiner—John D. Randolph
Attorney, Agent, or Firm—David M. Morse

[57] ABSTRACT

There is described the stereoselective total synthesis of novel $\Delta^{2,3}$-1,4-morpholine-2-carboxylic acids possessing a fused $\beta$-lactam ring in the 1,6-position and carrying a substituent cis to carbon 5 in the 7-position of the fused ring system represented by the general formula

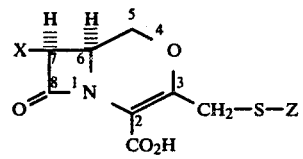

wherein X is acylamino and Z represents optionally substituted $C_1$-$C_6$ alkyl, aryl or aralkyl. Also included in the invention are compounds of the above formula in which the carboxyl group at the 2-position is protected as by an easily cleavable ester group and salts of both the free acids and carboxyl-protected compounds. The compounds are potent antibacterial agents.

15 Claims, No Drawings

0-2-ISOCEPHEM-4-CARBOXYLIC ACID DERIVATIVES AS ANTIBACTERIAL AGENTS

CROSS-REFERENCE TO RELATED APPLICATIONS

This is a divisional application of co-pending application U.S. Ser. No. 763,454 filed Jan. 27, 1977, now U.S. Pat. No. 4,118,566, which in turn is a divisional application of U.S. Ser. No. 598,461 filed July 23, 1975 now U.S. Pat. No. 4,013,648.

BACKGROUND OF THE INVENTION (1) Field of the Invention

The chemical processes of the present invention produce novel antibacterial agents of the β-lactam type containing a hitherto unknown nucleus and useful intermediates for their synthesis.

(2) Description of the Prior Art

Penicillins and cephalosporins comprise a group of well-known antibacterial agents commonly grouped together as a class called β-lactam antibiotics. For a recent review of this field with many citations (especially the first ten) to the prior work, see J. P. Hou and J. W. Poole, β-lactam Antibiotics: Their Physicochemical Properties and Biological Activities in Relation to Structure, J. Pharmaceutical Sciences, 60(4), 503–532 (April, 1971). Most of the work in this field has fundamentally been done, speaking broadly, with 6-aminopenicillanic acid, 7-aminocephalosporanic acid and derivatives thereof produced by fermentation or chemical transformation of the natural products. Despite the extensive progress made in preparing active derivatives of 6-aminopenicillanic acid and 7-aminocephalosporanic acid, there is a continuing search for synthetic and semi-synthetic routes to new families of β-lactam antibiotics which may possess more advantageous properties then those derived from the known pencillin and cephalosporin nuclei.

Considerable work has been done on total chemical synthesis of both known β-lactams and nuclear analogs of such known compounds. A recent review is the text by M. S. Manhas and A. K. Bose, Synthesis of Penicillin, Cephalosporin C and Analogues, Marcel Decker, Inc., 95 Madison Avenue, New York, New York, 1969. Another extensive review is by R. B. Morin and B. G. Jackson, Chemistry of Cephalosporin Antibiotics, Fortschr. Chem. Org. Naturst., 28, 343–403 (1970), especially pages 379–393; the now famous "Woodward Intermediate" is shown therein as compound 146 on page 387. A more recent review of β-lactams is that by M. S. Manhas and A. K. Bose, Beta-Lactams: Natural and Synthetic: Part 1, Wiley-Interscience, New York, New York, 1971. A still further review article on the synthesis of β-lactams is that by A. K. Mukerjee et al., Synthesis, 327 (1973).

Other pertinent publications relating to synthesis of β-lactams are:

(a) D. M. Brunwin, G. Lowe and J. Parker, J.C.S. Chem. Comm., 1971, 865–867, describing synthesis of nuclear analogs of the penicillin-cephalosporin group.

(b) D. M. Brunwin et al., J. Chem. Soc. (C), 1971, 3756–3762 and J.C.S. Chem. Comm., 1972, 589–590 describing total synthesis of nuclear analogs of penicillins and cephalosporins.

(c) S. Kukolja, J. Amer. Chem. Soc., 93, 6267–6270 (1971) and 94, 7590–7593 (1972) describing preparation of 6-phthalimido-5-epipenicillanates and disulfide analogs of penicillins.

(d) J. S. Webber et al., J. Medicinal Chemistry, 14(11), 1136–1138 (1971) describing preparation of 3-cyanomethyl cephem nucleus.

(e) West German Patent Specification 2,219,601 (Farmdoc 76,051T) describing synthesis of β-lactams of the formula

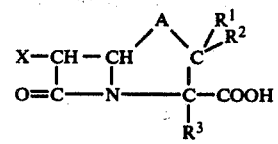

wherein X is halo, $N_3-$ or $H_2N-$, A is $-S-$, $-S-CH_2-$, $-O-$, $-O-CH_2-$, $-CH_2$, $-CH_2CH_2-$ or $-NH-$ and $R^1$, $R^2$ and $R^3$ are hydrogen, $C_1-C_6$ alkyl or aryl.

(f) U.K. Pat. No. 1,308,822 disclosing β-lactams of the formula

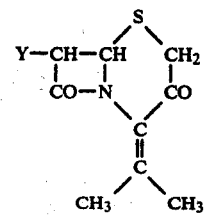

where Y=amino or substituted amino.

(g) S. Wolft et al., Can. J. Chem., 50, 2894–2905 (1972) describing synthesis of sulfur-free penicillin derivatives.

(h) French Pat. No. 2,111,859 describing nuclei of the formula

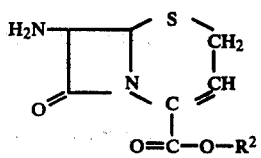

and 7-acylated derivatives thereof.

(i) Helvetica Chimica Acta, 55(2), 388–429 (1972) describing nuclear modified cephalosporins and penicillins.

(j) F. Moll et al., Zeit. fur Naturforsch. B, 27(b)6, 727 (1972) describing nuclear analogs of cephalosporins.

(k) U.K. Specifications 1,271,013 and 1,271,014 describing γ-lactams of 7-(acylamino)-3-aminomethyl-ceph-3-em-4-carboxylic acids.

(l) U.K. Pat. Specification No. 1,271,180 describing preparation of novel thiazoline azetidinone rearrangement products useful as intermediates in penicillin and cephalosporin synthesis.

(m) German Pat. Specification Nos. 2,046,822, 2,046,823 and 2,046,824 describing synthesis of novel azetidinone intermediates.

(n) G. Lowe et al., J. Chem. Soc. Perkins I, 1322 (1973) describing total synthesis of nuclear analogs of 7-methylcephalosporins having the formula

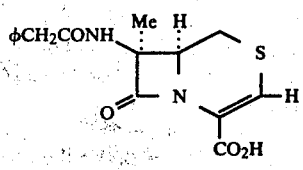

(o) D. M. Brunwin et al., J. Chem. Soc. Chem. Comm., 865 (1971) describing synthesis of compounds of the formula

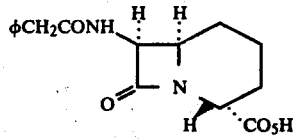

(p) S. Wolfe et al., Canadian J. Chem., 50, 2902 (1972) describing compounds of the formula

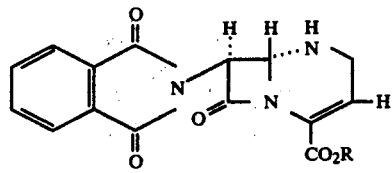

(q) J. P. Luttringer et al., Tetrahedron Letters, 4163–4166 (1973) describing compounds of the formula

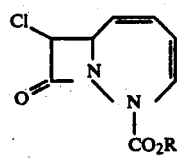

(r) U.S. Pat. No. 3,835,130 disclosing β-lactams of the formula

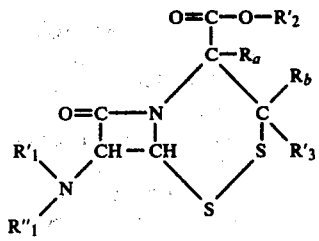

wherein $R_a$ and $R_b$ are each hydrogen or $R_a$ and $R_b$ form a covalent carbon-to-carbon bond, $R_1'$ represents hydrogen, $R_1''$ is cyanoacetyl, bromacetyl or an acyl group of the formula

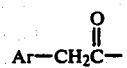

in which Ar is phenyl, 3-hydroxyphenyl, 4-hydroxyphenyl, 3-chloro-4-hydroxyphenyl, 3,5-dichloro-4-hydroxyphenyl or 2-thienyl, $R_2'$ is hydrogen and $R_3'$ is hydrogen or lower alkyl.

(s) West German Offenlegungsschrift 2,355,209 describing synthesis of β-lactams of the formula

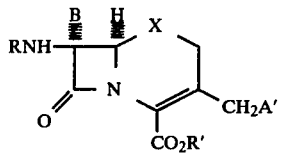

wherein R is acyl, A' is hydrogen, hydroxy, carbamoyloxy, thiocarbamoyloxy, quaternary ammonium, N-lower alkyl carbamoyloxy, N,N-di-lower alkyl carbamoyloxy, N-lower alkylthio and N,N-diloweralkylthiocarbamoyloxy, azido, halo, cyano, a tertiary amine, acyloxy, or a 5-member heterocyclic thio group having 1–4 hetero atoms; B is H, $OCH_3$ or SR where R is lower alkyl or aryl; X is a divalent radical selected from —O—, —$CH_2$— or —NY— where Y is hydrogen, lower alkyl, formyl or benzyl and R' is hydrogen or a protecting group.

Replacement of the 3-acetoxy group of a cephalosporin by various heterocyclic thiols has been extensively discussed in the literature. Issued patents on 3-thiolated cephalosporins in which the 7-substituent is (1) α-Amino-α-phenylacetamido include U.S. Pat. Nos. 3,641,021, 3,734,907, 3,687,948, 3,741,965, 3,757,015, 3,743,644, Japan 71/24400 (Farmdoc 46374S), Belgium 776,222 (Farmdoc 38983T; U.K. 1,328,340 which includes various substituents on the benzene ring), Bengium 772,592 (Farmdoc 19696T; U.S. Pat. Nos. 3,687,948, 3,734,907 and 3,757,012), West Germany 2,202,274 (Farmdoc 50428T) corresponding to U.S. Pat. No. 3,759,904, Netherlands 7205644 (Farmdoc 76309T; U.S. Pat. No. 3,757,014); U.S. Pat. Nos. 3,855,213 and 3,867,380; and (2) o-, m- or p-aminoethoxyphenylacetamido as Netherlands 72/13968 (Farmdoc 24740U) corresponding to U.S. Pat. No. 3,759,905 and (3) o-aminomethylphenylacetamido as Netherlands 72/06326 (Farmdoc 76374T) (which also reviews the older patent literature concerning substituted 7-phenylacetamidocephalosporanic acids) corresponding to U.S. Pat. No. 3,766,176 and 3,766,175; and (4) N-(phenylacetimidoyl)aminoacetamido as U.S. Pat. No. 3,692,779; and (5) α-amino-α-(1,4-cyclohexadienyl)acetamido as in Bengium 776,222 (Farmdoc 38983T; U.K. 1,328,340).

Additional similar disclosures are found in U.S. Pat. No. 3,692,779 (Belgium 771,189; Farmdoc 12819T), Japan 72/05550 (Farmdoc 12921T), Japan 72/05551 (Farmdoc 12922T), U.S. Pat. No. 3,719,673 (Belgium 759,570; Farmdoc 39819S), Belgium 793,311 (Farmdoc 39702U) and Belgium 793,191 (Farmdoc 39684U).

Issued disclosures of 3-thiolated cephalosporins in which the 7-substituent is 7-mandelamido (7-α-hydroxyphenylacetamido) are found, for example, in U.S. Pat. No. 3,641,021, France 73.10112, U.S. Pat. No. 3,796,801, Great Britain 1,328,340 (Farmdoc 38983T), U.S. Pat. No. 3,701,775, Japan 4844293 (Farmdoc 55334U), U.S. Pat. No. 3,855,213, and in Hoover et al., J. Med. Chem. 17(1), 34–41 (1974) and Wick et al., Antimicrobial Ag. Chemo., 1(3), 221–234 (1972).

U.S. Pat. No. 3,819,623 (and, for example, also U.K. Pat. No. 1,295,841 and West Germany 1,953,861) discloses specifically and with working details the preparation of 2-mercapto-1,3,4-thiadiazole-5-acetic acid and its conversion to 7-(1H-tetrazol-1-yl-acetamido)-3-(5-carboxymethyl-1,3,4-thiadiazol-2-ylthiomethyl)-3-cephem-4-carboxylic acid which is also disclosed in West German Offenlegungsschrift 2,262,262.

SUMMARY OF THE INVENTION

The present invention provides steroselective total synthesis of certain novel substituted $\Delta^{2,3}-1,4$-morpholine-2-carboxylic acids possessing a fused $\beta$-lactam ring in the 1,6-position and carrying a substituent cis to carbon 5 in the 7-position of the fused ring system represented by the general formula

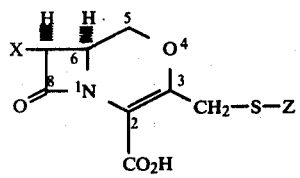

wherein X is amino, azido or acylamido and Z represents optionally substituted $C_1$-$C_6$ alkyl, aryl, aralkyl or heterocyclic. When X is acylamino, these acids (and their pharmaceutically acceptable salts and physiologically hydrolyzed esters) are potent antibacterial agents.

Also included in this invention are various novel intermediates useful in preparing the active $\beta$-lactam derivatives described above and various processes for the production of the intermediates and active compounds.

The compounds having the above general formula represent a new family of $\beta$-lactam antibiotics. They can be considered nuclear analogs of cephalosporins in which the sulphur atom of the dihydrothiazine ring is replaced by an oxygen atom and shifted from position 5 to position 4 of the $\beta$-lactam ring system as numbered in the formula above. The nomenclature to be used could be the following:

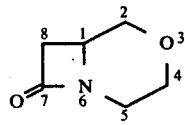

3-oxa-6-aza-bicyclo-[4,2,0]octan-7-one.

However, Sheehan has used the term O-cepham for the structure

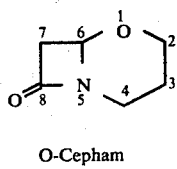

O-Cepham

[J. C. Sheehan and M. Dadic, J. Heterocyclic Chem,. 5, 770 (1968] and we propose the use of the term 0-2-isocephem for the basic system having the formula

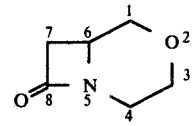

The numerical prefix indicates the position of the hetero-atom.

To illustrate the above system, the intermediate of the formula

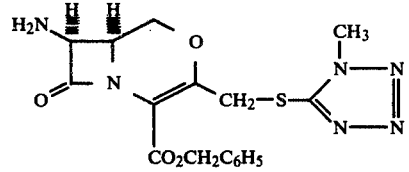

may be named benzy 7$\beta$-amino-3-(1-methyltetrazol-5-ylthiomethyl) -$\Delta^3$-0-2-isocephem-4-carboxylate and the compound of the formula

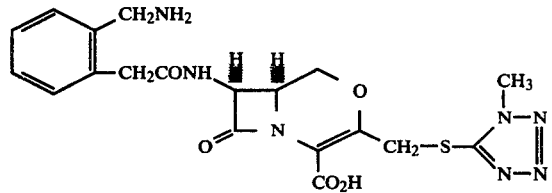

may be named 7$\beta$-(2-aminomethylphenylacetamido)-3-(1-methyltetrazol-5-ylthiomethyl)-$\Delta^3$-0-2-isocephem-4-carboxylic acid.

There is thus provided by the present invention the novel 0-2-isocephem carboxylic acid compounds having the formula

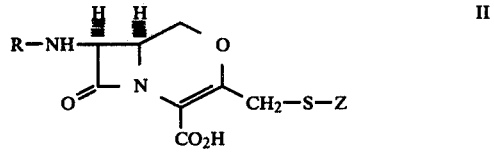

wherein R is an acyl group and Z represents optionally substituted $C_1$-$C_6$ alkyl, aryl, aralkyl or heterocyclic, and easily cleavable esters and pharmaceutically acceptable salts of said acids and esters.

The acyl group R can be chosen from a wide variety of organic acyl radicals which yield products of improved properties and is preferably an acyl radical which is contained in a naturally occurring or biosynthetically, semi-synthetically or totally-synthetically produced pharmacologically active N-acyl derivative of 6-aminopenicillanic acid or 7-aminocephalosporanic acid. Examples of suitable acyl groups are defined in the following general formulae, but it should be noted that this is not intended to be an exhaustive list of all the possible acyl groups which may be used.

$$R^a C_n H_{2n} CO—$$ (i)

where $R^a$ is aryl (carbocyclic or heterocyclic), substituted aryl, cycloalkyl, substituted cycloalkyl, cycloalkenyl, substituted cycloalkenyl or a nonaromatic or mesoionic heterocyclic group, and n is an integer from 1–4. The preferred $R^a$ substituted are (a) aryl selected from phenyl, 2-thienyl, 3-thienyl, furyl, 4-isoxazolyl, pyridyl, tetrazolyl, sydnone-3 or -4, imidazolyl, naphthoyl, quinoxalinyl, triazolyl, isothiazolyl, thiadiazolyl, thiazolyl, oxazolyl, oxidiazolyl, pyrazolyl, furazan, pyrazinyl, pyrimidinyl, pyridazinyl or triazinyl; (b) substituted aryl in which the aryl groups mentioned above under (a) are substituted by one or more radicals selected from chloro, bromo, iodo, fluoro, nitrol, amino, cyano, (lower)alkanoyloxy, (lower)alkanoyl, (lower)alkoxyamino, (lower)alkoxy, (lower)alkyl, (lower)alkylamino, hydroxy, guanidino, (lower)alkylthio, carboxy, phenyl, halophenyl, trifluoromethyl, di(lower)alkylamino, sulfamyl, (lower)alkanoylamino, phenyl(lower)alkylamido, cycloalkylamino, allylamido morpholinocarbonyl, pyrrolidinocarbonyl, piperidinocarbonyl, tetrahydropyridino, furfurylamido or N-alkyl-N-anilino; (c) $C_3$–$C_{12}$ cycloalkyl; (d) substituted $C_3$–$C_{12}$ cycloalkyl where the substituents are one or more radicals selected from chloro, bromo, fluoro, iodo, nitro, trifluoromethyl, $C_1$–$C_4$ alkyl, $C_1$–$C_4$ alkylamino, $C_1$–$C_2$ alkoxy or amino; (e) $C_3$–$C_{12}$ cycloalkenyl, said cycloalkenyl group having 1 or 2 double bonds; and (f) substituted $C_3$–$C_{12}$ cycloalkenyl, said cycloalkenyl group having 1 or 2 double bonds and being substituted by one or more radicals selected from chloro, bromo, fluoro, iodo, nitro, trifluoromethyl, $C_1$–$C_4$ alkyl, $C_1$–$C_4$ alkylamino, $C_1$–$C_2$ alkoxy or amino. The most preferred $R^a$ groups are phenyl; phenyl substituted by one or more radicals selected from chloro, bromo, iodo, fluoro, nitro, amino, (lower)alkyl, guanidino, (lower)alkylthio, cyano, (lower)alkoxy, sulfamyl, (lower)alkylamino, hydroxy, acetoxy, or trifluoromethyl; 2-thienyl; 3-thienyl; tetrazolyl; sydnone -3; sydnone -4; furyl; isothiazolyl; thiadiazolyl optionally substituted with phenyl; oxadiazolyl optionally substituted with phenyl; thiazolyl; imidazolyl; triazolyl; oxazolyl; pyridyl; furazan optionally substituted at the 3-position with methoxy; 4-isoxazolyl optionally substituted at the 5-position with methyl and at the 3-position with phenyl or halophenyl; 1,4-cyclohexadienyl; 1-cyclohexenyl and 1-aminocyclohexyl.

The most preferred acyl groups of this category are those in which n is 1. Examples of this category include phenylacetyl, halophenylacetyl, nitrophenylacetyl, aminophenylacetyl, β-(o-aminomethylphenyl)propionyl, (lower)alkanoyloxyphenylacetyl (e.g. p-acetoxyphenylacetyl), (lower)alkoxyphenylacetyl (e.g methoxyphenylacetyl, ethoxyphenylacetyl), (lower)alkylphenylacetyl (e.g. methylphenylacetyl or ethylphenylacetyl), hydroxyphenylacetyl (e.g. o-hydroxyphenylacetyl), (lower)alkylaminophenylacetyl (e.g. o-, m- or p-aminomethylphenylacetyl), o- m- or p- guanidinophenylacetyl, o-carboxyphenylacetyl, N,N-bis-(2-chloroethyl)aminophenylpropionyl, thien-2 and 3-ylacetyl, 2- or 3- furylacetyl, 1,2,5-thiadiazole-3-acetyl, isothiazolyl-4-acetyl, 4-isoxazolyacetyl, 1-cyclohexenylacetyl, 2-aminomethyl-1-cyclohexenylacetyl, 1-aminocyclohexylacetyl, 1,4-cyclohexadienylacetyl, 2-aminomethyl-1,4-cyclohexadienylacetyl, pyridylacetyl, tetrazolylacetyl (other heterocyclic groups of this type are disclosed in U.S. Pat. Nos. 3,819,623 and 3,516,997) or a sydnoneacetyl group as disclosed in U.S. Pat. Nos. 3,681,328, 3,530,123 and 3,653,983. Other groups of this type include 3-phenyl-5-chlorophenyl5-methylisoxazol-4-ylacetyl and 3-(2,6-dichlorophenyl)-5-methylisoxazol-4-ylacetyl or a group in which isoxazolyl is replaced by isothiazole as disclosed in U.S. Pat. No. 3,551,440. Still other examples are o-, m- and p- (2'-aminoethoxy)-phenylacetyl (as disclosed in U.S. Pat. No. 3,759,905), 4,5-dimethoxycarbonyl-1,2,3-triazol-1ylacetyl or 4-cyano-1,2,3-triazol-1-yl-acetyl (as disclosed in U.S. Pat. No. 3,821,206) and imidazol-(1)-acetyl (as disclosed in U.S. Pat. No. 3,632,810;

$$C_nH_{2n+1}CO— \quad \text{(ii)}$$

where n is an integer from 1–7. The alkyl group may be straight or branched and, if desired, may be interrupted by an oxygen or sulphur atom or substituted by, e.g., a cyano group. Examples of this group include cyanoacetyl, valeryl, hexanoyl, heptanoyl, ethoxycarbonyl, octanoyl and butylthioacetyl. A preferred acyl group is cyanoacetyl;

$$C_nH_{2n-1}CO— \quad \text{(iii)}$$

where n is an integer from 2–7. The alkenyl group may be straight or branched and, if desired, may be interrupted by an oxygen or sulphur atom. An example of this group is allylthioacetyl;

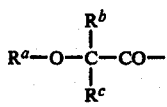

(iv)

where $R^a$ is as defined under (i) and in addition may be benzyl, $C_1$–$C_6$ alkyl or (lower)alkoxycarbonyl and $R^b$ and $R^c$ which may be the same or different each represent hydrogen, phenyl, benzyl, phenethyl or $C_1$–$C_6$ alkyl. The preferred $R^a$ substituents in this category are benzyl, $C_1$–$C_6$ alkyl, (lower)alkoxycarbonyl and those mentioned under (i) as being preferred aryl, substituted aryl, cycloalkyl (and substituted cycloalkyl) and cycloalkenyl (and substituted cycloalkenyl) groups. The most preferred $R^a$ group is phenyl. Examples of this group include phenoxyacetyl, 2-phenoxy-2-phenylacetyl, 2-phenoxypropionyl, 2-phenoxybutyryl, benzyloxyacetyl, 2-methyl-2-phenoxypropionyl, p-cresoxyacetyl, p-methylthiophenoxyacetyl and ethoxycarbonylacetyl;

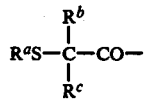

(v)

where $R^a$ is as defined under (i) and in addition may be benzyl or $C_1$–$C_6$ alkyl and $R^b$ and $R^c$ have the meanings defined under (iv). The preferred $R^a$ substituents in this category are benzyl, $C_1$–$C_6$ alkyl and those mentioned under (i) as being preferred aryl, substituted aryl, cycloalkyl (and substituted cycloalkyl) and cycloalkenyl (and substituted cycloalkenyl) groups. The most preferred aryl groups of this type are those in which $R^b$ and $R^c$ are hydrogen and $R^a$ is phenyl; phenyl substituted with one or more radicals selected from chloro, bromo, iodo, fluoro, nitro, amino, (lower)alkyl, (lower)alkylthio, cyano, (lower)alkoxy, (lower)alkylamino, hydroxy, acetoxy or trifluoromethyl; 3-pyridyl; or 4-pyridyl;

$$R^aX(CH_2)_mCO— \quad \text{(vi)}$$

where $R^a$ is as defined under (i) and in addition may be benzyl, X is oxygen or sulphur and m is an integer from 2–5. The preferred $R^a$ groups are benzyl and those mentioned under (i) as being preferred aryl, substituted aryl, cycloalkyl (and substituted cycloalkyl) and cycloalkenyl (and substituted cycloalkenyl) groups. An example of this group is S-benzylthiopropionyl.

$R^aCO—$ (vii)

where $R^a$ is as defined under (i). The preferred $R^a$ groups are those mentioned under (i) as being preferred aryl, substituted aryl, cycloalkyl (and substituted cycloalkyl) and cycloakenyl (and substituted cycloalkenyl) groups. The most preferred aryl groups of this category are those in which $R^a$ is phenyl; phenyl substituted with one or more radicals selected from chloro, bromo, iodo, fluoro, nitro, amino, (lower)alkyl, (lower)alkylthio, cyano, (lower)alkoxy, (lower)alkylamino, di(lower)alkylamino, hydroxy, acetoxy or trifluoromethyl, and most preferably phenyl substituted at the 2-position by carboxy or phenyl or at the 2- and 6-positions by methoxy 2-ethoxynaphthoyl; 3-phenyl-5-methylisoxazol-4-yl; 3-o-chlorophenyl-5-methylisoxazol-4-yl; 3-(2,6-dichlorophenyl)-5-methylisoxazol-4-yl and 1-aminocyclohexyl. Examples of this group include 2,6-dimethoxybenzoyl, benzoyl, 2-biphenylcarbonyl, 2-aminomethylbenzoyl, 2-carboxybenzoyl-2-phenylbenzoyl, 2-thienylcarbonyl, 3-thienylcarbonyl and 2-chlorobenzoyl;

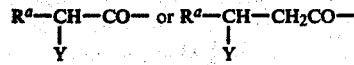  (viii)

where $R^a$ is as defined under (i) and Y is hydrazino, guanidino, ureido, thioureido and substituted thioureido (as disclosed in U.S. Pat. No. 3,741,962), allophanamido (as described in U.S. Pat. No. 3,483,188), 3-guanyl-1-ureido (as in U.S. Pat. No. 3,796,709), 3-(2-furoyl)ureido, cyanamino (as in U.S. Pat. No. 3,796,709), 3-(benzoyl)ureido, azido, amino, acylamino (e.g. carbobenzoxyamino), a group obtained by reacting the amino group of the 7-side chain with an aldehyde or ketone (e.g. acetone, formaldehyde, acetaldehyde, butyraldehyde, acetylacetone, methyl acetoacetate, benzaldehyde, salicylaldehyde, methyl ethyl ketone or ethyl acetoacetate), hydroxy, etherified hydroxy, esterified hydroxy, carboxy, esterified carboxy (as disclosed for example in U.S. Pat. Nos. 3,282,926, 3,819,601 and 3,635,961 and including especially

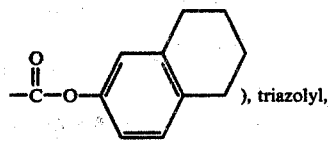), triazolyl, tetrazolyl, cyano, halogeno, acyloxy (e.g. formyloxy or (lower)alkanoyloxy), sulfo, sulfoamino or esterified sulfo. The preferred $R^a$ substituents are thos mentioned under (i) as being preferred aryl, substituted aryl, cycloalkyl (and substituted cycloalkyl) and cycloalkenyl (and substituted cycloalkenyl) groups. Preferred Y substituents are hydrazino; guanidino; ureido; substituted thioureido of the formula

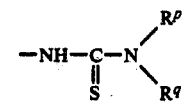

in which $R^p$ is hydrogen or $C_1$–$C_8$ alkyl and $R^q$ is hydrogen, $C_1$–$C_8$ alkyl, $C_2$–$C_8$ alkenyl, phenyl, benzoyl, $C_1$–$C_8$ alkoxy—$C_1$–$C_8$ alkyl, (carbo—$C_1$–$C_8$ alkoxy) $C_1$–$C_8$ alkyl; allophanamido; 3-guanyl-1-ureido; 3-(2-furoyl)ureido; 3-(benzoyl)ureido; azido; amino; a group obtained by reacting the amino group Y with acetone, formaldehyde, acetaldehyde, butyraldehyde, acetylacetone, methyl acetoacetate, benzaldehyde, salicylaldehyde, methyl ethyl ketone or ethyl acetoacetate; hydroxy; etherified hydroxy including especialluy (lower)alkoxy; carboxy; esterified carboxy including especially 5-indanyloxycarbonyl; triazolyl; tetrazolyl; cyano; cyanamino; halogeno; formyloxy; (lower)alkanoyloxy; sulfo; or sulfoamino. Examples of this group include α-aminophenylacetyl; α-carboxyphenylacetyl; 2,2-dimethyl-5-oxo4-phenyl-1-imidazolyl; α-amino-p-hydroxyphenylacetyl; α-hydroxyphenylacetyl; α-formyloxyphenylacetyl and other aryl groups of this type disclosed in U.S. Pat. Nos. 3,812,116 and 3,821,017; α-amino-α-2- or 3-thienylacetyl; α-amino-α-(3-chloro-4-hydroxy)phenylacetyl; α-amino-α-(1,4-cyclohexadienyl)acetyl; α-azidophenylacetyl; α-amino-α-(1-cyclohexenyl)acetyl; 2-carboxy-α-3-thienylacetyl; α-amino-α-(3,5-dichloro-4-hydroxyphenyl)acetyl; α-amino-α-3- or 4- or 5-isothiazolylacetyl (as in U.S. Pat. No. 3,579,506) and other α-amino and α-hydroxyheterocyclylacetyl groups as disclosed for example in U.S. Pat. No. 3,821,207;

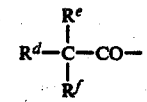 (ix)

where $R^d$, $R^e$ and $R^f$ which may be the same or different may each represent $C_1$–$C_6$ alkyl, phenyl or substituted phenyl. The preferred phenyl substituents are one or more radicals selected from chloro, bromo, iodo, fluoro, trifluoromethyl, nitro, amino, cyano, (lower)alkanoyloxy, (lower)alkanoyl, (lower)alkoxyamino, (lower)alkoxy, (lower)alkyl, (lower)alkylamino, hydroxy, (lower)alkylthio, carboxy, di(lower)alkylamino or sulfamyl. An example of this group is triphenylmethylcarbonyl.

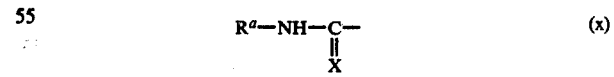 (x)

where $R^a$ is as defined under (i) and in addition may be hydrogen, $C_1$–$C_6$ alkyl, halogen substituted $C_1$–$C_6$ alkyl, phenethyl, phenoxymethyl; benzyl or

and X is oxygen or sulphur. An example of such a group is $Cl(CH_2)_2NHCO$;

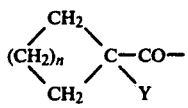 (xi)

where Y is as defined under (viii) and n is an integer of 1–4. A most preferred Y substituent is amino. An example of this group is 1-aminocyclohexanecarbonyl.

(xii) Aminoacyl, for example

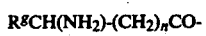

where n is an integer of 1–10, or

where m is zero or an integer from 1–10, and n is 0, 1, or 2; $R^g$ is hydrogen or an alkyl, aryl, aralkyl or carboxy group or a group as defined under $R^a$ in (i) above; and Ar is an arylene group, e.g. p-phenylene or 1,4-naphthylene. Preferred aryl groups of the above formulae are those in which $R^g$ is hydrogen, (lower)-alkyl, phenyl, benzyl or carboxy and Ar is p-phenylene or 1,4-naphthylene. Examples of such groups are disclosed in U.K. Pat. No. 1,054,806. Examples of groups of this type include p-aminophenylacetyl and δ-aminoadipoyl derived from naturally occurring amino acids and derivatives thereof, e.g. N-benzoyl-δ-aminodipoyl;

(xiii) Substituted glyoxylyl groups of the formula

where $R^h$ is an aliphatic, araliphatic or aromatic group. The preferred $R^h$ groups are 2-thienyl; 3-thienyl; α-naphthyl; 2-phenanthryl or a mono-, di- or trisubstituted phenyl group, the substituents being selected from chloro, bromo, iodo, fluoro, amino, di(lower)alkylamino, (lower)alkyl, (lower)alkoxy, nitro or (lower)alkanoylamino. Examples of this category are disclosed in U.S. Pat. Nos. 3,546,219 and 3,573,294. Included in this group are also the α-carbonyl derivatives of the above substituted glyoxylyl groups formed for example with hydroxylamine, semicarbazide, thiosemicarbazide, isoniazide or hydrazine;

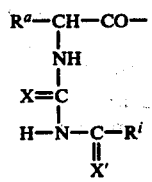 (xiv)

where $R^a$ has the meaning defined under (i), X is oxygen or sulphur, X' is oxygen or imino and $R^i$ represents (lower)alkyl, cycloalkyl having 4, 5, 6 or 7 carbon atoms, monohalo(lower)alkyl, dichloromethyl, trichloromethyl, (lower)alkenyl of 2–6 carbon atoms,

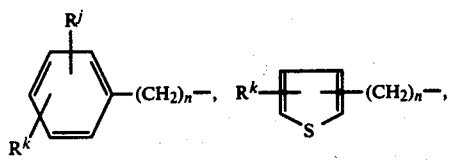

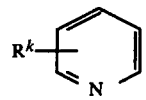

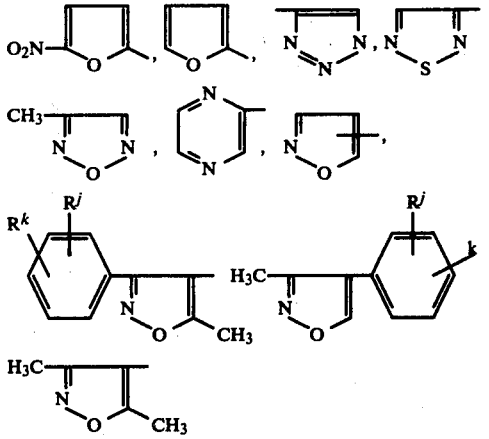

n is an integer from 0 to 3 inclusive and each of $R^k$ and $R^j$ is hydrogen, nitro, di(lower)alkylamino, (lower)-alkanoylamino, (lower)alkanoyloxy, $C_1$–$C_6$ alkyl, $C_1$–$C_6$ alkoxy, sulfamyl, chloro, bromo, iodo, fluoro or trifluoromethyl. The preferred $R^a$ substituents are those mentioned under (i) as being preferred aryl, substituted aryl, cycloalkyl (and substituted cycloalkyl) and cycloalkenyl (and subsituted cycloalkenyl) groups. Preferred acyl groups of this type are those in which $R^a$ is 2-thienyl; 3-thienyl; phenyl; or phenyl substituted by one or more radicals selected from nitro, di(lower)alkylamino, (lower)alkanoylamino, amino, hydroxy, (lower)alkanoyloxy, $C_1$–$C_6$ alkyl, $C_1$–$C_6$ alkoxy, sulfamyl, chloro, bromo, iodo, fluoro or trifluoromethyl; X is oxygen; X' is oxygen or imino and $R^i$ is (lower)alkyl, phenyl, 2-thienyl, 3-thienyl, 2-furyl or 5-nitro-2-furyl. The most preferred groups are those of the above formula where $R^a$ phenyl, p-hydroxyphenyl, 2-thienyl or 3-thienyl; X is oxygen; X' is oxygen, and $R^i$ is phenyl or 2-furyl. Examples are disclosed in U.S. Pat. Nos. 3,687,949 and 3,646,024;

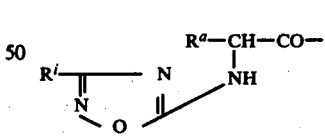 (xv)

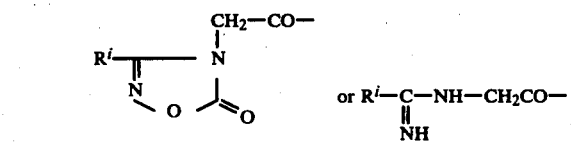

where $R^a$ has the meaning defined in (i) and $R^i$ has the meaning defined in (xiv). The preferred $R^a$ substituents are those mentioned under (i) as being preferred aryl, substituted aryl, cycloalkyl (and substituted cycloalkyl) and cycloalkenyl (and substituted cycloalkenyl) groups. Preferred $R^i$ substituents include (lower)alkyl, dichloromethyl, $C_4$–$C_7$ cycloalkyl, 2-thienyl, 3-thienyl, phenyl, benzyl, halobenzyl,

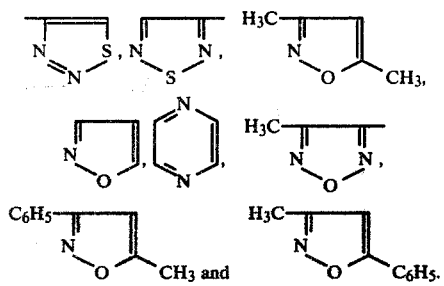

Examples of this group are disclosed in U.S. Pat Nos. 3,626,024 and 3,692,779;

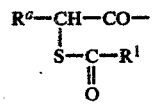 (xvi)

where $R^a$ has the meaning defined in (i) and $R^1$ is (lower)-alkyl, $C_3$–$C_{12}$ cycloalkyl, aryl (especially phenyl), a monocyclic heterocyclic radical having 5 or 6 atoms exclusive of hydrogen which are C, S, N or O, no more than 2 atoms being other than C, or a substituted monocyclic heterocyclic radical as defined above having one or more substituents selected from halo, (lower)alkyl, (lower)alkoxy or phenyl. Examples of this group are disclosed in U.S. Pat. No. 3,778,436. Most preferred $R^1$ groups are (lower)alkyl, phenyl, thienyl or furyl.

A preferred class of acyl groups are those of the formula

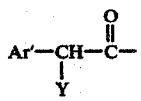

wherein Ar' is a radical of the formula

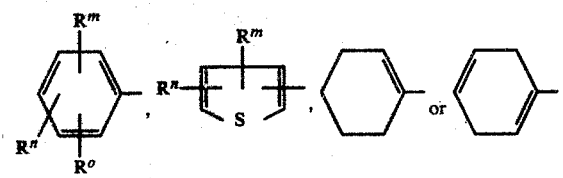

in which $R^m$, $R^n$ and $R^o$ are alike or different and each is hydrogen, hydroxy, (lower)alkyl, cyano, (lower)alkoxy, chloro, bromo, iodo, fluoro, trifluoromethyl, nitro, amino, (lower)alkylamino, di(lower)alkylamino, (lower)-alkanoyl, (lower)alkanoyloxy such as p-acetoxy or phenyl and Y is amino or a group obtained by reacting the amino group with acetaldehyde, formaldehyde or acetone, fluoro, chloro, bromo, iodo, hydroxy, (lower)alkanoyloxy, carboxy, guanidino, 3-guanyl-1-ureido, 3-(2-furoyl)ureido, 3-benzoylureido, sulfo, sulfoamino, ureido, thioureido, (lower)-alkoxy, cyano, cyanamino or indanyloxycarbonyl. Particularly preferred Ar radicals are phenyl, p-hydroxyphenyl, 4-hydroxy-3,5-dichlorophenyl, 3-chloro-4-hydroxyphenyl, o-, m- or p- aminomethylphenyl, 2-thienyl, 3-thienyl, 1-cyclohexenyl and 1,4-cyclohexadienyl. Particularly prefered Y groups are amino, hydroxy and carboxy. Set forth below are formulae of the most preferred acyl groups of this class:

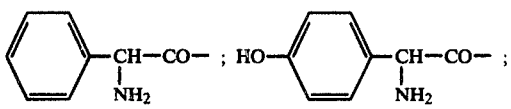

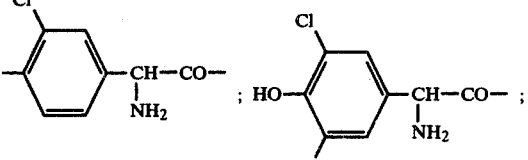

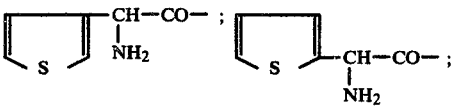

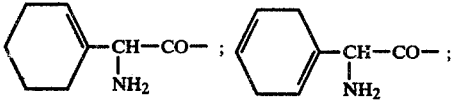

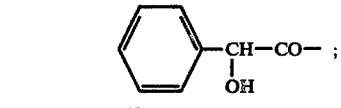

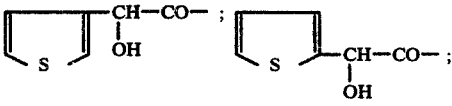

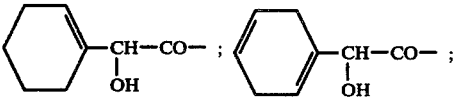

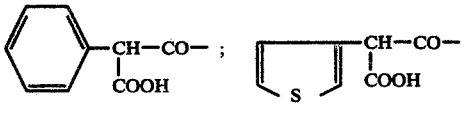

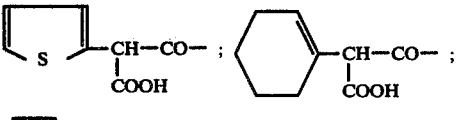

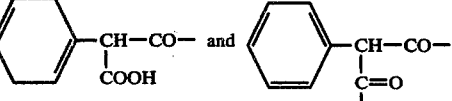

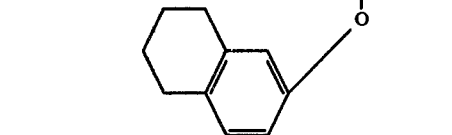

Of most interest are the acyl groups of the above class where the acid ArCH(X)COOH is of the D-series.

Other particularly preferred acyl groups for the compounds of formula I are

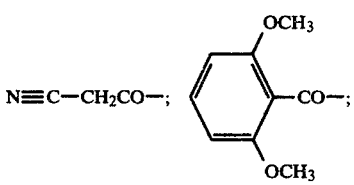

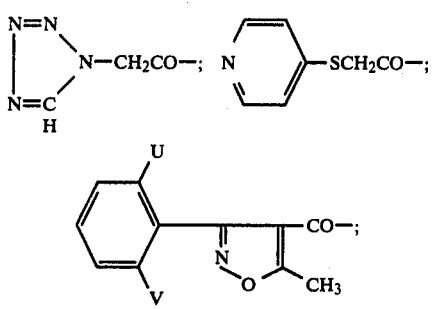

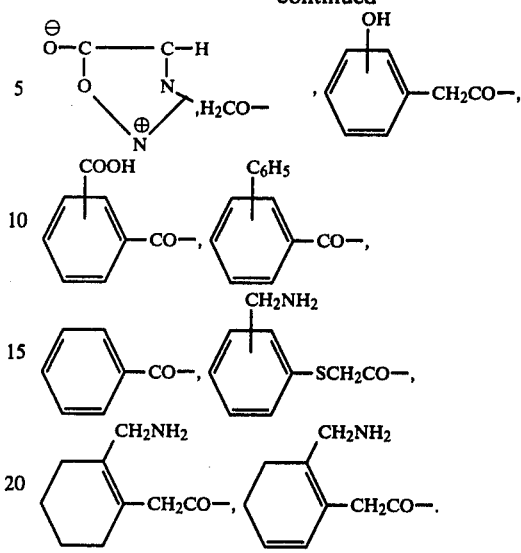

where U and V are alike or different and each is hydrogen, chloro or fluoro;

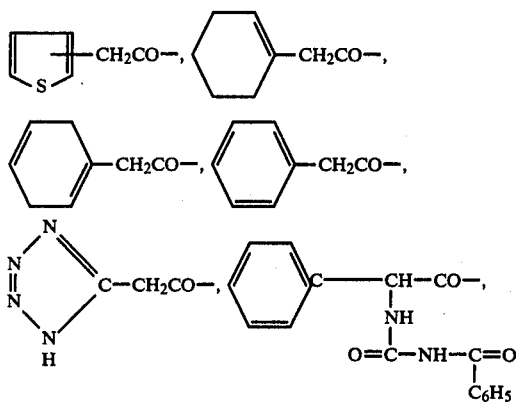

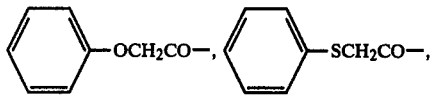

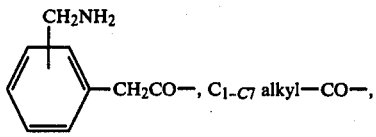

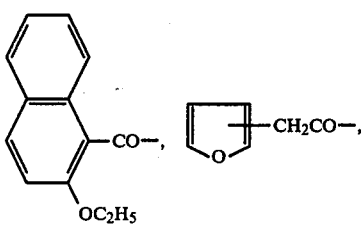

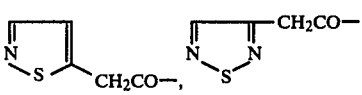

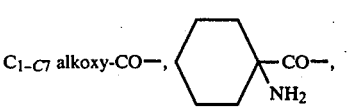

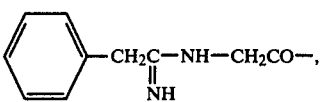

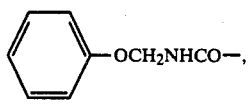

Substitutent Z in formulae I and II above may be $C_1-C_6$ alkyl, aryl, aralkyl or heterocyclic, any of said groups being optionally substituted by one or more substituents. The alkyl group may be a monovalent saturated aliphatic hydrocarbon radical having from 1 to 6 carbon atoms and a straight or branched chain, e.g., methyl, ethyl, propyl, isopropyl, butyl, isobutyl, t-butyl, amyl or hexyl. The aryl group may be a mono-, bi- or polycyclic aromatic hydrocarbon radical, e.g., phenyl, 1-naphthyl, 2-naphthyl or 2-phenanthryl. The term aralkyl as used herein includes monovalent aryl-substituted aliphatic hydrocarbon radicals of the formula aryl-(ALK)$_m$—in which aryl is as defined above, m is an integer of 1 to 4 and ALK represents a straight or branched chain alkylene radical, e.g., —(ALK)$_m$—may be methylene, ethylene, propylene, butylene, 1-methylpropylene, 2-ethylethylene and the like. Heterocyclic Z substituents may be heteromonocyclic or heterobicyclic residues of aromatic character as well as appropriate partially or wholly saturated residues.

A preferred group of compounds of formulae I and II are those in which Z is $C_1-C_6$ alkyl, aryl selected from phenyl or naphthyl, aralkyl of the formula aryl-(ALK)$_m$- in which aryl is phenyl or naphthyl, m is an integer of 1 to 4 and ALK represents a straight or branched chain alkylene radical, or heterocyclic selected from a 5- or 6- membered heterocyclic ring containing 1 to 4 atoms selected from N, O or S, said alkyl radical being optionally substituted by one or more substituents selected from hydroxy, halo, amino, nitro, di($C_1-C_4$ alkyl) amino, carboxy, sulfo or cyano and said aryl, aralkyl or heterocyclic radicals being optionally substituted by one or more substituents selected from halo, $C_1-C_4$ alkyl, $C_1-C_4$ alkoxy, cyano, carboxyl, amino, nitro, $C_3-C_4$ cycloalkyl, $C_2-C_4$ alkenyl, trifluoromethyl, hydroxy, hydroxymethyl, $C_1-C_4$ alkylthio, $C_1-C_4$ alkylamino, di($C_1-C_4$ alkyl) amino, mercapto, phenyl, benzyl, alkoxyalkyl of up to 4 carbons or-($CH_2$)$_n$COOH in which n is an integer of 1 to 4. Examples of suitable heterocyclic radicals include thienyl, furyl, pyrazolyl, imidazolyl, isoimidazolyl, triazolyl, tetrazolyl, thiazolyl, thiadiazolyl, oxazolyl, oxadiazolyl, isothiazolyl, isoxazolyl, pyridyl, pyridazinyl, pyrazinyl, pyrimidihyl and triazinyl.

A most preferred group of compounds of formulae I and II are those in which Z is an optionally substituted 5- or 6- membered heterocyclic ring containing 1 to 4 atoms selected from N, O and S, the substituents being preferally those mentioned above. Especially preferred heterocyclic rings are optionally substituted triazole, thiadiazole, oxadiazole or tetrazole radicals. Within this group the most preferred Z substituents are 1,2,3-triazolyl, 2-methyl-1,3,4-thiadiazol-5-yl, 2-methyl-1,3,4-oxadiazol-5-yl, 1-N-methyltetrazolyl, 1-carboxymethyltetrazol-5-yl and 1-carboxyethyltetrazol-5-yl.

The term "(lower)alkyl" as used herein means both staight and branched chain aliphatic hydrocarbon radicals having from one to ten carbon atoms such as methyl, ethyl, proyl, isopropyl, butyl, isobutyl, t-butyl, amyl, hexyl, 2-ethylhexyl, heptyl, decyl, etc. Similarly, where the term "(lower)" is used as part of the description of another group, e.g., "(lower)-alkoxy", it refers to the alkyl portion of such group which is therefore described above in connection with "(lower)alkyl."

The pharmaceutically acceptable salts referred to above include the nontoxic carboxylic acid salts, e.g. nontoxic metallic salts such as sodium, potassium, calcium and aluminum, the ammonium salt and salts with nontoxic amines, e.g. trialkylamines, procaine, dibenzylamine, N-benzyl-$\beta$-phenethylamine, 1-ephenamine, N,N'-dibenzylethylenediamine, N-alkylpiperidine and other amines which have been used to form salts of penicillins and cephalosporins. When a basic group is present, as when it occurs in the 7-acyl group, the present invention also includes the pharmaceutically acceptable acid addition salts, e.g. salts with mineral acids such as hydrochloric, hydrobromic, hydroiodic, phosphoric, sulfuric and salts with organic acids such as maleic, acetic, citric, oxalic, succinic, benzoic, tartaric, fumaric, mandelic, ascorbic and malic. The term "pharmaceutically acceptable salts" is also meant to include nontoxic acid addition salts of the easily cleavable esters referred to above. The compounds which contain a basic group in radical R may also be present in the form of an internal salt, i.e. in the form of the zwitterion.

The easily cleavable esters referred to above include ester groups which are removable by methods, e.g. chemical or enzymatic hydrolysis, treatment with chemical reducing agents under mild conditions, irradiation with ultraviolet light or catalytic hydrogenation, which do not result in any appreciable destruction of the remaining portion of the molecule. Examples of suitable esters include those disclosed in U.S. Pat. Nos. 3,284,451 and 3,249,622 and U.K. Pat. Nos. 1,229,453 and 1,073,530. Esters which have been used previously in penicillin and cephalosporin chemistry include for example benzhydryl, p-nitrobenzyl, benzyl, trichloroethyl, silyl such as trimethylsilyl, phenacyl, p-methoxybenzyl, acetonyl, phthalidyl, indanyl and (lower)alkyl such as methyl, ethyl and t-butyl. Particularly preferred easily cleavable esters are those which are hydrolyzed under physiological conditions such as pivaloyloxymethyl, acetoxymethyl, phthalidyl, indanyl and methoxymethyl.

As the O-2-isocephem compounds of the present invention may possess one or more asymmetric carbon atoms, the invention includes all of the possible enantiomeric and diastereomeric forms of the compounds of the general formula II shown above. Resulting mixtures of isomers can be separated into the individual isomers according to methods which are known per se, e.g. fractional crystallization, adsorption chromatography or other suitable separation processes. Resulting racemates can be separated into the antipodes in the usual manner after introduction of suitable salt-forming groupings, e.g. by forming a mixture of diastereoisomeric salts with optically active salt-forming agents, separating the mixture into diastereoisomeric salts, and converting the separated salts into the free compounds, or by fractional crystallization from optically active solvents.

It will be appreciated that certain of the compounds of this invention exist in various states of solvation and the anhydrous as well as solvated forms are within the scope of the invention.

The free acid compounds of general formula II and general formula I wherein R is acylamido and physiologically hydrolyzed esters thereof together with the pharmaceutically acceptable salts of such free acids and esters are useful as antibacterial agents. The remaining acids, esters and salts of formula I are valuable intermediates which can be converted into the pharmacologically active compounds of formula II as by the processes described below.

Preferred compounds of formula II are those in which R is an acyl group selected from the acyl groups defined above under (i) to (xvi). Use of the acyl groups mentioned above as being preferred within categories (i) to (xvi) results in active end-products having the most advantageous pharmacological properties.

A preferred embodiment of the present invention consists of the compounds of formula II wherein R is an acyl group of the formula

wherein $R^a$ is aryl, substituted aryl, cycloalkyl, substituted cycloalkyl, cycloalkenyl, substituted cycloalkenyl or a nonaromatic or mesoionic heterocyclic group, and n is an integer from 1 to 4;

wherein n is a integer from 1 to 7, the alkyl portion of said acyl group being straight or branched and optionally interrupted by an oxygen or sulphur atom;

wherein n is an integer from 2-7, the alkenyl portion of said acyl group being straight or branched and optionally interrupted by an oxygen or sulfur atom;

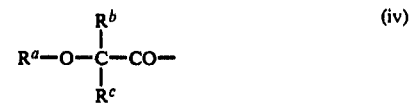

wherein $R^a$ is as defined above under (i) and in addition may be benzyl, $C_1$-$C_6$ alkyl or (lower)alkoxycarbonyl and $R^b$ and $R^c$ which may be the same or different each represent hydrogen, phenyl, benzyl, phenethyl or $C_1$-$C_6$ alkyl;

wherein $R^a$ is as defined above under (i) and in addition may be benzyl or $C_1$-$C_6$ alkyl and $R^b$ and $R^c$ are as defined under (iv);

          (vi)

$R^aX(CH_2)_mCO-$          (vi)

wherein $R^a$ is as defined under (i) and in addition may be benzyl; X is oxygen or sulfur; and m is an integer of 2–5;

$R^aCO-$          (vii)

wherein $R^a$ is as defined under (i);

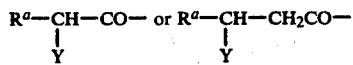          (viii)

wherein $R^a$ is as defined under (i) and Y is hydrazino, guanidino, ureido, thioureido, substituted thioureido, allophanamido, 3-guanyl-1-ureido, cyanamino, azido, 3-(2-furoyl)ureido, 3-(benzoyl)ureido, amino, acylamino, a group obtained by reacting the amino group Y with an aldehyde or ketone, hydroxy, etherified hydroxy esterified hydroxy, carboxy, esterified carboxy, triazolyl, tetrazolyl, cyano, halogeno, acyloxy, sulfo, sulfoamino or esterified sulfo;

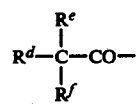          (ix)

wherein $R^d$, $R^e$ and $R^f$ which may be the same or different may each represent $C_1$-$C_6$ alkyl, phenyl or substituted phenyl;

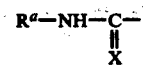          (x)

wherein $R^a$ is as defind under (i) and in addition may be hydrogen, $C_1$-$C_6$ alkyl, halogen, substituted $C_1$-$C_6$ alkyl, phenethyl, phenoxymethyl, benzyl or $R^a$-CO-and X is oxygen or sulfur;

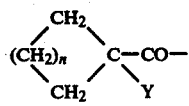          (xi)

wherein Y is as defined under (viii) and n is an integer of 1–4;

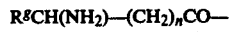          (xii)

wherein n is an integer of 1–10 or

wherein m is 0 or an integer from 1-10 and n is 0, 1 or 2; $R^g$ is hydrogen or an alkyl, aralkyl or carboxy group or a group as defined under $R^a$ in (i) above; and Ar is an arylene group;

          (xiii)

wherein $R^h$ is an aliphatic, araliphatic or aromatic group;

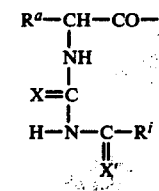          (xiv)

wherein $R^a$ is as defined under (i); X is oxygen or sulfur; X' is oxygen or imino and $R^i$ is (lower)alkyl, $C_4$—$C_7$ cycloalkyl, monohalo (lower)alkyl, dichloromethyl, trichloromethyl, (lower)alkenyl of 2–6 carbon atoms,

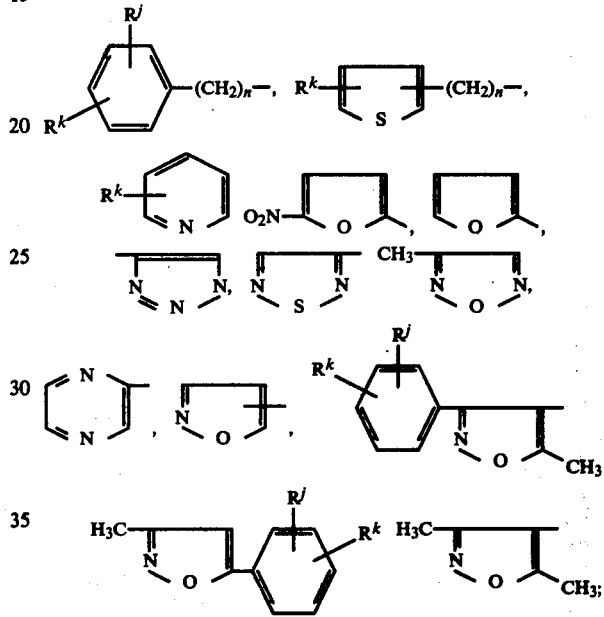

n is an integer from 0 to 3 inclusive and each of $R^k$ and $R^j$ is hydrogen, nitro, di(lower)-alkylamino, (lower)alkanoylamino, (lower)-alkanoyloxy, $C_1$-$C_6$ alkyl, $C_1$-$C_6$ alkoxy, sulfamyl, chloro, iodo, bromo, fluoro or trifluoromethyl;

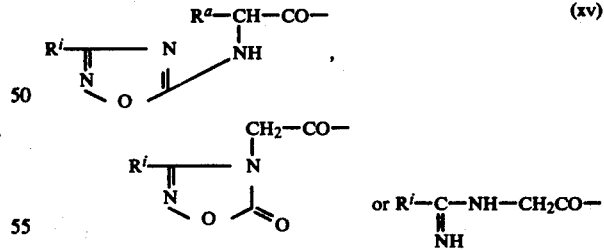          (xv)

wherein $R^a$ is as defined under (i) and $R^i$ is as defined under (xiv); or

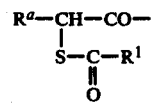          (xvi)

wherein $R^a$ is as defined under (i) and $R^1$ is (lower)-alkyl, $C_3$-$C_{12}$ cycloalkyl, phenyl, a monocyclic heterocyclic radial having 5 or 6 atoms exclusive of hydrogen which are C, S, N or O, no more than 2 atoms being other than C, or a substituted monocyclic heterocyclic radical as defined above having one or more substituents selected from halo, (lower)alkyl, (lower)alkoxy or phenyl.

Another preferred embodiment of the present invention consists of the compounds of formula II wherein R is an acyl group of the formula $$R^a C_n H_{2n} CO— \quad (i)$$

wherein $R^a$ is (a) aryl selected from phenyl, 2-thienyl, 3-thienyl, furyl, 4-isoxazolyl, pyridyl, tetrazolyl, sydnone-3 or -4, imidazolyl, naphthoyl, quinoxalinyl, triazolyl, isothiazolyl, thiadiazolyl, thiazolyl, oxazolyl, oxadiazolyl, pyrazolyl, furazan, pyrazinyl, pyrimidinyl, pyridazinyl or triazinyl; (b) substituted aryl in which the aryl groups defined above under (a) are substituted by one or more radicals selected from chloro, bromo, iodo, fluoro, nitro, amino, cyano, (lower)alkanoyloxy, (lower)alkanoyl, (lower)alkoxyamino, (lower)alkoxy, (lower)alkyl, (lower)alkylamino, hydroxy, guanidino, (lower)alkylthio, carboxy, phenyl, halophenyl, trifluoromethyl, di(lower)alkylamino, sulfamyl, (lower)alkanoylamino, phenyl(lower)alkylamido, cycloalkylamino, allylamido, morpholinocarbonyl, pyrrolidinocarbonyl, piperidinocarbonyl, tetrahydropyridino, furfurylamido or N-alkyl-N-anilino; (c) $C_3$–$C_{12}$ cycloalkyl; (d) substituted $C_3$–$C_{12}$ cycloalkyl in which the substituents are one or more radicals selected from chloro, bromo, fluoro, iodo, nitro, trifluoromethyl, $C_1$–$C_4$ alkyl, $C_1$–$C_4$ alkylamino, $C_1$–$C_2$ alkoxy or amino; (e) $C_3$–$C_{12}$ cycloalkenyl, said cycloalkenyl group having 1 or 2 double bonds; or (f) substituted $C_3$–$C_{12}$ cycloalkenyl, said cycloalkenyl group having 1 or 2 double bonds and being substituted by one or more radicals selected from chloro, bromo, fluoro, iodo, nitro, trifluoromethyl, $C_1$–$C_4$ alkyl, $C_1$–$C_4$ alkylamino, $C_1$–$C_2$ alkoxy or amino; and n is an integer from 1–4;

$$C_n H_{2n+1} CO— \quad (ii)$$

wherein n is an integer from 1–7, the alkyl portion of said acyl group being straight or branched and optionally interrupted by an oxygen or sulfur atom;

$$C_n H_{2n-1} CO— \quad (iii)$$

wherein n is an integer from 2–7, the alkenyl portion of said acyl group being straight or branched and optionally interrupted by an oxygen or sulfur atom;

$$R^a—O—\underset{R^c}{\underset{|}{\overset{R^b}{\overset{|}{C}}}}—CO— \quad (iv)$$

wherein $R^a$ is as defined above under (i) and in addition may be benzyl, $C_1$–$C_6$ alkyl or (lower)alkoxy carbonyl and $R^b$ and $R^c$ may be the same or different each represent hydrogen, phenyl, benzyl, phenethyl or $C_1$–$C_6$ alkyl;

$$R^a—S—\underset{R^c}{\underset{|}{\overset{R^b}{\overset{|}{C}}}}—CO— \quad (v)$$

wherein $R^a$ is as defined above under (i) and in addition may be benzyl or $C_1$–$C_6$ alkyl and $R^b$ and $R^c$ are as defined under (iv);

$$R^a X(CH_2)_m CO— \quad (vi)$$

wherein $R^a$ is as defined under (i) and in addition may be benzyl; X is oxygen or sulfur; and m is an integer of 2–5;

$$R^a CO— \quad (vii)$$

wherein $R^a$ is as defined under (i);

$$R^a—\underset{Y}{\underset{|}{CH}}—CO— \text{ or } R^a—\underset{Y}{\underset{|}{CH}}—CH_2 CO— \quad (viii)$$

wherein $R^a$ is as defined under (i) and Y is hydrazino, guanidino, ureido; substituted ureido of the formula $$—NH—\underset{S}{\overset{\|}{C}}—N\underset{R^q}{\overset{R^p}{\diagup}}$$

in which $R^p$ is hydrogen or $C_1$–$C_8$ alkyl and $R^q$ is hydrogen, $C_1$–$C_8$ alkyl, $C_2$–$C_8$ alkenyl, phenyl, benzoyl, $C_1$–$C_8$ alkoxy-$C_1$–$C_8$ alkyl or (carbo-$C_1$–$C_8$ alkoxy)C$_1$–$C_8$ alkyl; allophanamido; 3-guanyl-1-ureido; 3-(2-furoyl)-ureido; 3-benzoyl)ureido; cyano; cyanamino; azido; amino; a group obtained by reacting the amino group Y with acetone, formaldehyde, acetaldehyde, butyraldehyde, acetylacetone, methyl acetoacetate, benzaldehyde, salicylaldehyde, methyl ethyl ketone or ethyl acetoacetate; hydroxy; (lower)alkoxy; carboxy; 5-indanyloxycarbonyl; triazolyl; tetrazolyl; halogeno; formyloxy; (lower)alkanoyloxy; sulfo; or sulfoamino;

$$R^d—\underset{R^f}{\underset{|}{\overset{R^e}{\overset{|}{C}}}}—CO— \quad (ix)$$

wherein $R^d$, $R^e$ and $R^f$ which may be the same or different may each represent $C_1$–$C_6$ alkyl, phenyl or phenyl substituted by one or more radicals selected from chloro, bromo, iodo, fluoro, trifluoromethyl, nitro, amino, cyano, (lower)alkanoyloxy, (lower)alkanoyl, (lower)-alkoxyamino, (lower)alkoxy, (lower)alkyl, (lower)-alkylamino, hydroxy, (lower)alkylthio, carboxy, di(lower)alkylamino or sulfamyl;

$$R^a—NH—\underset{X}{\overset{\|}{C}}— \quad (x)$$

wherein $R^a$ is as defined under (i) and in addition may be hydrogen, $C_1$–$C_6$ alkyl, halogen-substituted $C_1$–$C_6$ alkyl, phenethyl, phenoxymethyl, benzyl or $R^a$-CO- and X is oxygen or sulfur.

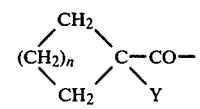

wherein Y is as defined under (viii) and n is an integer of 1–4;

$$R^g CH(NH_2)(CH_2)_n CO- \quad (xii)$$

wherein n is an integer of 1–10, or

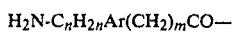

wherein m is 0 or an integer from 1–10, and n is 0, 1 or 2; $R^g$ is hydrogen, (lower)alkyl, phenyl, benzyl or carboxy and Ar is p-phenylene or 1,4-naphthylene;

$$R^h CO.CO— \quad \text{(xii)}$$

wherein $R^h$ is 2-thienyl; 3-thienyl; α-naphthyl; 2-phenanthryl or a mono-, di- or tri-substituted phenyl group, the substituents being selected from chloro, bromo, iodo, fluoro, amino, di(lower)alkylamino, (lower)alkyl, (lower)alkoxy, nitro or (lower)-alkanoylamino;

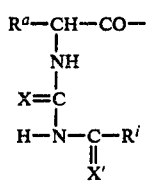
(xiv)

wherein $R^a$ is as defined under (i); X is oxygen or sulfur; X' is oxygen or imino; and $R^i$ is (lower)alkyl, cycloalkyl having 4, 5, 6 or 7 carbon atoms, monohalo (lower)alkyl, dichloromethyl, trichloromethyl, (lower)alkenyl of 2–6 carbon atoms,

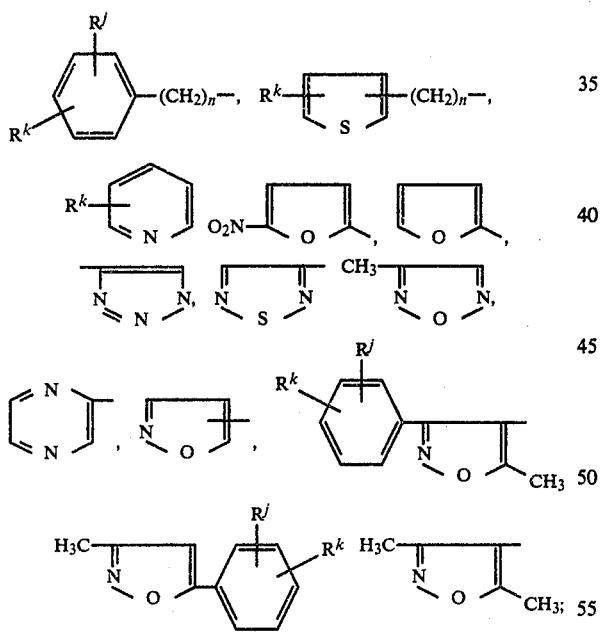

n is an integer from 0 to 3 inclusive and each of $R^k$ and $R^j$ is hydrogen, nitro, di(lower)-alkylamino, (lower)alkanoylamino, (lower)-alkanoyloxy, $C_1$–$C_6$ alkyl, $C_1$–$C_6$ alkoxy, sulfamyl, chloro, iodo, bromo, fluoro, or trifluoromethyl;

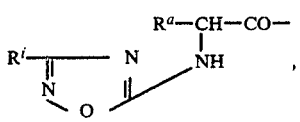
(xv)

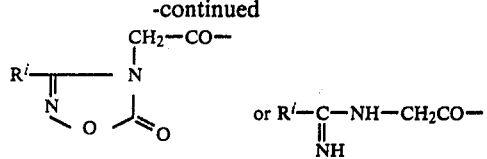

wherein $R^a$ is as defined under (i) and $R^i$ is as defined under (xiv); or

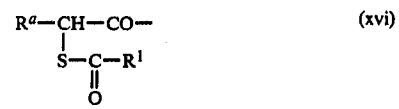
(xvi)

wherein $R^a$ is as defined under (i) and $R^1$ is (lower)alkyl, cycloalkyl of 3–12 carbon atoms, phenyl, a monocyclic heterocyclic radical having 5 or 6 atoms exclusive of hydrogen which are C, S, N or O, no more than 2 atoms being other than C, or a substituted monocyclic heterocyclic radical as defined above having one or more substituents selected from halo, (lower)alkyl, (lower)alkoxy or phenyl.

Another preferred embodiment of the present invention consists of the compounds of formula II wherein R is as defined immediately above and Z is $C_1$–$C_6$ alkyl, aryl selected from phenyl or naphthyl, aralkyl of the formula aryl—$(ALK)_m$— in which aryl is phenyl or naphthyl, m is an integer of 1 to 4 and ALK represents a straight or branched chain alkylene radical, or heterocyclic selected from a 5- or 6- membered heterocyclic ring containing 1 to 4 atoms selected from N, O or S, said alkyl radical being optionally substituted by one or more substituents selected from hydroxy, halo, amino, nitro, di ($C_1$–$C_4$ alkyl) amino, carboxy, sulfo or cyano and said aryl, aralkyl or heterocyclic radicals being optionally substituted by one or more substituents selected from halo, $C_1$–$C_4$ alkyl, $C_1$–$c_4$ alkoxy, cyano, carboxyl, amino, nitro, $C_3$–$C_4$ cycloalkyl, $C_2$–$C_4$ alkenyl, trifluoromethyl, hydroxy, hydroxymethyl, $C_1$–$C_4$ alkylthio; $C_1$–$C_4$ alkylamino, di ($C_1$–$C_4$ alkyl) amino, mercapto, phenyl, benzyl, alkoxyalkyl of up to 4 carbons or —$(CH_2)_n COOH$ in which n is an integer of 1 to 4.

Within this group of compounds, a preferred subclass consists of the compounds wherein R is an acyl group of the formula

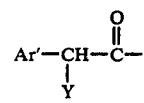

wherein Ar' is a radical of the formula

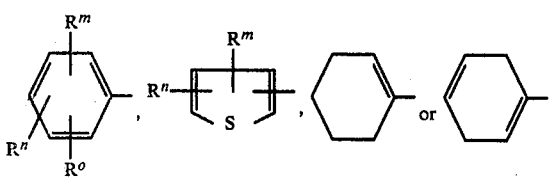

in which $R^m$, $R^n$ and $R^o$ are alike or different and each is hydrogen, hydroxy, (lower)alkyl, cyano, (lower)alkoxy, chloro, bromo, iodo, fluoro, trifluoromethyl, nitro, amino, (lower)alkylamino, di(lower)-alkylamino, (lower)alkanoyl, (lower)alkanoyloxy or phenyl and Y is amino or a group obtained by reacting the amino group with acetaldehyde, formaldehyde or acetone; fluoro; chloro; bromo; iodo; hydroxy; (lower)alkanoyloxy; carboxy; guanidino; 3-guanyl-1-ureido; 3-(2-furoyl-)ureido; 3-benzoylureido; sulfo, sulfoamino, ureido, thioureido; (lower)alkoxy; cyano; cyanamino; or indanyloxycarbonyl.

A second preferred subclass within this group of compounds consists of the compounds wherein R is an acyl group of the formula

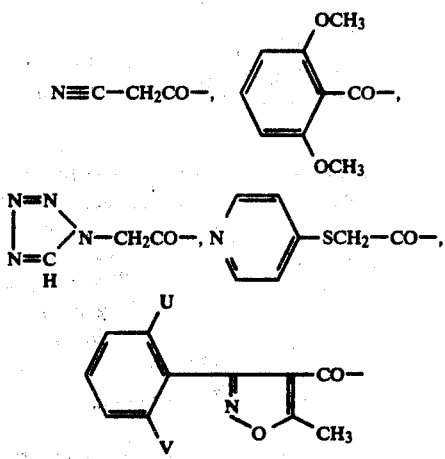

wherein U and V are alike or different and each is hydrogen, chloro or fluoro;

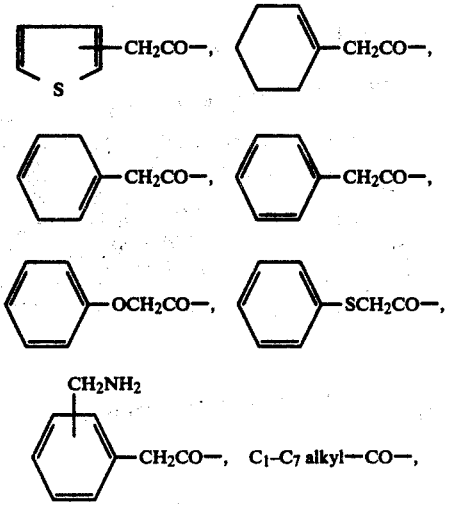

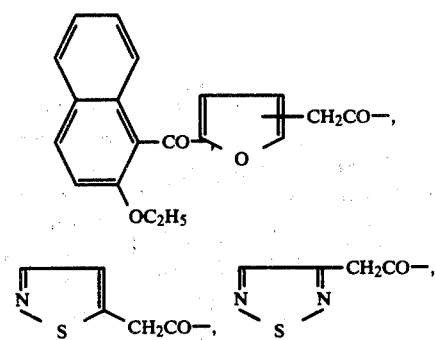

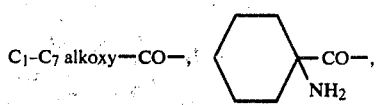

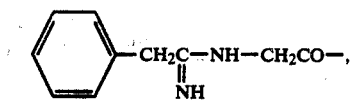

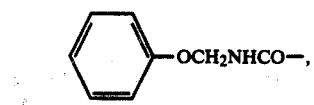

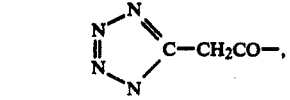

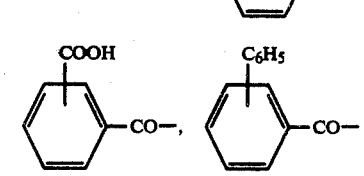

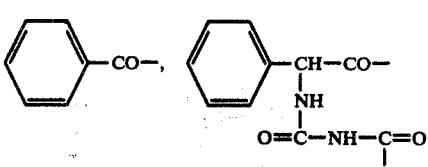

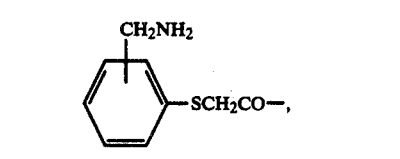

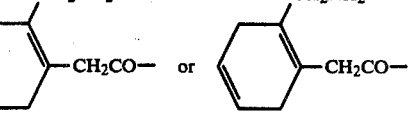

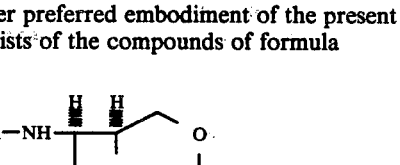

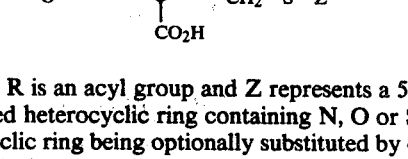

Another preferred embodiment of the present invention consists of the compounds of formula

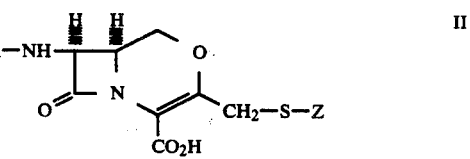

in which R is an acyl group and Z represents a 5- or 6-membered heterocyclic ring containing N, O or S, said heterocyclic ring being optionally substituted by one or more substituents selected from halo, $C_1$-$C_4$ alkyl, $C_1$-$C_4$ alkoxy, cyano, carboxyl, amino, nitro, $C_3$-$C_4$ cycloalkyl, C₂–C₄ alkenyl, trifluoromethyl, hydroxy, hydroxymethyl, C₁–C₄ alkylthio, C₁–C₄ alkylamino, di (C₁–C₄alkyl) amino mercapto, phenyl, benzyl, alkoxyalkyl of up to 4 carbons or —(CH₂)ₙCOOH in which n is an integer of 1 to 4, and easily cleavable esters and pharmaceutically acceptable salts thereof.

Within this group of compounds, a preferred subclass consists of the compounds wherein R is an acyl group of the formula

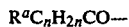  (i)

wherein R^a is aryl, substituted aryl, cycloalkyl, substituted cycloalkyl, cycloalkenyl, substituted cycloalkenyl or a nonaromatic or mesoionic heterocyclic group, and n is an integer from 1 to 4;

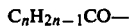  (ii)

wherein n is an integer from 1–7, the alkyl portion of said acyl group being straight or branched and optionally interrupted by an oxygen or sulphur atom;

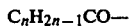  (iii)

wherein n is an integer from 2–7, the alkenyl portion of said acyl group being straight or branched and optionally interrupted by an oxygen or sulfur atom;

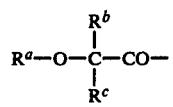  (iv)

wherein R^a is as defined above under (i) and in addition may be benzyl, C₁–C₆ alkyl or (lower)alkoxycarbonyl and R^b and R^c which may be the same or different each represent hydrogen, phenyl, benzyl, phenethyl or C₁–C₆ alkyl;

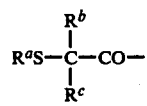  (v)

wherein R^a is as defined above under (i) and in addition may be benzyl or C₁–C₆ alkyl and R^b and R^c are as defined under (iv);

  (vi)

wherein R^a is as defined under (i) and in addition may be benzyl; X is oxygen or sulfur; and m is an integer of 2–5;

  (vii)

wherein R^a is as defined under (i);

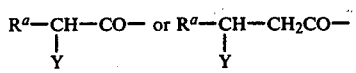  (viii)

wherein R^a is as defined under (i) and Y is hydrazino, guanidino, ureido, thioureido, substituted thioureido, allophanamido, 3-guanyl-1-ureido, cyanamino, azido, 3-(2-furoyl)ureido, 3-(benzoyl)ureido, amino, acylamino, a group obtained by reacting the amino group Y with an aldehyde or ketone, hydroxy, etherified hydroxy, esterified hydroxy, carboxy, esterified carboxy, triazolyl, tetrazolyl, cyano, halogeno, acyloxy, sulfo, sulfoamino or esterified sulfo;

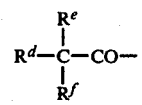  (ix)

wherein R^d, R^e and R^f which may be the same or different may each represent C₁–C₆ alkyl, phenyl or substituted phenyl;

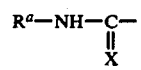  (x)

wherein R^a is as defined under (i) and in addition may be hydrogen, C₁–C₆ alkyl, halogen, substituted C₁–C₆ alkyl, phenethyl, phenoxymethyl, benzyl, or R^a—CO— and X is oxygen or sulfur;

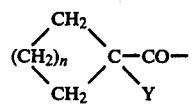  (xi)

wherein Y is as defined under (viii) an n is an integer of 1–4;

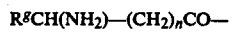  (xii)

wherein n is an integer of 1–10 or

wherein m is 0 or an integer from 1–10 and n is 0, 1 or 2; R^g is hydrogen or an alkyl, aralkyl or carboxy group or a group as defined under R^a in (i) above; and Ar is an arylene group;

  (xiii)

wherein R^h is an aliphatic, araliphatic or aromatic group;

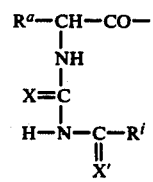  (xiv)

wherein R^a is as defined under (i); X is oxygen or sulfur; X' is oxygen or imino and R^i is (lower)alkyl, C₄–C₇ cycloalkyl, monohalo (lower)alkyl, dichloromethyl, trichloromethyl, (lower)alkenyl of 2–6 carbon atoms,

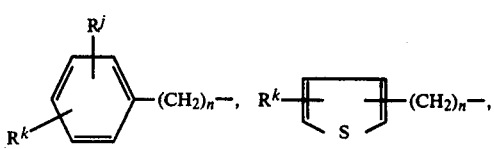

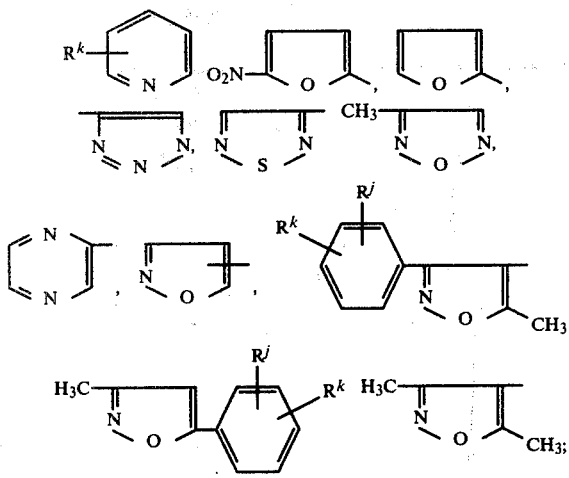

n is an integer from 0 to 3 inclusive and each of $R^k$ and $R^j$ is hydrogen, nitro, di(lower)-alkylamino, (lower)alkanoylamino, (lower)-alkanoyloxy, $C_1$-$C_6$ alkyl, $C_1$-$C_6$ alkoxy, sulfamyl, chloro, iodo, bromo, fluoro or trifluoromethyl;

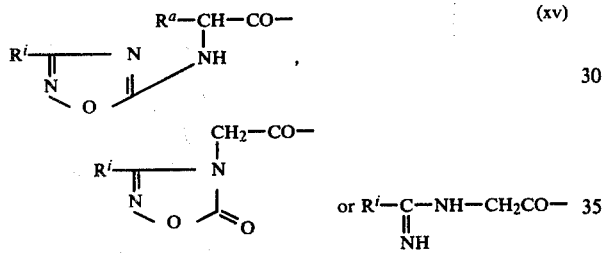

wherein $R^a$ is as defined under (i) and $R^i$ is as defined under (xiv); or

wherein $R^a$ is as defined under (i) and $R^1$ is (lower)-alkyl, $C_3$-$C_{12}$ cycloalkyl, phenyl, a monocyclic heterocyclic radical having 5 or 6 atoms exclusive of hydrogen which are C, S, N or O, no more than 2 atoms being other than C, or a substituted monocyclic heterocyclic radical as defined above having one or more substituents selected from halo, (lower)alkyl, (lower)alkoxy or phenyl.

Another preferred subclass within this group consists of the compounds wherein R is an acyl group of the formula $$R^a C_n H_{2n} CO— \quad (i)$$

wherein $R^a$ is (a) aryl selected from phenyl, 2-thienyl, 3-thienyl, furyl, 4-isoxazolyl, pyridyl, tetrazoyl, sydnone-3 or -4, imidazolyl, naphthoyl, quinoxalinyl, triazolyl, isothiazolyl, thiadiazolyl, thiazolyl, oxazolyl, oxadiazolyl, pyrazolyl, furazan, pyrazinyl, pyrimidinyl, pyridazinyl or triazinyl; (b) substituted aryl in which the aryl groups defined above under (a) are substituted by one or more radicals selected from chloro, bromo, iodo, fluoro, nitro, amino, cyano, (lower)alkanoyloxy, (lower)alkanoyl, (lower)alkoxyamino, (lower)alkoxy, (lower)alkyl, (lower)alkylamino, hydroxy, guanidino, (lower)alkylthio, carboxy, phenyl, halophenyl, trifluoromethyl, di(lower)alkylamino, sulfamyl, (lower)alkanoylamino, phenyl(lower)-alkylamido, cycloalkylamino, allylamido, morpholinocarbonyl, pyrrolidinocarbonyl, piperidinocarbonyl, tetrahydropyridino, furfurylamido or N-alkyl-N-anilino; (c) $C_3$-$C_{12}$ cycloalkyl; (d) substituted $C_3$-$C_{12}$ cycloalkyl in which the substituents are one or more radicals selected from chloro, bromo, fluoro, iodo, nitro, trifluoromethyl, $C_1$-$C_4$ alkyl, $C_1$-$C_4$ alkylamino, $C_1$-$C_2$ alkoxy or amino; (e) $C_3$-$C_{12}$ cycloalkenyl, said cycloalkenyl group having 1 or 2 double bonds; or (f) substituted $C_3$-$C_{12}$ cycloalkenyl, said cycloalkenyl group having 1 or 2 double bonds and being substituted by one or more radicals selected from chloro, bromo, fluoro, iodo, nitro, trifluoromethyl, $C_1$-$C_4$ alkyl, $C_1$-$C_4$ alkylamino, $C_1$-$C_2$ alkoxy or amino; and n is an integer from 1–4;

$$C_n H_{2n+1} CO— \quad (ii)$$

wherein n is an integer from 1–7, the alkyl portion of said acyl group being straight or branched and optionally interrupted by an oxygen or sulfur atom;

$$C_n H_{2n-1} CO— \quad (iii)$$

wherein n is an integer from 2–7, the alkenyl portion of said acyl group being straight or branched and optionally interrupted by an oxygen or sulfur atom;

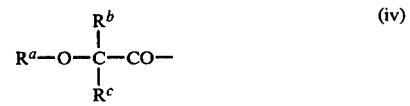

wherein $R^a$ is as defined above under (i) and in addition may be benzyl, $C_1$-$C_6$ alkyl or (lower)alkoxycarbonyl and $R^b$ and $R^c$ which may be the same or different each represent hydrogen, phenyl, benzyl, phenethyl or $C_1$-$C_6$ alkyl;

wherein $R^a$ is as defined above under (i) and in addition may be benzyl or $C_1$-$C_6$ alkyl and $R^b$ and $R^c$ are as defined under (iv);

$$R^a X (CH_2)_m CO— \quad (vi)$$

wherein $R^a$ is as defined under (i) and in addition may be benzyl; X is oxygen or sulfur; and m is an integer of 2–5;

$$R^a CO— \quad (vii)$$

wherein $R^a$ is as defined under (i);

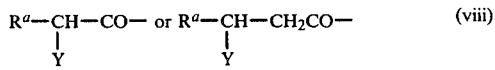

wherein $R^a$ is as defined under (i) and Y is hydrazino, guanidino, ureido; substituted ureido of the formula

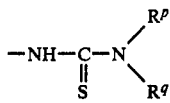

in which $R^p$ is hydrogen or $C_1$-$C_8$ alkyl and $R^q$ is hydrogen, $C_1$-$C_8$ alkyl, $C_2$-$C_8$ alkenyl, phenyl, benzoyl, $C_1$-$C_8$ alkoxy-$C_1$-$C_8$ alkyl or (carbo-$C_1$-$C_8$ alkoxy)$C_1$-$C_8$ alkyl; allophanamido; 3-guanyl-1-ureido; 3-(2-furoyl)-ureido; 3-(benzoyl)ureido; cyano; cyanamino; azido; amino; a group obtained by reacting the amino group Y with acetone, formaldehyde, acetaldehyde, butyraldehyde, acetylacetone, methyl acetoacetate, benzaldehyde, salicylaldehyde, methyl ethyl ketone or ethyl acetoacetate; hydroxy; (lower)alkoxy; carboxy; 5-indanyloxycarbonyl; triazolyl; tetrazolyl; halogeno; formyloxy; (lower)alkanoyloxy; sulfo; or sulfoamino;

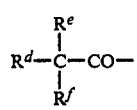  (ix)

wherein $R^d$, $R^e$ and $R^f$ which may be the same or different may each represent $C_1$-$C_6$ alkyl, phenyl or phenyl substituted by one or more radicals selected from chloro, bromo, iodo, fluoro, trifluoromethyl, nitro, amino, cyano, (lower)alkanoyloxy, (lower)alkanoyl, (lower)-alkoxyamino, (lower)alkoxy, (lower)alkyl, (lower)alkylamino, hydroxy, (lower)alkylthio, carboxy, di(lower)alkylamino or sulfamyl;

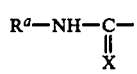  (x)

wherein $R^a$ is a defined under (i) and in addition may be hydrogen, $C_1$-$C_6$ alkyl, halogen-substituted $C_1$-$C_6$ alkyl, phenethyl, phenoxymethyl, benzyl or $R^a$—CO— and X is oxygen or sulfur.

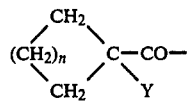  (xi)

wherein Y is as defined under (viii) and n is an integer of 1–4;

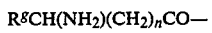  (xii)

wherein n is an integer of 1–10, or

wherein m is 0 or an integer from 1–10, and n is 0, 1 or 2; $R^g$ is hydrogen, (lower)alkyl, phenyl, benzyl or carboxy and Ar is p-phenylene or 1,4-naphthylene;

$R^hCO\ CO—$  (xiii)

wherein $R^h$ is 2-thienyl; 3-thienyl; α-naphthyl; 2-phenanthryl or a mono-, di- or tri-substituted phenyl group, the substituents being selected from chloro, bromo, iodo, fluoro, amino, di(lower)alkylamino, (lower)alkyl, (lower)alkoxy, nitro or (lower)alkanoylamino;

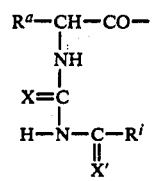  (xiv)

wherein $R^a$ is as defined under (i); X is oxygen or sulfur; X′ is oxygen or imino; and $R^i$ is (lower)alkyl, cycloalkyl having 4, 5, 6 or 7 carbon atoms, monohalo (lower)alkyl, dichloromethyl, trichloromethyl, (lower)alkenyl of 2–6 carbon atoms,

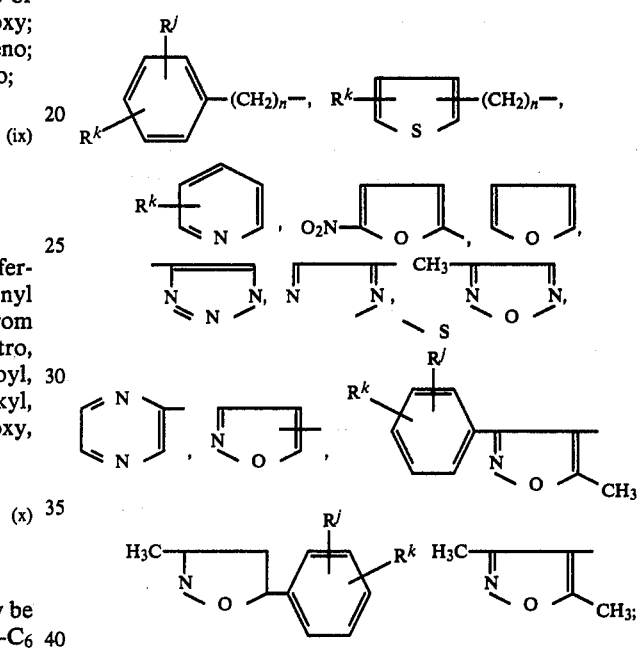

n is an integer from 0 to 3 inclusive and each of $R^k$ and $R_j$ is hydrogen, nitro, di(lower)-alkylamino, (lower)alkanoylamino, (lower)-alkanoyloxy, $C_1$-$C_6$ alkyl, $C_1$-$C_6$ alkoxy, sulfamyl, chloro, iodo, bromo, fluoro, or trifluoromethyl;

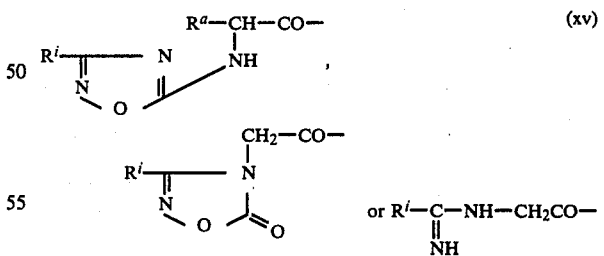  (xv)

wherein $R^a$ is as defined under (i) and $R^i$ is as defined under (xiv); or

  (xvi)

wherein $R^a$ is as defined under (i) and $R^1$ is (lower)alkyl, cycloalkyl of 3–12 carbon atoms, phenyl, a monocyclic heterocyclic radical having 5 or 6 atoms exclusive or hydrogen which are C, S, N or O, no more than 2 atoms being other than C, or a substituted monocyclic heterocyclic radical as defined above having one or more substituents selected from halo, (lower)alkyl, (lower)alkoxy or phenyl.

Another preferred subclass within this group consists of the compounds wherein R is an acyl group of the formula $R^a C_n H_{2n} CO-$ in which $R^a$ is phenyl; phenyl substituted by one or more radicals selected from chloro, bromo, iodo, fluoro, nitro, amino, (lower) alkyl, guanidino, (lower) alkylthio, cyano, (lower) alkoxy, sulfamyl, (lower) alkylamino, hydroxy, acetoxy or trifluoromethyl; 2-thienyl; 3-thienyl; tetrazolyl; sydnone-3- or sydnone-4; furyl; isothiazolyl; thiadiazolyl optionally substituted with phenyl; oxadiazolyl optionally substituted with phenyl; oxadiazolyl optionally substituted with phenyl; thiaoxazolyl; imidazolyl; triazolyl; oxazolyl; pyridyl; furazan optionally substituted at the 3-position with methoxy; 4-isoxazolyl optionally substituted at the 5-position with methyl and at the 3-position with phenyl or halophenyl; 1,4-cyclohexadienyl; 1-cyclohexenyl and 1-aminocyclohexyl. The most preferred compounds of this subclass are those in which n is 1.

Another preferred subclass within this group consists of the compounds wherein R is an acyl group of the formula

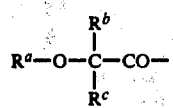

in which $R^a$ is phenyl and $R^b$ and $R^c$ which may be the same or different each represent hydrogen, phenyl, benzyl, phenethyl or $C_1-C_6$ alkyl.

Another preferred subclass within this group consists of the compounds wherein R is an acyl group of the formula

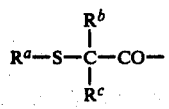

in which $R^a$ is phenyl; phenyl substituted with one or more radicals selected from chloro, bromo, iodo, fluoro, nitro, amino, (lower)alkyl, (lower)alkylthio, cyano, (lower)alkoxy, (lower)alkylamino, hydroxy, acetoxy or trifluoromethyl; 3-pyridyl or 4-pyridyl; and $R^b$ and $R^c$ are hydrogen.

Another preferred subclass within this group consists of the compounds wherein R is an acyl group of the formula $R^a CO-$ in which $R^a$ is phenyl; phenyl substituted with one or more radicals selected from chloro, bromo, iodo, fluoro, nitro, amino, (lower)alkyl, (lower)alkylthio, cyano, (lower)alkoxy, (lower)alkylamino, di(lower)alkylamino, hydroxy, acetoxy or trifluoromethyl; 2-ethoxynaphthoyl; 3-phenyl-5-methylisoxazol-4-yl; 3-o-chlorophenyl-5-methylisoxazol-4-yl; 3-(2,6-dichlorophenyl)-5-methylisoxazol-4-yl; or 1-aminocyclohexyl.

Another preferred subclass within this group consists of the compounds wherein R is an acyl group of the formula

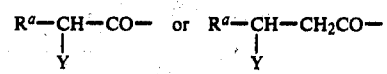

in which $R^a$ is (a) aryl selected from phenyl, 2-thienyl, 3-thienyl, furyl, 4-isoxazolyl, pyridyl, tetrazolyl, sydnone-3 or -4, imidazolyl, naphthoyl, quinoxalinyl, triazolyl, isothiazolyl, thiadiazolyl, thiazolyl, oxazolyl, oxadiazolyl, pyrazolyl, furazan, pyrazinyl, pyrimidinyl, pyridazinyl or triazinyl; (b) substituted aryl in which the aryl groups defined above under (a) are substituted by one or more radicals selected from chloro, bromo, iodo, fluoro, nitro, amino, cyano, (lower)alkanoyloxy, (lower)alkanoyl, (lower)alkoxyamino, (lower)alkoxy, (lower)alkyl, (lower)alkylamino, hydroxy, guanidino, (lower)alkythio, carboxy, phenyl, halophenyl, trifluoromethyl, di(lower)alkylamino, sulfamyl, (lower)alkanoylamino, phenyl(lower)alkylamido, cycloalkylamino, allylamido, morpholinocarbonyl, pyrrolidinocarbonyl, piperidinocarbonyl, tetrahydropyridino, furfurylamido or N-alkyl-N-anilino; (c) $C_3-C_{12}$ cycloalkyl; (d) substituted $C_3-C_{12}$ cycloalkyl in which the substituents are one or more radicals selected from chloro, bromo, fluoro, iodo, nitro, trifluoromethyl, $C_1-C_4$ alkyl, $C_1-C_4$ alkylamino, $C_1-C_2$ alkoxy or amino; (e) $C_3-C_{12}$ cycloalkenyl, said cycloalkenyl group having 1 or 2 double bonds; or (f) substituted $C_3-C_{12}$ cycloalkenyl, said cycloalkenyl group having 1 or 2 double bonds and being substituted by one or more radicals selected from chloro, bromo, fluoro, iodo, nitro, trifluoromethyl, $C_1-C_4$ alkyl, $C_1-C_4$ alkylamino, $C_1-C_2$ alkoxy or amino; and Y is hydrazino, guanidino, ureido; substituted ureido of the formula

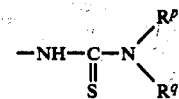

in which $R^p$ is hydrogen or $C_1-C_8$ alkyl and $R^q$ is hydrogen, $C_1-C_8$ alkyl, $C_2-C_8$ alkenyl, phenyl, benzoyl, $C_1-C_8$ alkoxy-$C_1-C_8$ alkyl or (carbo--$C_1-C_8$ alkoxy)C-1-$C_8$ alkyl; allophanamido; 3-guanyl-1-ureido; 3-(2-furoyl)-ureido; 3-(benzoyl)ureido; cyano; cyanamino; azido; amino; a group obtained by reacting the amino group Y with acetone, formaldehyde, acetaldehyde, butyraldehyde, acetylacetone, methyl acetoacetate, benzaldehyde, salicylaldehyde, methyl ethyl ketone or ethyl acetoacetate; hydroxy; (lower)alkoxy; carboxy; 5-indanyloxycarbonyl; triazolyl; tetrazolyl; halogeno; formyloxy; (lower)alkanoyloxy; sulfo; or sulfoamino;

Another preferred subclass within this group consists of the compounds wherein R is an acyl group of the formula

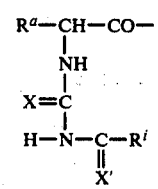

in which $R^a$ is 2-thienyl; 3-thienyl; phenyl; or phenyl substituted by one or more radicals selected from nitro, di(lower)alkylamino, (lower)alkanoylamino, amino, hydroxy, (lower)alkanoyloxy, $C_1-C_6$ alkyl, $C_1-C_6$ alkoxy, sulfamyl, chloro, bromo, iodo, fluoro, or trifluoromethyl; X is oxygen; X' is oxygen or imino; and $R^i$ is (lower)alkyl, phenyl, 2-thienyl, 3-thienyl, 2-furyl or 5-nitro-2-furyl. The most preferred compounds of this subclass are those in which $R^a$ is phenyl, p-hydroxyphenyl, 2-thienyl or 3-thienyl, X' is oxygen and $R^i$ is phenyl or 2-furyl.

A most preferred subclass within this group consists of the compounds wherein R is an acyl group of the formula

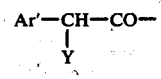

in which Ar' is a radical of the formula

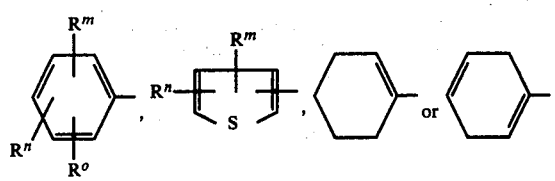

in which $R^m$, $R^n$ and $R^o$ are alike or different and each is hydrogen, hydroxy, (lower)alkyl, cyano, (lower)alkoxy, chloro, bromo, iodo, fluoro, trifluoromethyl, nitro, amino, (lower)alkylamino, di(lower)-alkylamino, (lower)alkanoyl, (lower)alkanoyloxy or phenyl and Y is amino or a group obtained by reacting the amino group with acetaldehyde, formaldehyde or acetone; fluoro; chloro; bromo; iodo; hydroxy; (lower)alkanoyloxy; carboxy; guanidino; 3-guanyl-1-ureido; 3-(2-furoyl)ureido; 3-benzoylureido; sulfo; sulfoamino; ureido; thioureido; (lower)alkoxy; cyano; cyanamino; or indanyloxycarbonyl.

The most preferred compounds of this subclass are those in which Ar' is phenyl, p-hydroxyphenyl, 4-hydroxy-3, 5-dichlorophenyl, 3-chloro-4-hydroxyphenyl, o-, m- or p-aminomethylphenyl, 2-thienyl, 3-thienyl, 1-cyclohexenyl or 1,4-cyclohexadienyl and Y is amino, hydroxy or carboxy.

A most preferred subclass within this group consists of the compounds wherein R is an acyl group of the formula

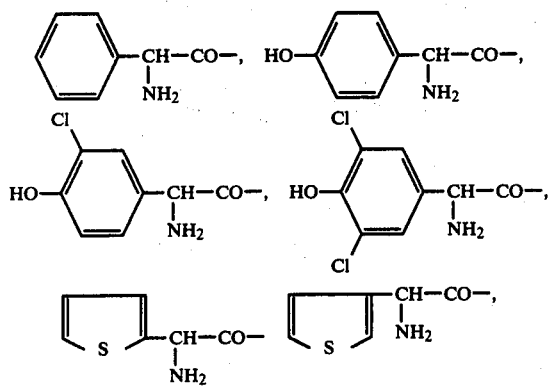

-continued

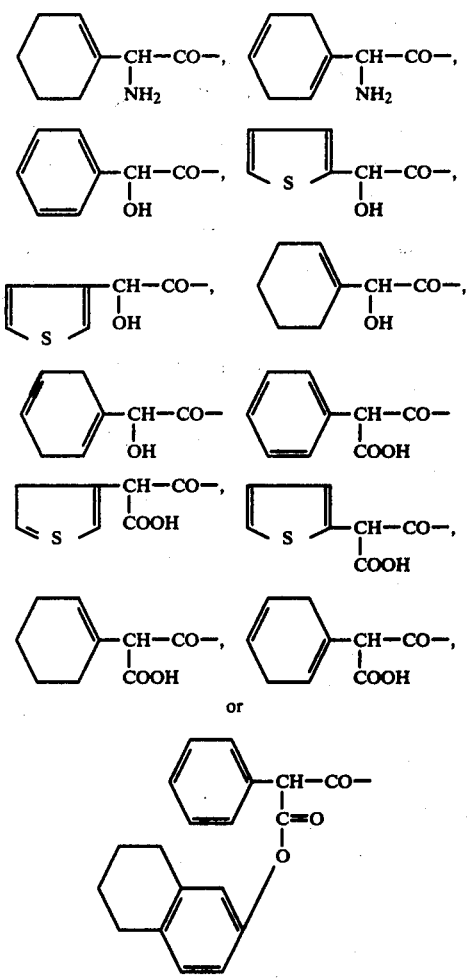

A most preferred subclass within this group consists of the compounds wherein R is an acyl group of the formula

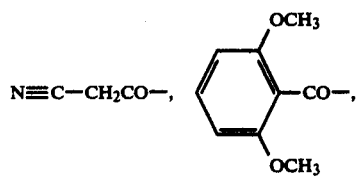

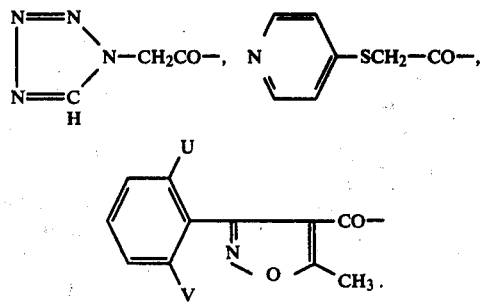

wherein U and V are alike or different and each is hydrogen, chloro or fluoro;

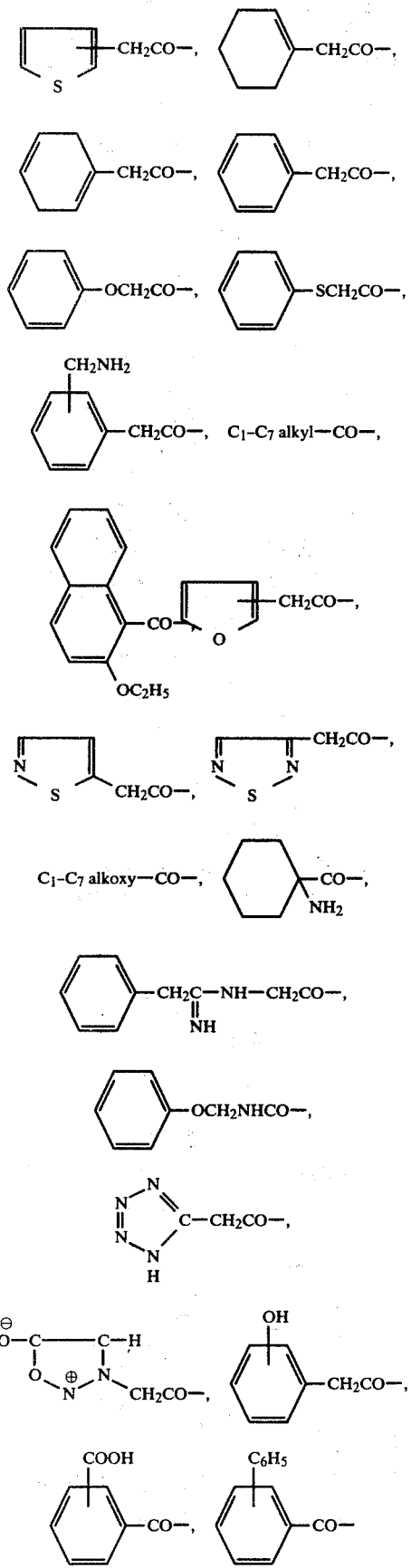

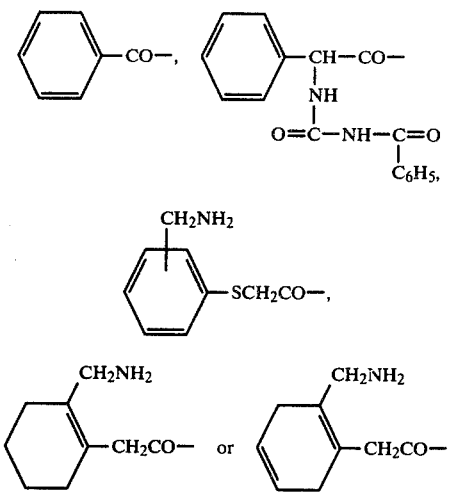

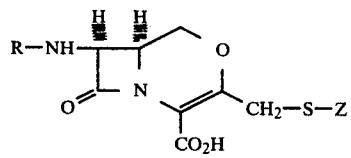

A most preferred subclass within this group consists of the acids in which R is a-carboxyphenylacetyl, cyanoacetyl, α-amino-α-(p-hydroxyphenyl)-acetyl, α-amino-α-(3-chloro-4-hydroxyphenyl)acetyl, α-amino-α-(3,5-dichloro-4-hydroxyphenyl)acetyl, α-amino-α-(2-thienyl)acetyl, α-amino-α-(3-thienyl)acetyl, α-amino-α-(1-cyclohexenyl)acetyl, α-amino-α-(1,4-cyclohexadienyl)acetyl, α-hydroxyacetyl, α-hydroxy-α-(2-thienyl)acetyl, α-hydroxy-α-(3-thienyl)acetyl, α-hydroxy-α-(1-cyclohexenyl)acetyl, α-hydroxy-α-(1,4-cyclohexadienyl)acetyl, α-carboxy-α-(2-thienyl)acetyl, α-carboxy-α-(3-thienyl)acetyl, α-carboxy-α-(1-cyclohexenyl)acetyl, α-carboxy-α-(1,4-cyclohexadienyl)-acetyl, α-indanyloxycarbonyl-α-phenylacetyl, 1-(1H)-tetrazolyl, 4-pyridylthioacetyl, 2-thienylacetyl, 3-thienylacetyl, 1-cyclohexenylacetyl, 1,4-cyclohexadienylacetyl, α-aminomethylphenylacetyl, 1-aminocyclohexylcarbonyl, 2,6-dimethoxybenzoyl, sydnoneacetyl or α-azidophenylacetyl, and pharmaceutically acceptable salts thereof.

A most preferred subclass within this group consists of the D-isomers of the acids in which R is α-amino-α-(p-hydroxyphenyl)acetyl, α-amino-α-(3-chloro-4-hydroxyphenyl)acetyl, α-amino-α-(3,5-dichloro-4-hydroxyphenyl)acetyl, α-amino-α-(2-thienyl)acetyl, α-amino-α-(3-thienyl)acetyl, α-amino-α-(1-cyclohexenyl)acetyl, α-amino-α-(1,4-cyclohexadienyl)acetyl, α-hydroxyacetyl, α-hydroxy-α-(2-thienyl)acetyl, α-hydroxy-α-(3-thienyl)acetyl, α-hydroxy-α-(1-cyclohexenyl)acetyl or a α-hydroxy-α-(1,4-cyclohexadienyl)acetyl, or pharmaceutically acceptable salts thereof.

Another preferred embodiment of the present invention consists of the compounds of formula

II wherein R is an acyl group and Z is a triazole, thiadiazole, oxadiazole or tetrazole radical, said radical being optionally substituted by one or more substituents selected from halo, $C_1$–$C_4$ alkyl, $C_1$–$C_4$ alkoxy, cyano, carboxyl, amino, nitro, $C_3$–$C_4$ cycloalkyl, $C_2$–$C_4$ alkenyl, trifluoromethyl, hydroxy, hydroxymethyl, $C_1$–$C_4$ alkylthio, $C_1$–$C_4$ alkylamino, di ($C_1$–$C_4$ alkyl)amino, phenyl, benzyl, mercapto, alkoxyalkyl of up to 4 carbons or —$(CH_2)_nCOOH$ in which n is an integer of 1 to 4, and easily cleavable esters and pharmaceutically acceptable salts thereof.

A most preferred embodiment of the present invention consists of the compounds of formula II in which Z is 1,2,3-triazol-5-yl, 2-methyl-1,3,4-thiadiazol-5-yl, 2-methyl-1,3,4-oxadiazol-5-yl, 1-N-methyltetrazol-5-yl, 1-carboxymethyltetrazol-5-yl or 1-carboxyethyltetrazol-5-yl.

A preferred subclass within this group consists of the compounds in which R is

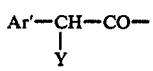

in which Ar' is a radical of the formula

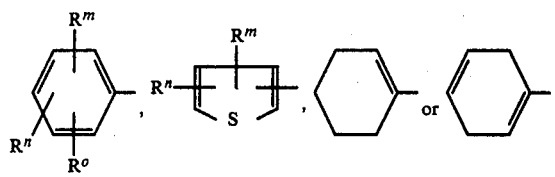

in which $R^m$, $R^n$ and $R^o$ are alike or different and each is hydrogen, hydroxy, (lower)alkyl, cyano, (lower)alkoxy, chloro, bromo, iodo, fluoro, trifluoromethyl, nitro, amino, (lower)alkylamino, di(lower)alkylamino, (lower)alkanoyl, (lower)alkanoyloxy or phenyl and Y is amino or a group obtained by reacting the amino group with acetaldehyde, formaldehyde or acetone; fluoro; chloro; bromo; iodo; hydroxy; (lower)alkanoyloxy; carboxy; guanidino; 3-guanyl-1-ureido; 3-(2-furoyl)ureido; 3-benzoylureido; sulfo; sulfoamino; ureido; thioureido; (lower)alkoxy; cyano; cyanamino; or indanyloxycarbonyl.

The most preferred compounds of this subclass are those in which Ar' is phenyl, p-hydroxyphenyl, 4-hydroxy-3,5-dichlorophenyl, 3-chloro-4-hydroxyphenyl, o-, m- or p-aminomethylphenyl, 2-thienyl, 3-thienyl, 1-cyclohexenyl or 1,4-cyclohexadienyl and Y is amino, hydroxy or carboxy.

Another preferred subclass within this group consists of the compounds wherein R is an acyl group of the formula

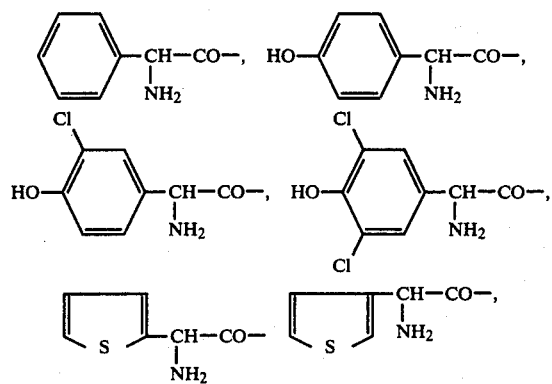

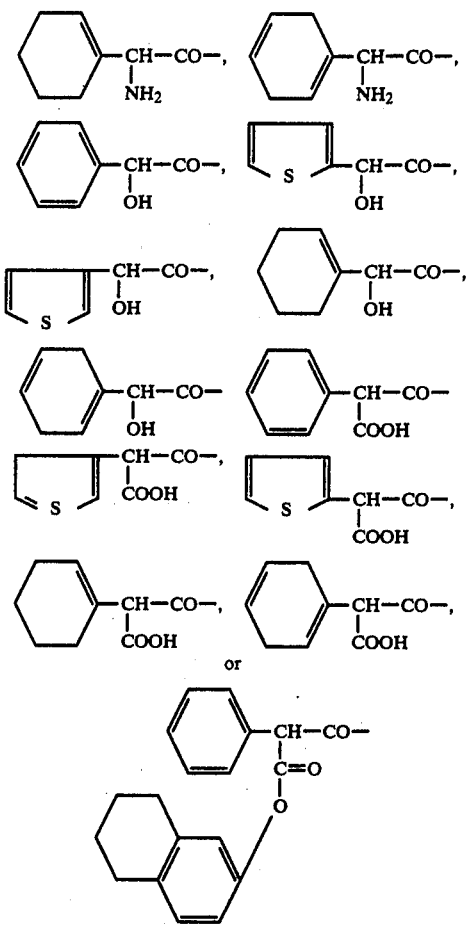

Another preferred subclass within this group consists of the compounds in which R is an acyl group of the formula

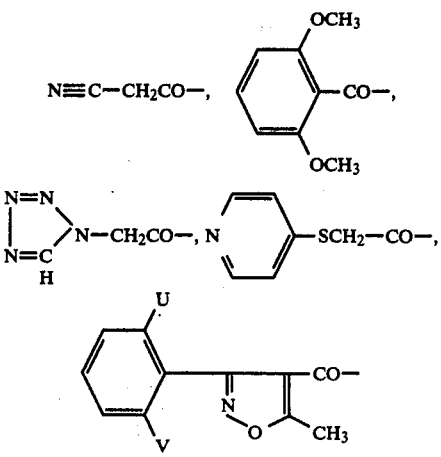

wherein U and V are alike or different and each is hydrogen, chloro or fluoro;

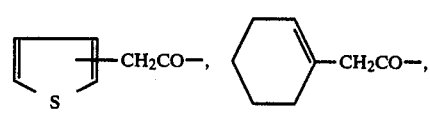

-continued

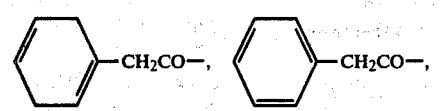

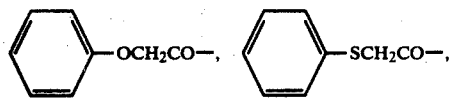

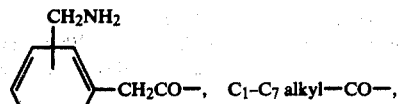, C₁-C₇ alkyl—CO—,

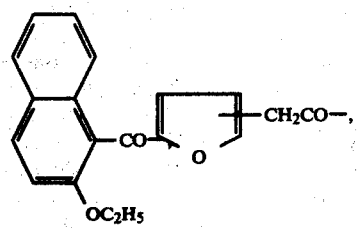

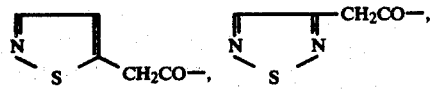

C₁-C₇ alkoxy—CO—, 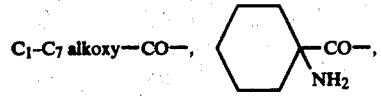

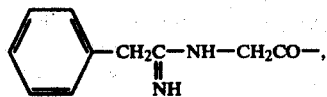

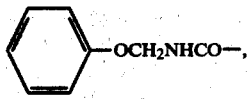

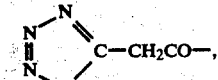

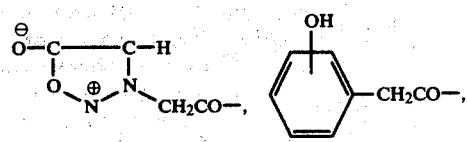

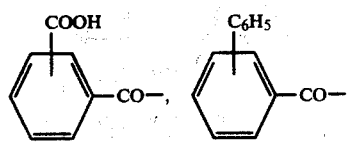

-continued

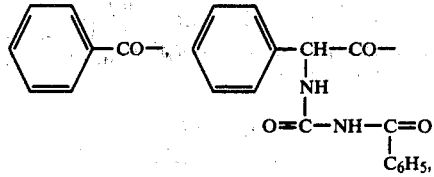

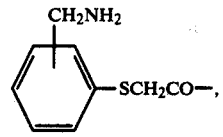

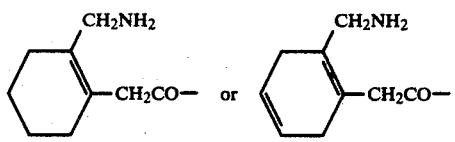

Another preferred subclass within this group consists of the acids in which R is α-carboxyphenylacetyl, cyanoacetyl, α-amino-α-(p-hydroxyphenyl)-acetyl, α-amino-α-(3-chloro-4-hydroxyphenyl)acetyl, α-amino-α-(3,5-dichloro-4-hydroxyphenyl)acetyl, α-amino-α-(2-thienyl)acetyl, α-amino-α-(3-thienyl)acetyl, α-amino-α-(1-cyclohexenyl)acetyl, α-amino-α-(1,4-cyclohexadienyl)acetyl, α-hydroxyacetyl, α-hydroxy-α-(2-thienyl)acetyl, α-hydroxy-α-(3-thienyl)acetyl, α-hydroxy-α-(1-cyclohexenyl)acetyl, α-hydroxy-α-(1,4-cyclohexadienyl)acetyl, α-carboxy-α-(2-thienyl)acetyl, α-carboxy-α-(3-thienyl)acetyl, α-carboxy-α-(1-cyclohexenyl)acetyl, α-carboxy-α-(1,4-cyclohexadienyl)-acetyl, α-indanyloxycarbonyl-α-phenylacetyl, 1-(1H)-tetrazolyl, 4-pyridylthioacetyl, 2-thienylacetyl, 3-thienylacetyl, 1-cyclohexenylacetyl, 1,4-cyclohexadienylacetyl, o-aminomethylphenylacetyl, 1-aminocyclohexylcarbonyl, 2,6-dimethoxybenzoyl, sydnoneacetyl or α-azidophenylacetyl, or pharmaceutically acceptable salts thereof.

Another preferred subclass within this group consists of the D-isomers of the acids in which R is α-amino-α-(p-hydroxyphenyl)acetyl, α-amino-α-(3-chloro-4-hydroxyphenyl)acetyl, α-amino-α-(3,5-dichloro-4-hydroxyphenyl)acetyl, α-amino-α-(2-thienyl)acetyl, α-amino-α-(3-thienyl)acetyl, α-amino-α-(1-cyclohexenyl)-acetyl, α-amino-α-(1,4-cyclohexadienyl)acetyl, α-hydroxyacetyl, α-amino-α-(2-thienyl)acetyl, α-hydroxy-α-(3-thienyl)acetyl, α-hydroxy-α-(1-cyclohexenyl)acetyl or α-hydroxy-α-(1,4-cyclohexadienyl)acetyl, or pharmaceutically acceptable salts thereof.

The present invention further provides various novel intermediates useful in the synthesis of the 7-acylamido 0-2-isocephem compounds of formula II described above.

Preferred embodiments of the present invention are the novel intermediates having the formula

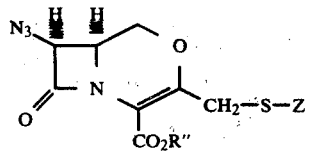

IV wherein Z is optionally substituted $C_1$–$C_6$ alkyl, aryl, aralkyl or heterocyclic and R" is hydrogen or an easily cleavable ester carboxyl-protecting group, and salts thereof. The preferred Z substituents are as defined above in connection with the compounds of formulae I and II.

Other preferred embodiments of the present invention are the intermediates having the formula

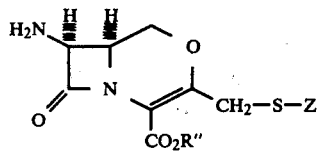   III wherein Z is optionally substituted $C_1$–$C_6$ alkyl, aryl, aralkyl or heterocyclic and R" is hydrogen or an easily cleavable ester carboxyl-protecting group, and salts thereof. The preferred Z substituents are those mentioned above as being preferred in connection with the compounds of formulae I and II.

The intermediates of formulae III and IV may be in the form of the free carboxylic acid or a salt thereof or in the form where the carboxyl group is protected in a conventional manner such as preferably by esterification. The protecting group is selected so that it may be removed by methods which do not result in any appreciable destruction of the remaining portion of the molecule. Preferred carboxyl protecting groups are the easily cleavable esters as defined above including in particular benzhydryl, p-nitrobenzyl, trichloroethyl, silyl including especially trimethylsilyl, phenacyl, p-methoxybenzyl, acetonyl, (lower)alkyl such as methyl, t-butyl or ethyl, benzyl, triphenylmethyl, methoxymethyl, acetoxymethyl, phthalidyl, indanyl and pivaloyloxymethyl.

The novel 7-acylamido compounds of formula II may be prepared by N-acylating a 7-amino intermediate of the formula

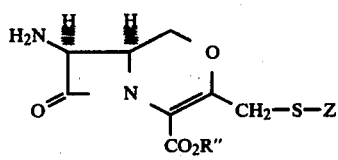   III wherein Z is optionally substituted $C_1$–$C_6$ alkyl, aryl, aralkyl or heterocyclic and R" is hydrogen or an easily cleavable ester carboxyl-protecting group, or a salt thereof, with an acylating acid of the formula

R—COOH wherein R is an acyl group, or with its functional equivalent as an acylating agent for a primary amine and, if desired, (a) when R" is a carboxyl-protecting group, converting the 7-acylated ester to the free acid compound or a physiologically hydrolyzed ester or a pharmaceutically acceptable salt of said acid or ester, or (b) when R" is hydrogen, converting the 7-acylated carboxylic acid to a physiologically hydrolyzed ester or a pharmaceutically acceptable salt of said acid or ester and, if desired, resolving a resulting isomer mixture into its component isomers.

The 7-amino starting materials of general formula III are of use primarily as intermediates in preparing the pharmacologically active N-acyl derivatives of formula II. The free acids, physiologically hydrolyzed esters and pharmaceutically acceptable salts of said acids and esters of formula III, however, do possess some antibacterial activity per se against various pathogenic microorganisms.

The 7-acylamido 0-2-isocephem compounds of formula II are prepared by N-acylation according to known methods of the 7-amino group of intermediate III with an acylating acid of the formula

R—COOH wherein R is an acyl group, or with its functional equivalent as an acylating agent for a primary amino group. The acylating agents for preparing the products of formula II are known, readily preparable by known methods or described herein.

Intermediate III may be acylated either in the form of the free carboxylic acid (or salt thereof) or as an easily cleavable ester (or acid addition salt thereof). Preferred esters include benzhydryl, benzyl, p-nitrobenzyl, trichloroethyl, silyl (especially trimethylsilyl), phenacyl, p-methoxybenzyl, acetonyl, (lower)alkyl including particularly methyl, ethyl and t-butyl, triphenylmethyl, methoxymethyl, acetoxymethyl, pivaloyloxymethyl, phthalidyl and indanyl. The procedures for preparing esters of carboxylic acids are disclosed in the literature and are well-known to those skilled in the art of penicillin and cephalosporin chemistry. Methods for preparing certain of the more preferred easily cleavable esters, i.e. the pivaloyloxymethyl, acetoxymethyl, methoxymethyl, acetonyl and phenacyl esters, are disclosed in U.S. Pat. No. 3,284,451 and in U.K. Pat. No. 1,229,453. Preparation of phthalidyl esters of penicillins and cephalosporins is described in South African patent applications Nos. 72/3799 and 72/3800. The free acid form of intermediate III may also be converted to a silyl ester, e.g. trimethylsilyl ester, as by the methods described in the literature, e.g. U.S. Pat. No. 3,249,622. The silyl ester carboxyl-protecting group may be easily removed following the acylation reaction by hydrolysis or alcoholysis.

Prior to the acylation reaction, any reactive substituents on the acylating acid or derivative thereof, e.g. hydroxy, carboxyl or mercapto, may be protected by use of suitable protecting or blocking groups which are well-known to those skilled in the art of β-lactam chemistry, e.g. as by acylation or silylation. When the acylating agent contains an amino functional group in the acyl moiety, the amino group is protected by a conventional amino-blocking group which may be readily removed at the conclusion of the reaction. Examples of suitable amino-protecting or blocking groups include t-butoxycarbonyl, carbobenzyloxy, 2-hydroxy-1-naphthcarbonyl, trichloroethoxycarbonyl, 2-ethoxycarbonyl-1-methylvinyl and 2-methoxycarbonyl-1-methylvinyl. A particularly valuable amino-blocking group is a proton, as in the acylating agent of the formula

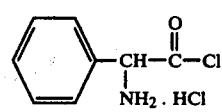

Preferred amino-protecting groups are t-butoxycarbonyl, carbobenzyloxy, the proton and a β-diketone or β-ketoester as in U.K. Pat. No. 1,123,333 or U.S. Pat. Nos. 3,325,479 and 3,316,247, e.g. methyl acetoacetate, or a β-ketoamide as in Japan Pat. No. 71/24714. When the t-butoxycarbonyl, carbobenzyloxy, β-ketoester, β-diketone or β-ketoamide protecting groups are employed, it is preferred to convert the acylating acid containing the blocked amino group to a mixed anhydride, e.g. with ethyl or isobutyl chloroformate, before reaction with compound III or a salt thereof. After the acylation coupling reaction, the amino-protecting group and any other functional protecting groups used may be removed by methods known per se to form the desired product of formula II. With respect to amino-protecting groups, the t-butoxycarbonyl group may be removed by use of formic acid, the carbobenzyloxy group by catalytic hydrogenation, the 2-hydroxy-1-naphthcarbonyl group by acid hydrolysis, the trichloroethoxycarbonyl group by treatment with zinc dust in glacial acetic acid, the proton by neutralization, etc.

Acylation of a free amino group of a cephalosporin or penicillin nucleus is a well-known reaction, and any of the functional equivalents of the carboxylic acid RCOOH commonly used in penicillin or cephalosporin chemistry as acylating agents for primary amino groups may be employed in acylating intermediate III. Examples of suitable acylating derivatives of the free acid include the corresponding acid anhydrides, mixed anhydrides (e.g. alkoxyformic anhydrides), acid halides, acid azides, active esters and active thioesters. The free acid may be coupled with compound III after first reacting said free acid with N,N'-dimethylchloroformininium chloride [cf. Great Britain 1,008,170 and Novak and Weichet, Experientia XXI, 6, 360(1965)] or by the use of enzymes or of an N,N'-carbonyldiimidazole or an N,N'-carbonylditriazole [cf. South African Pat. Specification No. 63/2684] or a carbodiimide reagent [especially N,N'-dicyclohexylcarbodiimide, N,N'-diisopropylcarbodiimide or N-cyclohexyl-N'-(2-morpholinoethyl)carbodiimide: cf. Sheehan and Hess, J.A.C.S., 77, 1967 (1955)], or of alkylylamine reagent [cf. R. Buijle and H. G. Viehe, Angew. Chem. International Edition, 3, 582, (1964) or of an isoxasolium salt reagent [cf. R. B. Woodward, R. A. Olofson and H. Mayer, J. Amer. Chem. Soc., 83, 1010 (1961)], or of a ketenimine reagent [cf. C. L. Stevens and M. E. Munk, J. Amer. Chem. Soc., 80, 4065 (1958] or of hexachlorocyclotriphosphatriazine or hexabromocyclotriphosphatriazine (U.S. 3,651,050) or of diphenylphosphoryl azide [DPPA; J. Amer. Chem. Soc., 94, 6203-6205 (1972)] or of diethylphosphoryl cyanide [DEPC; Tetrahedron Letters No. 18, pp. 1595-1598)] or of diphenyl phosphite [Tetrahedron Letters No. 49, pp. 5047-5050 (1972)]. Other examples of suitable amide coupling reagents which have been described in the literature include (CH₃)₂SCH₂CCHBr/DMSO (J. Chem. Soc. (C) 1904 (1969), HCCOCH₃ (Rec. Trav. Chim. 74, 769 (1955), (CH₃)₂C(OCH₃)₂ (Chim. Ther. 2, 195 (1967), SiCl₄ (J. Org. Chem. 34, 2766 (1969), TiCl₄ (Can. J. Chem. 48, 983 (1970), (PNCl₂)₃ (J. Org. Chem. 33, 2979 (1968), SO₃·DMF (J. Org. Chem. 24, 368 (1959), ion exchange resins (Helv. 44, 1546 (1961) and J.C.S. C, 874 (1969) and

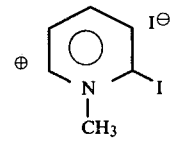

(J. Chem. Soc. 4650 (1964). An equivalent of the acid chloride is the corresponding azolide, i.e., an amide of the corresponding acid whose amide nitrogen is a member of a quasi-aromatic five membered ring containing at least two nitrogen atoms, i.e., imidazole, pyrazole, the triazoles, benzimidazole, benzotriazole and their substituted derivatives. As an example of the general method for the preparation of an azolide, N,N'-carbonyldiimidazole is reacted with a carboxylic acid in equimolar proportions at room temperature in tetrahydrofuran, chloroform, dimethylformamide or a similar inert solvent to form the carboxylic acid imidazolide in practically quantitative yield with liberation of carbon dioxide and one mole of imidazole. Dicarboxylic acids yield diimidazolide. The by-product, imidazole, precipitates and may be separated and the imidazolide isolated, but this is not essential. A preferred acylating agent for preparing 7-acylamido compounds containing an α-amino substituent, e.g. α-aminobenzyl, α-amino-α-thienylmethyl, etc. is the N-carboxy anhydride (Leuch's anhydride). In this structure the group which activates the carboxyl group also serves to protect the amino group. Another preferred acylating agent for introducing a side chain containing an α-amino functional group is the acid chloride hydrochloride, of the formula

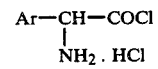

which also serves a dual function of carboxyl activation and amino protection. Mention was made above of the use of enzymes to couple the free acid with compound III. Included in the scope of such processes are the use of an ester, e.g. the methyl ester, of that free acid with enzymes provided by various micro-organisms, e.g. those described by T. Takahashi et al., J.A.C.S., 94(11), 4035-4037 (1972) and by T. Nara et al., J. Antibiotics (Japan) 24(5), 321-323 (1971) and in U.S. Pat. No. 3,682,777. A particularly preferred coupling agent for coupling the acylating acid with compound III (or a salt or ester thereof) is N-ethoxycarbonyl-2-ethoxy-1,2-dihydroquinoline (EEDQ) as described in J.A.C.S., 90, 823-824 and 1652-1653 (1968) and U.S. Pat. No. 3,455,929.

The particular process conditions, e.g. temperature, solvent, reaction time, etc. selected for the coupling reaction are determined by the nature of the reactants and acylation method used and are known to those skilled in the art.

The acylating agents which may be used to form the N-acyl compounds of formula II are known in the literature along with methods for their synthesis or are disclosed in the examples which follow. In those cases where the acylating agent contains one or more asymmetric carbon atoms and thus exists in optically active forms, the compounds obtained using such an acylating agent are ordinarily obtained in racemic form. When the separate optical isomers are desired, the acylating agent can be resolved in a conventional manner such as by reacting the free acid with cinchonine, strychnine, brucine or the like, fractionally crystallizing to separate the diastereoisomeric salts and separately acidifying the solid phase and the liquid phase to liberate the optical isomers.

The 7-acylamido compounds of the present invention may be isolated in any of the ways customarily employed for the isolation of corresponding cephalosporin compounds. Formation of a desired pharmaceutically acceptable carboxylic acid or acid addition salt is carried out by known methods, e.g. reaction of the acid of compound II (or ester in the case of acid addition salts) with an appropriate base or acid.

A compound of formula II in the form of the free acid or a salt thereof may be converted to a pharmaceutically acceptable salt thereof or to a physiologically hydrolyzed ester or pharmaceutically acceptable salt thereof. Similarly, the product of formula II in the form of an easily cleavable ester or salt thereof may be converted to the free acid product or a pharmaceutically acceptable salt thereof by removal of the esterifying group to form the free acid, e.g. by acidic or alkaline hydrolysis, by enzymatic hydrolysis (as with human or animal serum), by hydrogenolysis or by treatment with chemical reagents known to remove particular blocking groups, e.g. sodium thiophenoxide as in U.S. Pat. No. 3,284,451, and subsequent treatment of the free acid with an acid or base to form a pharmaceutically acceptable salt.

The easily cleavable esters of the compounds of formula II are useful as intermediates in the production of the free acid product. The pivaloyloxymethyl, acetoxymethyl, phthalidyl, indanyl and methoxymethyl esters are also useful as active antibacterial agents since on oral administration they are rapidly hydrolyzed to the active metabolite. These esters are of particular interest because they provide on oral administration different rates and amounts of absorption and give differing concentrations of the active antibacterial agent in blood and tissues.

The 7-amino intermediates of general formula III may be prepared by selectively reducing a 7-azido intermediate of the formula

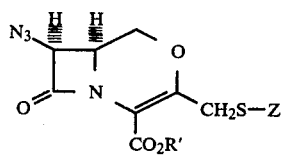

wherein Z is optionally substituted $C_1$-$C_6$ alkyl, aryl, aralkyl or heterocyclic and R'' is an easily cleavable ester carboxyl-protecting group. The carboxyl-protected compound may, if desired, be cleaved to produce the free-acid intermediate III which can be converted to a salt by methods known per se.

Preferred reducing agents for use in preparing the intermediates of formula III include chemical reducing agents such as zinc and ammonium chloride, aluminum amalgam and hydrogen sulfide in the presence of a base, e.g. triethylamine or ammonia. Catalytic hydrogenation may also be employed with such catalysts as noble metals, preferably platinum or palladium including derivatives thereof such as oxides, hydroxides and halides, or Raney nickel, said catalysts being optionally supported on a conventional carrier such as carbon or diatomaceous earth. Catalytic hydrogenation is performed with a non-reducible inert solvent, e.g. methanol, ethanol or ethyl acetate, and preferably at atmospheric or slightly elevated pressure at room temperature.

Compound III in the carboxyl-protected form or a salt thereof may be used directly as a starting material in the N-acylation process discussed above. Alternatively, the protected intermediate may be de-blocked to form the free carboxylic acid which may then be optionally converted to a salt or to another carboxyl-protected form, e.g. a physiologically hydrolyzed ester or salt thereof. By proper selection of reduction conditions and protecting groups, azido intermediate IV' may be converted either simultaneously or in stepwise fashion to the 7-amino free acid III. Thus, if mild hydrogenation conditions are used, e.g. catalytic hydrogenation with 10% Pd-on-charcoal or a mild chemical reducing agent such as $H_2S$ in the presence of a base such as triethylamine or ammonia, the azido group may be reduced without concomitant removal of esters resistant to such conditions, e.g. benzyl or p-nitrobenzyl. If stronger reducing conditions are used such as 30% Pd-on-diatomaceous earth, both the azido group and most reducible esters will be simultaneously reduced.

A preferred embodiment of the present invention is the process comprising the consecutive steps of (1) selectively reducing a 7-azido intermediate of the formula IV' to produce a carboxyl-protected 7-amino intermediate of formula III and, if desired, removing the carboxyl-protecting group to produce the corresponding free acid intermediate of formula III or optionally a salt thereof; and (2) N-acylating intermediate III or a salt thereof with an acylating acid of the formula R-COOH where R is an acyl group, or with its functional equivalent as an acylating agent for a primary amine and, if desired, (a) when R'' is a carboxyl-protecting group, converting the 7-acylated ester to the free acid compound or a physiologically hydrolyzed ester or a pharmaceutically acceptable salt of said acid or ester, or (b) when R'' is hydrogen, converting the 7-acylated carboxylic acid to a physiologically hydrolyzed ester or a pharmaceutically acceptable salt of said acid or ester and, if desired, resolving a resulting isomer mixture into its component isomers.

The 7β-azido intermediates IV' may be prepared by two alternative methods. In one procedure a dihalide intermediate of the formula

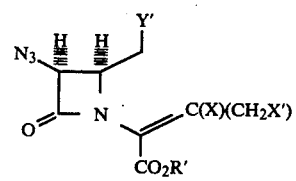

wherein Y' represents a displaceable leaving group, preferably a group such as halo or sulfonyloxy, e.g., alkyl- or substituted alkylsulfonyloxy or aryl- or substituted arylsulfonyloxy, and most preferably a group selected from halo, $-OSO_2-$(lower)-alkyl including especially $-OSO_2CH_3$, $-OSO_2CF_3$ and $-O-SO_2C_6H_4CH_3$(para), X and X' which may be the same or different each represent a halogen atom, preferably bromine or iodine and most preferably iodine and R' is an easily cleavable ester carboxyl-protecting group is reacted in an inert organic solvent in the presence of an acid acceptor with a nucleophile of the formula

Z—SH wherein Z is optionally substituted $C_1$-$C_6$ alkyl, aryl, aralkyl or heterocyclic, or a salt thereof, to form a thiolated intermediate of the formula

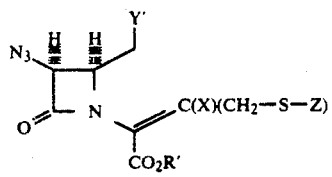

VI

Intermediate VI is then converted to the desired 7β-azido compound by cyclization with base in an inert organic solvent.

The dihalide starting material V may be used in either of its isomeric forms

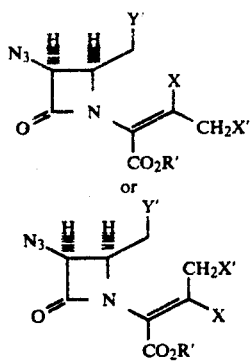

Va or

Vb or as a mixture of isomers. Formula V above is intended to represent either of the individual isomers or the mixture. Any dihalide including a mixed dihalide, e.g. X=Cl, X'=Br, may be used but the most preferred compound is the diiodide. Compound V is reacted in an inert organic solvent, e.g., methylene chloride, with the desired thiol or a salt thereof. Since an acid HX is given off during the reaction, an acid acceptor, preferably an organic base such as pyridine or a trialkylamine, is used. Compound V, the thiol and the acid acceptor are preferally employed in approximately equimolar amounts. The temperature for the displacement step is not critical, but best results are obtained at room temperature or below, most preferably at a temperature of about 0° C.

Cyclization of intermediate VI is carried out in an inert organic solvent, preferably a polar organic solvent such as dimethylsulfoxide or dimethylformamide, with a suitable base. The base used in the cyclization step may be selected from a wide variety of bases including especially those of the following categories:

(a) anions derived from carboxylic acids having a $pK_a$ of between about 3.5 and 5.5;

(b) tertiary organic amines such as a trialkylamine (e.g., triethylamine), pyridine, n-methylpiperidine, n-methylmorpholine, etc.;

(c) alkali metal hydrides, e.g., sodium or potassium hydride; and (d) organolithium compounds including especially lithium alkyls, e.g., methyl, lithium or butyl lithium.

Most preferred cyclization bases are acetate and formate anions, e.g., from alkali metal, ammonium or substituted ammonium formates or acetates. The most preferred base is acetate anion. The base is preferably used in a molar excess relative to compound VI. While the preferred temperatures for this step are room temperature or below, the temperature is not critical. The leaving group Y' in formula VI should be one which is efficiently displaced under the conditions of the base cyclization reaction and is preferably halo (chloro, bromo, fluoro, or iodo) or sulfonyloxy. The most preferred leaving group is the mesylate group.

Preparation of intermediate V is described in U.S. application Ser. No. 567,323 filed Apr. 11, 1975 and also in the text below under the heading "Preparation of Starting Materials." Briefly summarized, the reaction scheme is as shown in Flow Sheet I below:

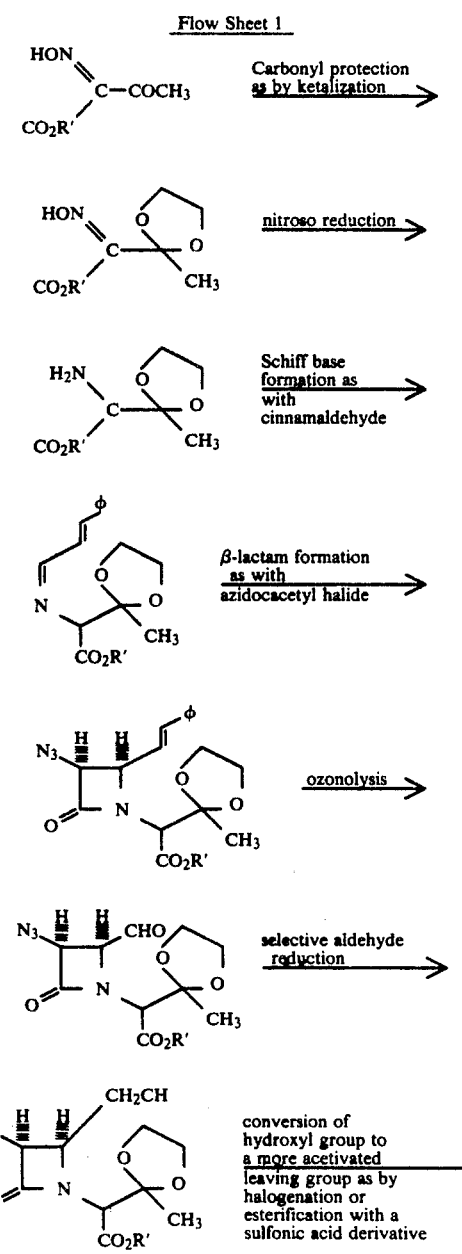

-continued
Flow Sheet 1

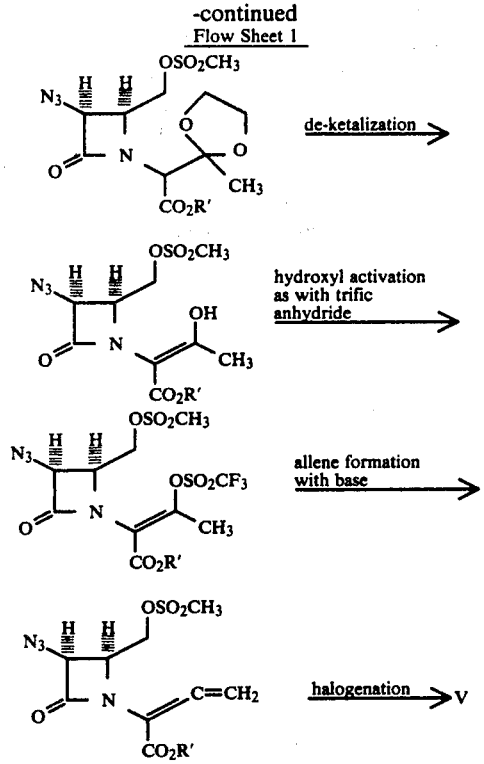

An alternative method for preparing the 7β-azido intermediates of formula IV' involves reacting an intermediate of the formula

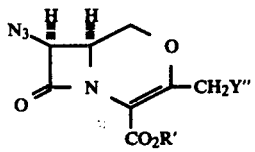   VII wherein Y" represents a displaceable leaving group and R' is an easily cleavable ester carboxyl-protecting group in an inert organic solvent in the presence of an acid acceptor with a thiol of the formula

HS—Z wherein Z represents an optionally substituted $C_1-C_6$ alkyl, aryl, aralkyl or heterocyclic group, or a salt thereof.

Leaving group Y" in formula VII may be any nucleophilic group which is displaceable by the thiol. Examples of suitable leaving groups include halo (chloro, bromo, fluoro or iodo) and sulfonyloxy, i.e., alkyl- or substituted alkylsulfonyloxy or aryl- or substituted arylsulfonyloxy. Preferred leaving groups are halo, —OSO₂—(lower)alkyl including expecially —OSO₂CH₃, —OSO₂CF₃ and —OSO₂C₆H₄CH₃(para). A most preferred leaving group is the mesylate group.

The nucleophilic displacement reaction is conducted in an inert organic solvent, e.g., methylene chloride, in the presence of an acid acceptor, preferally an organic base such as pyridine or a trialkylamine. The heterocyclic thiol, acid acceptor and intermediate VII are preferally used in approximately equimolar quantities. The temperature is not critical, but best results are obtained at room temperature or below, most preferably at a temperature of about 0° C.

The preferred starting materials of formula VII i.e., Y"= halo or sulfonyloxy, used in the above process are disclosed and claimed in U.S. Pat. application Ser. No. 567,323 filed Apr. 11, 1975; the entire method of preparation of these starting materials involves the steps of (1) cyclizing in an inert organic solvent, e.g., dimethylformamide, a dihalide intermediate of formula V with a base $R_2COO^-$ in which $R_2$ in hydrogen or (lower) alkyl to produce an intermediate of the formula

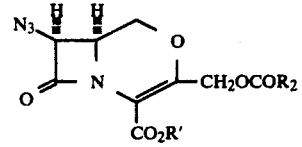

in which $R_2$ is hydrogen or (lower) alkyl and;

(2) subjecting said intermediate to acid hydrolysis to produce an intermediate of the formula

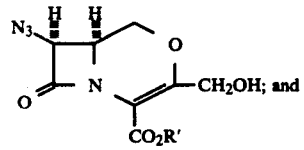

either (a) esterifying the 3-hydroxymethyl intermediate with a sulfonic acid derivative, e.g., methanesulfonyl chloride, p-toluenesulfonyl chloride or triflic anhydride, in the presence of an organic base and in an inert organic solvent, e.g., methylene chloride, to produce the desired 3-sulfonyloxy derivative of formula VII; or (b) halogenating the 3-hydroxymethyl intermediate with a phosphorus halide, e.g., phosphorus trichloride, or phosphorus tribromide, to produce the desired 3-halomethyl derivative of formula VII.

The present invention also provides an alternative method for preparing the novel 7-acylamido compounds of formula II; which process comprises reacting in an inert organic solvent in the presence of an acid acceptor a 7-acylated compound of the formula

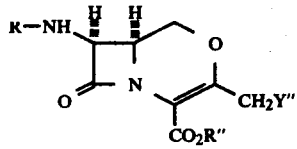   VIII wherein R is an acyl group, Y" is a displaceable leaving group and R" is hydrogen or an easily cleavable ester carboxyl-protecting group, or a salt thereof, with a thiol of the formula

HS—Z wherein Z is optionally substituted $C_1-C_6$ alkyl, aryl, aralkyl or heterocyclic, or a salt thereof and, if desired, (a) when R" is a carboxyl-protecting group, converting the 7-acylated ester to the free acid compound or a physiologically hydrolyzed ester or a pharmaceutically acceptable salt of acid acid or ester, or (b) when R" is hydrogen, converting the 7-acylated carboxylic acid to a physiologically hydrolyzed ester or a pharmaceutically acceptable salt of said acid or ester; and, if desired, resolving a resulting isomer mixture into its component isomers.

The nucleophilic displacement of the Y group in compound VIII may be carried out using the same general reaction conditions, i.e., solvents, temperature range, acid acceptors, as described above in connection with thiolation of compound V.

The 7-acylated starting materials for the above process may be prepared by the procedures disclosed in U.S. Pat. application Ser. No. 567,323 filed Apr. 11, 1975. While Y" may be any nucleophilic leaving group which is displaceable by the desired thiol, the preferred starting materials are compounds wherein Y" is halo (chloro, bromo, iodo or fluoro) or sulfonyloxy, i.e., alkyl- or substituted alkylsulfonyloxy or aryl- or substituted arylsulfonyloxy. Examples of preferred leaving groups include halo, —OSO₂—(lower)alkyl, —O-SO₂CF₃ and —OXO₂C₆H₄CH₃(para). A most preferred leaving group is the mesylate group.

Starting materials of formula VIII may be prepared from 7β-azido compounds of formula VII by the consecutive steps of (1) Selectively reducing intermediate VII as by catalytic hydrogenation with a noble metal catalyst, e.g., 10% Pd-on-charcoal, or by use of chemical reducing agents such as zinc and ammonium chloride, aluminum amalgam or hydrogen sulfide in the presence of a base such as ammonia or triethylamine to produce a 7-amino intermediate of the formula

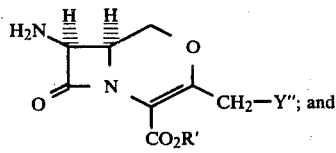

(2) N-acylating said 7-amino intermediate or a salt thereof with an acylating acid of the formula

R—COOH wherein R is an acyl group, or with its functional equivalent as an acylating agent for a primary amine, and, if desired, converting the carboxyl-protected 7-acylamino compound to the corresponding free acid or to a salt thereof as by the methods disclosed above in connection with the de-blocking of compound II.

The pharmaceutically active compounds of the present invention are potent antibacterial agents useful in the treatment of infectious diseases in poultry and animals, including man, caused by many Gram-positive and Gram-negative bacteria. The active compounds are also of value as nutritional supplements in animal feeds and as agents for the treatment of mastitis in cattle.

The novel medicaments provided by the present invention may be formulated as pharmaceutical compositions comprising, in addition to the active ingredient, a pharmaceutically acceptable carrier or diluent. The compounds may be administered both orally and parenterally. The pharmaceutical preparations may be in solid form such as capsules, tablets or dragees, or in liquid form such as solutions, suspensions or emulsions. In the treatment of bacterial infections in man, the active compounds of this invention may be administered parenterally or orally in an amount of from about 5 to 200 mg/Kg/day and preferably about 5 to 20 mg/Kg/day in divided dosage, e.g. three or four times a day. They are administered in dosage units containing, for example, 125, 250 or 500 mg. of active ingredient with suitable physiologically acceptable carriers or excipients.

Illustrative examples of the preparation of starting materials and compounds of the present invention follow. These examples are given in illustration of, but not in limitation of, the present invention. All temperatures are in degrees Centigrade. DMF represents dimethylformamide, THF stands for tetrahydrofuran and EEDQ is the amide bond forming reagent having the structure

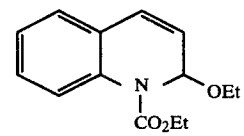

The β-lactam compounds prepared in the examples which follow all have the hydrogen atoms at carbons 6 and 7 cis with respect to each other and, unless indicated, the products are racemic mixtures in the sense that they are composed of equal parts of the two isomers having the following structures:

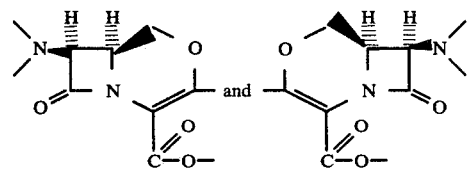

PREPARATION OF STARTING MATERIALS

Preparation 1

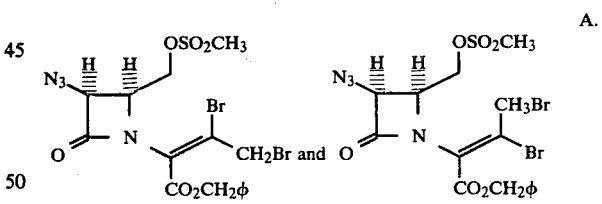

Benzyl Oximino-Acetoacetate

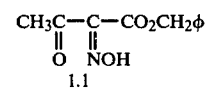

1.1

The procedure was essentially the same as that used to make the corresponding ethyl ester by H. Adkins and J. Reeve, JACS 60, 1328 (1938).

In a three necked one liter flask fitted with a thermometer, a dropping funnel and a magnetic stirrer were placed 173 g. (0.9 mole) of benzyl acetoacetate [The benzyl acetoacetate was prepared as described by Baker et al., J. Org. Chem. 17, 91 (1952)] and 130 ml. of glacial acetic acid. The contents were cooled in an ice bath and a solution of 69 g. (1 mole) of sodium nitrite in 130 ml. of water was added over a period of half an hour; the temperature was kept at 0° to 10° C. After the reaction mixture was stirred for one hour at room temperature, 400 ml. of water was added and the stirring was continued for an additional two hours. The reaction mixture was extracted three times with 200 ml. portions of diethyl ether. The diethyl ether extracts were combined, washed once with water, three times with saturated sodium bicarbonate solution and once with brine. After drying over anhydrous sodium sulfate, the diethyl ether solution was evaporated leaving [1.1] as a clear oil which solidified upon trituration with petroleum ether (30°–60°) to give 186.5 g. (93.2%) of white solid. Its NMR spectrum was consistent with the assigned structure. Generally the product was used as such in subsequent reaction but it can be recrystallized from toluene, m.p. 81°–82° C.

Benzyl Oximino-Acetoacetate Ethylene Ketal

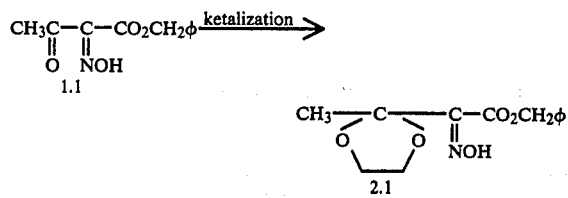

In a two liter flask fitted with a Dean Stark water separator and a condenser were placed in 186.5 g. (0.85 mole) of benzyl oximino-acetoacetate [1.1], 62 g. (1 mole) of ethylene glycol, 800 ml. of benzene (reagent grade) and 2 g. (10.5 mmole) of p-toluenesulfonic acid monohydrate. The reaction mixture was boiled at reflux until 15 ml. of water was removed (3 hours). The benzene solution was washed once with saturated sodium bicarbonate solution and once with brine. After drying over anhydrous sodium sulfate, the benzene solution was evaporated, leaving 212 g. (94% yield) of benzyl oximino-acetoacetate ethylene ketal [2.1] as a light yellow oil! Its NMR spectrum was consistent with the assigned structure. Generally, the product was used as such in subsequent reactions but one of the isomers can be crystallized[2] from toluene-petroleum either (b.p. 30°–60° C.); m.p. 52° C.

Anal. Calc'd for $C_{13}H_{15}NO_5$: C, 58.86; H, 5.70; N, 5.28. Found: C, 58.97; H, 5.68; N, 5.12.

1. A mixture of the syn and anti isomers.
2. Only 35% of the oil could be crystallized.

Benzyl Amino-Acetoacetate Ethylene Ketal

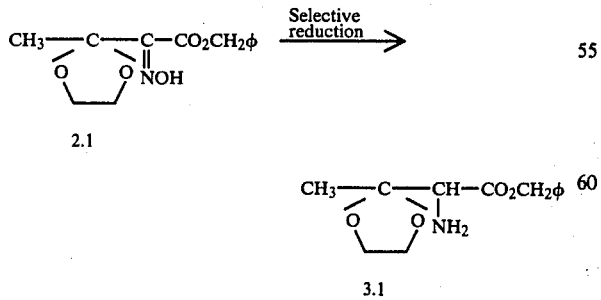

Freshly prepared aluminum amalgam[1] (from 27 g. of aluminum foil) in a three-necked one liter flask was covered with 500 ml. of diethyl ether. The flask was fitted with a mechanical stirrer, a condenser, and a dropping funnel. A solution of benzyl oximino-acetoacetate ethylene ketal [2.1] (132.5 g.; 0.5 mole) in 300 ml. of wet diethylether[2] was added dropwise at such a rate as to maintain boiling at reflux. After stirring for four hours, the reaction mixture was filtered through a Buchner funnel. The filtrate was evaporated leaving 110 g. of yellowish oil. The oil was dissolved in 800 ml. of dry diethylether and dry hydrogen chloride gas was bubbled into the solution until no further precipitation occurred. The white precipitate was filtered off and washed once with diethylether and then dried in vacuo. This provided 108 g. of benzyl aminoacetoacetate ethylene ketal hydrochloride[3] [3.1]; m.p. 157°–158° C.

Anal. Calc'd. for $C_{13}H_{17}NO_4 \cdot HCl$: C, 54.26; H, 6.31; N, 4.87. Found: C, 53.96; H, 6.19; N, 4.60.

To obtain the free base, the hydrochloride salt was suspended in 500 ml. of diethylether and concentrated ammonium hydroxide was added with shaking until the solid went into solution. The diethylether layer was separated and washed twice with brine. After drying over anhydrous sodium sulfate, the solvent was evaporated leaving 90 g. (71% yield) of colorless oil.

1. The aluminum amalgam was prepared essentially as described in A. I. Vogel ("Practical Organic Chemistry," 3rd, Edn., Longemans Green & Co., London, (1957), p. 198) except for the following modification:
   (a) 5% NaOH was used.
   (b) The second washing with ethanol was omitted.
   (c) Dry diethylether was used for washing and most of the water must be drained.
2. The diethylether was saturated with water by shaking with water in a separatory funnel.
3. The product can be stored as the hydrochloride salt.

Schiff Base Formation And β-Lactam Formation

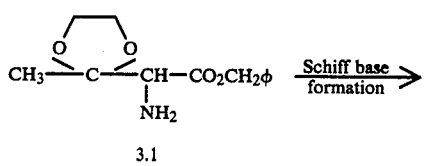

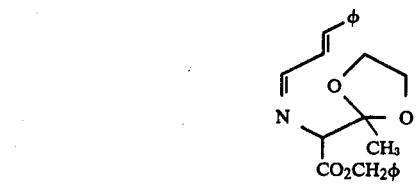

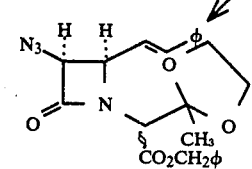

In a one liter flask fitted with a Dean Stark water separator and a condenser were placed 70.3 g. (0.28 mole) benzyl aminoacetoacetate ethylene ketal [3.1], 37 g. (0.28 mole) cinnamaldehyde, and 750 ml. of methylene chloride (reagent grade). The mixture was boiled at reflux for 30 minutes and then 400 ml. of methylene chloride were distilled off. The concentrated solution was then dried over anhydrous sodium sulfate and then evaporated to dryness in vacuo[1]. The residual oil was checked by NMR to ensure that Schiff base formation was complete before continuing on to the next step.

The freshly prepared Schiff base [4.1] was diluted with 600 ml. of methylene chloride[2] and cooled to 0° C. (ice-salt bath). Triethylamine (31.1 g.; 0.308 mole) was added and then a solution of 36.2 g. (0.308 mole) of azidoacetyl chloride[3] in 362 ml. of methylene chloride[2] was added dropwise at 0° C. over a period of one hour. The reaction mixture was stirred for an additional hour at room temperature[4] and then evaporated on a rotary evaporator at reduced pressure while being heated on a 35° C. water bath[5]. The residue was diluted with 500 ml. of diethylether and filtered. The filtrate was washed twice with brine and dried over anhydrous sodium sulfate. Evaporation of this solution yielded 117.5 g. (94% yield) of styryl β-lactam[5.1]. Its NMR and IR spectra are consistent with the assigned structure and indicate the presence of a mixture of isomers, diasteriomeric at the carbon α to the carbonyl of the benzyl ester.

1. This evaporation must be done to ensure complete Schiff base formation.
2. All the methylene chloride used in the cycloaddition reaction as reagent grade which was first dried over molecular sieve (Type 4A) and then over anhydrous calcium chloride. It was stored thereafter over molecular sieve (Type 4A).
3. J. H. Boyer and J. Horner, J. Amer. Chem. Soc., (1955), 77, 951.
4. The reaction mixture can be kept overnight at 0° if necessary.
5. This operation is necessary to ensure complete β-lactam formation.

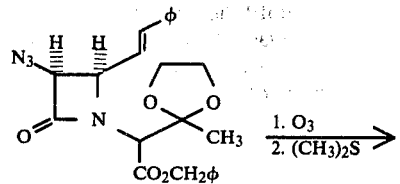

5.1

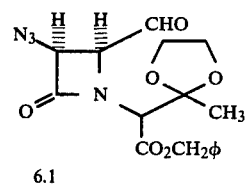

6.1

Styryl β-lactam [5.1] (117.5 g.; 0.262 mole) was dissolved in one liter of methylene chloride (reagent grade), cooled to −50° to −60° C. in a dry ice-acetone bath, and ozonized until a faint blue-green color appeared. The solution was then flushed with nitrogen until the color faded. Methylsulfide (100 ml.) was added to the −50° C. solution, which was then allowed to slowly reach 25° as the cooling bath gradually melted. It was kept overnight at room temperature under nitrogen and then it was washed twice with 1% sodium bicarbonate solution, twice with brine, dried over anhydrous sodium sulfate, and evaporated to dryness. The resulting oil triturated four times with 100 ml. portions of petroleum ether (b.p. 30°-60° C.) to remove benzaldehyde. The oil was then triturated carefully with diethylether whereupon it solidified. The solid was filtered off and dried to provide 75 g. (71.5%) of aldehyde [6.1] as a mixture of isomers diasteriomeric at the carbon γ to the carbonyl of the benzyl ester. Recrystallization of [6.1] from ether gave white crystals, m.p. 101°-102° C. (corrected).

Anal. Calc'd. for $C_{17}H_{18}N_4O_6$: C, 54.54; H, 4.84; N, 14.96. Found: C, 54.75; H, 4.87; N, 14.89.

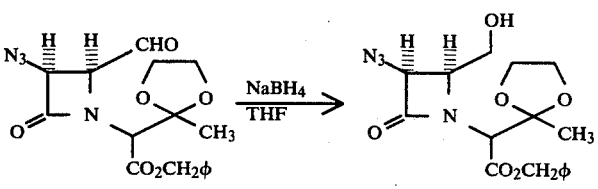

6.1          7.1

Conversion of hydroxyl group to more active leaving group as by esterification with methanesulfonyl halide

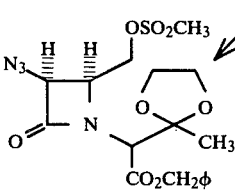

8.1

The aldehyde [6.1] (116.3 g., 0.31 mole) was dissolved in 600 ml. of THF (reagent grade) and the solution was then cooled to −10° C. (ice-methanol bath). Sodium borohydride (5.88 g.; 0.155 mole) was added and the reaction mixture was stirred 1 hour. 10% aqueous hydrochloric acid was added until the mixture was slightly acidic, then 600 ml. brine was added. The THF layer was separated and the aqueous phase was extracted twice with 250 ml. portions of diethylether. The combined organic phases were washed twice with 400 ml. portions of brine, dried over anhydrous sodium sulfate, and evaporated in vacuo to yield 117.3 g. of crude alcohol [7.1] as an orange oil. This oil was used as such in the next reaction.

A solution of methanesulfonyl chloride (37.8 g.; 0.34 mole) in 100 ml. of methylene chloride[1] was added dropwise at 0° C. (ice-water bath) to a stirring solution of alcohol [7.1] (105.6 g.; 0.28 mole, triethylamine (56.6 g.; 0.34 mole) and one liter of methylene chloride[1]. Afterwards, the reaction was stirred for 30 hours at 25° C. It was then washed twice with brine (500 ml. portions), dried over anhydrous sodium sulfate, and evaporated in vacuo. The resulting oil was dissolved in methylene chloride, treated with norite, and then filtered over approximately 200 g. of activity I silica gel. The silica gel was then washed with approximately 2 liters of methylene chloride. The filtrate was evaporated to dryness and the resulting oil (116 g.) was covered with diethylether. It crystallized on standing to give 87.2 g. (80% from [6.1]) of mesylate [8.1] as off-white solid, m.p. 97°–99° C. (corrected).

1. The methylene chloride used was reagent grade which had been further purified by passing over a column of calcium chloride and then storing over molecular sieve (Type 4A).

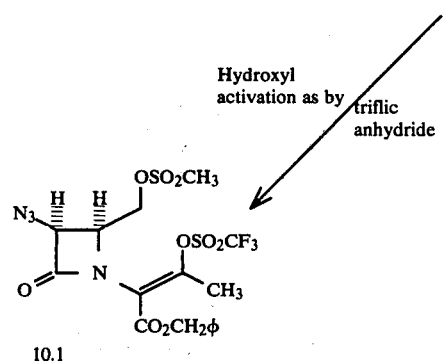

A mixture of mesylate [8.1] (3.19 g.; 6.43 mmole) and 30 ml. of 95% trifluoroacetic acid was stirred at 25° for 2 hours. The mixture was diluted with 300 ml. of brine and extracted three times with methylene chloride (100 ml. portions). The combined extracts were washed three times with water (50 ml. portions, until neutral), dried (anhydrous sodium sulfate) and evaporated to dryness in vacuo leaving 3.17 g. of a brown oil. NMR spectra of this oil indicate the presence of >90% enol [9.1].

Crude enol [9.1] (48.0 g.; 0.117 mole) and triflic anhydride (33.0 g.; 0.117 mole) were dissolved in 500 ml. of methylene chloride and the solution was then cooled to 0° C. (ice-water bath). A solution of triethylamine (11.8 g.; 0.117 mole) in 80 ml. of methylene chloride[2] was added dropwise over a period of 40 minutes. When the addition was complete, the ice-water bath was removed and the mixture was stirred at 25° for 45 minutes. The mixture was then poured into 300 ml. of ice water and washed with cold water until the pH of the washings was approximately 6. The extract was dried (anhydrous sodium sulfate) and evaporated in vacuo to give 54.0 g. of crude triflate [10.1] as a dark red oil. This oil was dissolved in 400 ml. of benzene (USP) and passed through a 1½" pad of activity III silica gel. The pad was washed with 1 l. of benzene. Evaporation of the benzene gave 38.3 g. of a yellow oil. This oil was carefully triturated with 50 ml. of absolute ethanol and then cooled at 0° C. for 2 hours. The resulting white solid was filtered off and dried in vacuo to give 19.5 g. of triflate [10.1] as one isomer, m.p. 57°–59° C. (corrected).

Anal. Calc'd. for $C_{17}H_{17}F_3N_4O_4S_2$: C, 37.67; H, 3.14; N, 10.33; S, 11.82. Found: C, 37.40; H, 3.12; N, 10.43; S, 11.73.

1. Triflic anhydride was prepared as follows: 170 g. (100 ml.) $CF_3SO_3H$ ("Fluorochemic acid" 3M Company) and 135 g. $P_2O_5$ were mixed carefully, shaken well, and stored 18 hours, protected from moisture. The product was distilled from the resulting solid mass using a flame; the fraction boiling 80°–90° C. was collected. Re-distillation of this fraction yielded 119.45 g. (74%) of triflic anhydride boiling 82°–84° C.

2. The methylene chloride used was reagent grade which had been further purified by passing over a column of calcium chloride and then stored over molecular sieve (Type 4A).

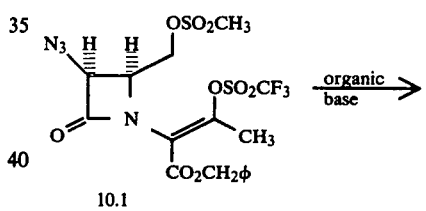

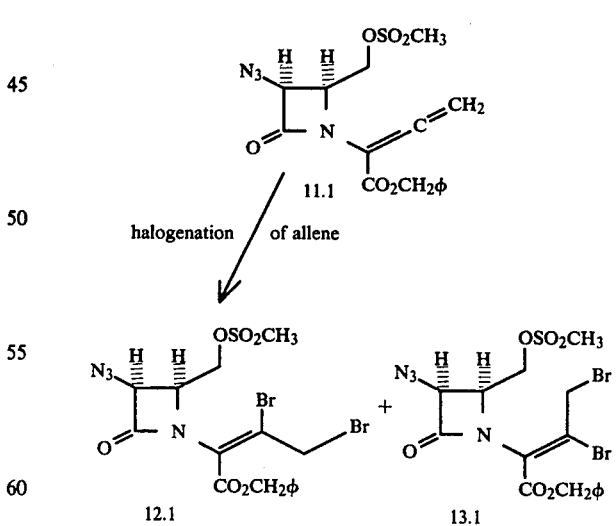

Triethylamine (1 g.; 0.01 mole) was added to a stirred solution of triflate [10.1] (5.42 g.; 0.01 mole) in 55 ml. of methylenechloride (A.R.) at room temperature. After stirring for five minutes (at which point TLC shows complete formation of allene [11.1], a solution of bromine (10 ml. of 1 M solution in $CCl_4$; 0.01 mole) was added dropwise. After addition of the bromine, the mixture was concentrated, absorbed onto Activity I silica gel and dry column chromatographed on Activity I silica gel by eluting with methylene chloride (USP). This yielded one fraction (uniformly one spot by TLC) weighing 2.5 g. (45%). Its IR, UV, and NMR spectra were consistent with the expected dibromide structure [13.1].

Anal. Calc'd. for $C_{16}H_{12}Br_2N_4O_6S$: C, 34.80; H, 2.92; N, 10.15. Found: C, 35.25; H, 2.97; N, 10.02.

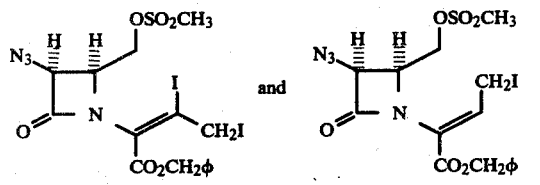

A solution of triethylamine (101 mg., 1.00 mmole) in 1.4 ml. of methylene chloride was added with stirring to a solution of triflate from Preparation 1A above [10.1] (542 mg., 1.00 mmole) in 5.4 ml. of methylene chloride at 0° C. After allowing the solution to warm to 24° over 15 minutes, a solution of iodine (254 mg., 1.00 mmole) in 7.5 ml. of methylene chloride was added with stirring over 30 minutes, then washed with water, dried, decolorized, filtered and the solvent evaporated in vacuo to give the diiodide [23.1] (588 mg.; 91% yield) in greater than 95% purity. The IR and NMR spectra were consistent for the proposed structures.

Anal. Calc'd. for $C_{16}H_{16}N_4O_6I_2S$: C, 29.74; H, 2.50; N, 8.67; I, 39.28; S, 4.96. Found: C, 29.76; H, 2.47; N, 8.61; I, 39.37; S, 5.18.

Other suitable intermediates of general formula V in the specification and claims may be prepared by:

(1) substituting another easily cleavable ester group for the benzyl ester of starting material 1.1; or (2) esterifying compound 7.1 with another sulfonic acid derivative or halogenating compound 7.1; or (3) halogenating allene 11.1 with a halogenating agent other than bromine or iodine, e.g. BrCl.

Preparation 2 p-Nitrobenzyl 7β-azido-3-methylsulfonyloxymethylΔ³-O-2-isocephem-4-carboxylate

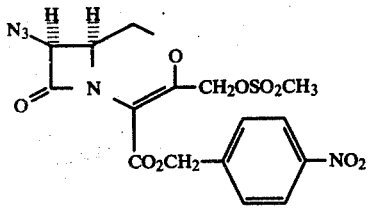

A solution of methanesulfonyl chloride (0.50 ml., 6.5 mmole) in 10 ml. of methylene chloride was added dropwise with stirring to a solution of p-nitrobenzyl 7β-azido-3-hydroxymethyl-Δ³-0-2-isocephem-4-carboxylate (2.41 g., 6.43 mmole), triethylamine (0.97 ml., 7.0 mmole) and 75 ml. of methylene chloride at −10°. After ½ hour at −10° and 1 hour at 24°, the solution was washed with 5% hydrochloric acid, 2% sodium bicarbonate, and water (85 ml. each), then the solvent was evaporated in vacuo to give the mesylate title product, 2.86 g. (98% yield), as a yellow foam. The NMR of the product was in agreement with the proposed structure.

The p-nitrobenzyl 7β-azido-3-hydroxymethyl-Δ³-O-2-isocephem-4-carboxylate starting material used above may be prepared as follows:

1. The diiodide intermediate of the formula

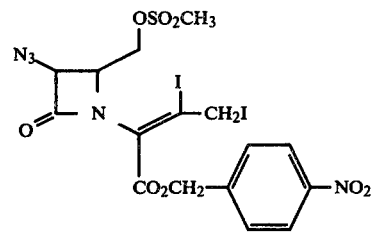

was prepared from p-nitrobenzyl acetoacetate according to the procedures of Preparation 1A and B (Starting Materials) described above.

2. The diiodide intermediate (6.6 g., 9.6 mmole) was cyclized with potassium formate (2.54 g., 30 mmole) in a solution of 100 ml. DMF and 0.1 ml. water at 0°. After stirring for 5 hours with the cooling bath removed, the mixture was poured into 100 ml. of cold water and extracted with methylene chloride. After washing with water containing a little NaCl, drying and evaporation in vacuo, p-nitrobenzyl 7β-azido-3-formyloxymethyl-Δ³-O-2-isocephem-4-carboxylate was recovered (5.3 g.) as a brown oil.

3. To a solution of 5.3 g. of the 3-formyloxymethyl intermediate in 53 ml. of acetone was added 26 ml. of water and 3.2 ml. of 12 M HCl. The mixture was stirred at 24° for 7 hours, then poured into 100 ml. water and extracted with methylene chloride. The combined extracts were washed with water containing a little sodium chloride, dried and evaporated in vacuo to give 3.6 g. of a brown oil. The oil was absorbed from methylene chloride onto 18 g. of silica gel and placed on a 72 g. silica gel column (grade 3, 5% ether). The column was eluted with 200 ml. of ether, then with ether/ethyl acetate 3:1. The major component (Rf 0.20) gave, on evaporation of the solvent in vacuo, a yellow solid which was recrystallized from acetone-ether to give the 3-hydroxymethyl starting material of this example, 950 mg. (17.5% yield from the diiodide). m.p. 147°–148°.

Anal. Calc'd. for $C_{15}H_{13}N_5O_7$: C, 48.00; H, 3.49; N, 18.66. Found: C, 48.11; H, 3.61; N, 18.81.

By replacement of the methanesulfonyl chloride in the procedure above with other sulfonic acid derivatives and the p-nitrobenzyl ester with other easily cleavable esters, suitable intermediates may be prepared having the formula

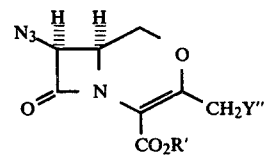

in which Y''' is sulfonyloxy and R' is an easily cleavable ester residue.

Preparation 3

Benzyl 7β-azido-3-bromomethyl-Δ³-O-2-isocephem-4-carboxylate

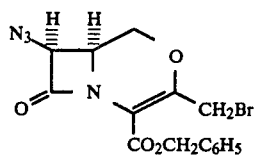

To a solution of benzyl 7β-azido-3-hydroxymethyl-Δ³-O-2-isocephem-4-carboxylate in benzene is added about an equimolar amount of pyridine and a slight molar excess of phosphorous tribromide. There is produced the 3-bromomethyl title product.

The benzyl 7β-azido-3-hydroxymethyl-Δ³-O-2-isocephem-4-carboxylate used above may be prepared by the method disclosed in Preparation 2 by substituting the benzyl ester of the diiodide intermediate for the p-nitrobenzyl ester used therein.

Other suitable 7β-azido-3-halomethyl esters may be prepared by the above method by appropriate variation of the ester acetoacetate starting material and the halogenating agent.

Preparation 4

Benzyl 7β-phenoxyacetamido-3-methyl-sulfonyloxymethyl-Δ³-O-2-isocephem-4-carboxylate

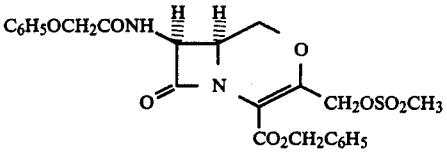

Benzyl 7β-azido-3-methylsulfonyl-oxymethyl-Δ³-O-2-isocephem-4-carboxylate (Preparation 2) is dissolved in methylene chloride and cooled to 0° C. Two equivalents of triethylamine are added and, while stirring and cooling, $H_2S$ gas is passed through the solution until it is saturated. The solution is allowed to come to room temperature and concentrated to give benzyl 7β-amino-3-methylsulfonyl-oxymethyl-Δ³-O-2-isocephem-4-carboxylate.

The ester is reacted with equimolar amounts of phenoxyacetic acid and EEDQ in methylene chloride to give the title product.

Other N-acylated compounds of the formula

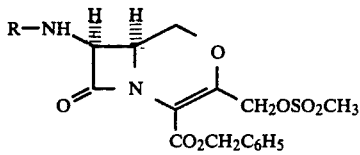

may be prepared by substituting for the phenoxyacetic acid used above another desired acylating agent, preferably one which will produce a starting material in which R is one of the acyl groups mentioned as being preferred in connection with the novel end-products of formula II.

Preparation 5

1-carboxymethyl-1,2,3,4-tetrazole-5-thiol and its di-sodium salt

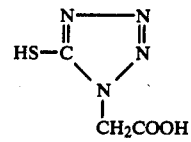

(A) Recrystallization of 1-methyl-5-mercaptotetrazole Procedure:

1. One hundred and ten grams of 1methyl-5-mercaptotetrazole is slurried in 350 ml. of boiling chloroform. A near solution is obtained.

2. The hot solution (50°–60°) is rapidly filtered by vacuum through a heated Buchner funnel (11 cm. SS No. 604 paper containing ¼ to ½ inch of packed filter aid ("Supercel"). The filter pad is washed with 50 ml. of 50°–60° C. chloroform which is added to the filtrate.

3. The filtrate is cooled to approximately 0°–6° C. and kept at 0°–6° C. for 2 hours. The crystals which have formed are collected by filtration at 0°–6° C. and washed with 60 ml. of 0°–6° C. chloroform which is added to the filtrate. The crystals (cut A) are air dried at 37°–45° C. for 18 hours.

4. The filtrate is concentrated on the rotary vacuum evaporator (60° C. bath) to approximately one-half volume. This slurry is cooled to 0°–6° C. and kept at 0°–6° C. for 2 hours. The crystals are collected by filtration at 0°–6° C., washed with 40 ml. of 0°–6° C. chloroform which is added to the filtrate. The crystals (cut B) are air dried at 37°–45° C. for 18 hours. Crystal cuts A and B are composited to give an approximate 65% weight yield.

5. The filtrate of cut B, Step 4 may be reworked twice as described in Step 4 to obtain an additional 15% recovery.

(B) Preparation of 1-carboxymethyl-1,2,3,4-tetrazole-5-thiol and its di-sodium salt 1. Five hundred ml. of substantially dry and pure tetrahydrofuran in a 2-liter 3 neck flask with stirrer is cooled in a salt-acetone-ice bath to approximately −10° C. Dry nitrogen gas is blown on the liquid surface.

2. Five hundred ml. of 15.06% (1.6 N) butyl lithium in hexane (Foote Mineral Co.) is added over a ten minute period under dry nitrogen and stirring to the tetrahydrofuran. The near solution is cooled to −5° to −10° C.

3. Forty six and four tenths gram (46.4 g.) of 1-methyl-5-mercaptotetrazole (recrystallized as above) is dissolved in 200 ml. of substantially pure and dry tetrahydrofuran. The solution is filtered if cloudy and then cooled to 5° to 10° C.

4. The cooled solution of step 3 is added over 10 minutes with stirring and under dry nitrogen to the butyl lithium solution. The temperature should be maintained at −5° C. to +10° C. maximum. Precipitates may form.

5. The mixture is stirred under dry nitrogen and 0° C. to +10° C. for one half hour.

6. Anhydrous carbon dioxide gas is bubbled through at a rapid rate and with rapid stirring for 15–30 minutes at approximately ambient temperature (0° to 10° C.) to no higher than +20° C.

7. The white precipitate which forms is suitably collected by filtration in an area of low humidity. The precipitate is washed with about 75 ml. of tetrahydrofuran.

8. The precipitate is dissolved in 250 ml. of water (pH 8.5-9.5). A second layer of tetrahydrofuran may be present. This may be removed in the vacuum rotary evaporator (50° C. bath).

9. The aqueous solution is adjusted to pH 1.6-2.0 with concentrated hydrochloric acid.

10. The acid aqueous solution is extracted twice with 250 ml. portions of ethyl acetate. Each 250 ml. ethyl acetate extract is back extracted with 100 ml. portions of water. The water extracts are discarded. The ethyl acetate extracts (free of any water layer) are filtered and composited.

11. The combined ethyl acetate extracts are concentrated to dryness on the vacuum rotary evaporator (60° C. bath).

12. The crystals in the flask are boiled with 300 ml. of chloroform for about 2 minutes. The hot slurry (50°-60° C.) is vacuum filtered through a heated Buchner funnel (11 cm-SS-604 paper). The crystals are washed with about 75 ml. of 50° C. chloroform. The crystals are air dried at room temperature for about 3 hours and then made about 100-200 mesh.

13. The 100-200 mesh crystals are treated with boiling chloroform exactly as described in step 12 (the hot chloroform removes most of the unreacted 1-methyl-5-mercaptotetrazole). Yield: approximately 45 to 50 grams of crystalline 1-carboxymethyl-1,2,3,4-tetrazole-5-thiol. These crystals may contain 0.02 to 0.05 moles of 1-methyl-5-mercaptotetrazole.

14. The crystals of step 13 are slurried with 250 ml. of ethyl ether at room temperature for 3-5 minutes. The mixture is filtered. The insolubles (0.5-5%) may be a contaminating symmetrical mercaptotetrazole ketone of the following tentative structure:

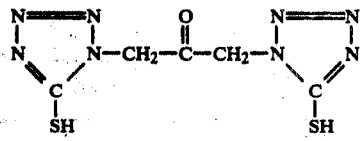

CAUTION: This compound EXPLODES at appproximately 205°-210° C.

15. The ether filtrate of step 14 is evaporated to dryness on the vacumm rotary evaporator (50° C. bath). Approximately 42 to 48 grams of crystalline 1-carboxymethyl-1,2,3,4-tetrazole-5-thiol containing approximately 0.01-0.05 mole of 1-methyl-5-mercaptotetrazole is recovered.

16. The crystals are dissolved in 420 ml. of absolute ethanol (approximately 100 mg./ml.). The solution is warmed to 50°-60° C.

17. To the hot solution of step 16, 310 ml. of a 41% sodium 2-ethylhexanoate (SEH) solution in isopropanol is added with very rapid stirring over a 10 minute period. A crystalline precipitate forms. The mixture is slurried at 50°-60° C. for 20 minutes.

18. The mixture is filtered hot (50°-60° C.) through a heated Buchner funnel (11 cm-SS-No. 604 paper). The crystals are washed with 75 ml. of 50° C. ethanol.

19. The ethanol damp crystals of step 18 are slurried in 200-300 ml. of ethanol. The slurry is passed through a 200 mesh screen. The slurry is heated to 50°-60° C. for 5 minutes with rapid stirring (unreacted di-sodium 1-methyl-5-mercaptotetrazole is very soluble in hot ethanol).

20. The crystals are collected at 50°-60° C. on a 11 cm-SS No. 604 paper in a heated Buchner funnel. The crystals are washed with 75-100 ml. of ethanol and vacuum dried at 50°-60° C. for 24-48 hours. Yield: 40-48 grams of di-sodium 1-carboxymethyl-1,2,3,4-tetrazole-5-thiol (free of 1-methyl-5-mercaptotetrazole as observed by NMR).

PREPARATION 6

1-Carboxyethyl-1,2,3,4-tetrazole-5-thiol

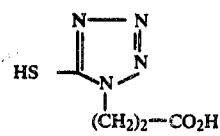

(A) 2-Carboethoxyethylisocyanate

β-alanine ethyl ester hydrochloride (93.6 g.), triethylamine (123.5 g) and methylene chloride (400 ml) were mixed together and cooled to $-10°$ C. Carbon disulfide (46.5 g) dissolved in 150 ml. of chloroform was added to the above solution during a two-hour period while keeping the temperature at about $-10°$ C. After the addition was complete, the temperature was allowed to warm to 10° C. for about 10 minutes. The solution was again cooled to $-10°$ C. and 66.3 g of ethyl chloroformate in 60 ml of chloroform was added dropwise over a 40-minute period with stirring. The temperature was allowed to rise to room temperature for 30 minutes and again cooled to 0° C. an additional 61.6 g of triethylamine was added at 0° C. and then the solution was stirred at room temperature for 3 hours.

The mixture was treated with water and the organic phase collected, washed with 2×250 ml of 2 N HCl, then 2×250 ml of $NaHCO_3$, then 2×250 ml of water. The organic phase was dried over $Na_2SO_4$ and the solvent removed in vacuo to produce 93.7 g of an oil found to be the desired product. The IR and NMR spectra were consistent with the structure.

(B) 1-Carboxyethyltetrazol-5-thiol

Sodium azide (29.7 g) was dissolved in 400 ml of water and heated to 60° C. in a nitrogen atmosphere. 2-Carboethoxyethylisocyanate (46.9 g) dissolved in 50 ml of Skellysolve B (essentially n-hexane) was added to the heated sodium azide solution. The solution was stirred for about 150 minutes at about 70°-72° C., then cooled to 30° C. in an ice bath. 50% sodium hydroxide solution was added until the pH was 12. The mixture was heated for forth minutes at 70° C. and cooled to 15° C. in an ice bath. The pH was adjusted to 2 using conc. Hcl and then extracted with ethyl acetate (4×150 ml). The ethyl acetate extracts were washed with water, then dried over sodium sulfate. The solvent was evaporated in vacuo and the product was collected as crystals from methylene chloride to yield 19.5 g of title product.

Substitution in the procedure for the preparation of 1-carboxyethyltetrazol-5-thiol for the β-alanine ethyl ester used therein of an equimolar quantity of an appropriately substituted amino acid ester of 3 to 4 carbon atoms produces the corresponding 1-carboxy ($C_3-C_4$ alkyl)tetrazol-5-thiol, e.g., 1-carboxypropyltetrazol-5-thiol and 1-carboxybutyltetrazol-5-thiol.

EXAMPLES

EXAMPLE 1 p-Nitrobenzyl 7β-azido-3-(1-methyltetrazol-5-ylthiomethyl)-Δ³-O-2-isocephem-4-carboxylate

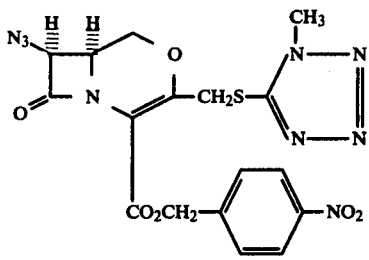

To a solution of p-nitrobenzyl 7β-azido-3-methylsulfonyloxymethyl-Δ³-O-2-isocephem-4-carboxylate (4.53 g., 10 mmole) and triethylamine (1.4 ml., 10 mmole) in 90 ml. of methylene chloride was added 10 mmole of 1-methyltetrazole thiol. The solution was stirred at 24° C. for 16 hours, then washed with 5% HCl and water (100 ml. each), dried and the solvent evaporated in vacuo to give the product as a yellow oil. Upon recrystallization from ethyl acetate, the title product was obtained in 78% yield; m.p. 150°–152° C. The NMR was consistent with the proposed structure.

EXAMPLE 2 p-Nitrobenzyl 7β-azido-3-(2-methyl-1,3,4-thiadiazol-5-ylthiomethyl)-Δ³-O-2-isocephem-4-carboxylate

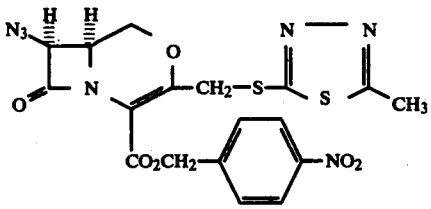

The procedure of Example 1 is repeated except that the 1-methyltetrazole thiol used therein is replaced by 10 mmole of 2-methylthiadiazole thiol. The title product was isolated as a yellow oil in 95% yield. The NMR and IR spectra of the product were in agreement with the proposed structure.

EXAMPLE 3 p-Nitrobenzyl-7β-azido-3-(2-methyl-1,3,4-oxadiazol-5-ylthiomethyl)-Δ³-O-2-isocephem-4-carboxylate

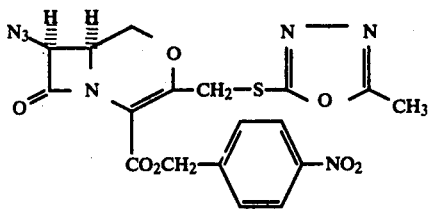

A solution of p-nitrobenzyl 7β-azido-3-methylsulfonyloxymethyl-Δ³-O-2-isocephem-4-carboxylate (1.36 g., 3.0 mmoles) and triethylamine (0.38 ml., 3.0 mmoles) in 50 ml. of dichloromethane was treated with 2-methyl1,3,4-oxadiazole-5-thiol (0.35 g., 3.0 mmoles). The reaction mixture was stirred at room temperature for 48 hours and then washed with 10% HCl, water and brine. The solution was dried over sodium sulfate and evaporated in vacuo giving crude product. The crude product was purified by dry-column chromatography on silica gel (60 g., Activity III) eluting with 15% ethyl acetate in ether. There was obtained 1.0 g. of pure title product in 70% yield. The NMR spectrum was in agreement with the proposed structure.

EXAMPLE 4

If the general procedures of Examples 1–3 are repeated using equimolar weights of 1,2,3-triazole-5-thiol, 1-carboxymethyl-1,2,3,4-tetrazole-5-thiol and 1-carboxyethyl-1,2,3,4-tetrazole-5-thiol, respectively, in place of the thiols used therein, there are produced p-nitrobenzyl 7β-azido-3-(1,2,3-triazol-5-ylthiomethyl)-Δ³-O-2-isocephem-4-carboxylate, p-nitrobenzyl 7β-azido-3-(1-carboxymethyl-1,2,3,4-tetrazol-5-ylthiomethyl)-Δ³-O-2-isocephem-4-carboxylate and p-nitrobenzyl 7β-azido-3-(1-carboxyethyl-1,2,3,4-tetrazol-5-ylthiomethyl)-Δ³-O-2-isocephem-4-carboxylate, respectively.

EXAMPLE 5

Repeating the general procedures of Examples 1–3, p-nitrobenzyl 7β-azido-3-methylsulfonyloxymethyl-Δ³-O-2-isocephem-4-carboxylate is reacted with the thiols listed below to produce the following 7β-azido-3-thiolated compounds.

Product

| Thiol | Z = |
|---|---|
| methyl mercaptan | methyl |
| ethyl mercaptan | ethyl |
| butyl mercaptan | butyl |
| pentyl mercaptan | pentyl |
| 2-aminoethyl mercaptan | 2-aminoethyl |
| 1-chloroethyl mercaptan | 1-chloroethyl |
| 2-hydroxyethyl mercaptan | 2-hydroxyethyl |
| 2-bromoethyl mercaptan | 2-bromoethyl |
| 2-nitroethyl mercaptan | 2-nitroethyl |
| 5-nitropentyl mercaptan | 5-nitrophenyl |
| 3-cyano-n-propyl mercaptan | 3-cyano-n-propyl |
| 4-(dimethylamino)-n-butyl mercaptan | 4-(dimethylamino)-n-butyl |
| 2,3-dihydroxypropyl mercaptan | 2,3-dihydroxypropyl |
| 3-chloro-2-methylbutyl mercaptan | 3-chloro-2-methylbutyl |
| benzenethiol | phenyl |
| p-chlorobenzenethiol | p-chlorophenyl |
| 2,4,5-trichlorobenzenethiol | 2,4,5-trichlorophenyl |
| o-aminobenzenethiol | o-aminophenyl |
| p-bromobenzenethiol | p-bromophenyl |
| p-aminobenzenethiol | p-aminophenyl |
| 2,5-dichlorobenzenethiol | 2,5-dichlorophenyl |
| p-fluorobenzenethiol | p-fluorophenyl |
| m-methoxybenzenethiol | m-methoxyphenyl |
| p-methoxybenzenethiol | p-methoxyphenyl |
| p-nitrobenzenethiol | p-nitrophenyl |
| 2,3,5,6-tetrachlorobenzenethiol | 2,3,5,6-tetrachlorphenyl |

-continued

Product (structure: β-lactam with N3, H, H, CH2, linked to N, O, CH2—S—Z, CO2CH2—C6H4—NO2)

| Thiol | Z = |
|---|---|
| benzyl mercaptan | benzyl |
| p-chlorobenzyl mercaptan | p-chlorobenzyl |
| phenethyl mercaptan | phenethyl |
| p-nitrobenzyl mercaptan | p-nitrobenzyl |
| p-methoxybenzyl mercaptan | p-methoxybenzyl |
| 1-naphthalenethiol | 1-naphthyl |
| 2-naphthalenethiol | 2-naphthyl |
| 4-chloro-1-naphthalene-thiol | 4-chloro-1-napthyl |
| 4-nitro-1-naphthalenethiol | 4-nitro-1-naphthyl |
| 2-thienyl mercaptan | 2-thienyl |
| 3-thienyl mercaptan | 3-thienyl |
| 2-furyl mercaptan | 2-furyl |
| 3-furyl mercaptan | 3-furyl |
| 6-mercaptotetrazolo[4,5-6]pyridazine | tetrazolo[4,5-6]pyridazin-6-yl |
| 3-hydroxy-6-mercapto-pyridazine | 3-hydroxypyridazin-6-yl |
| 6-bromo-3-pyridazinethiol | 6-bromopyridazin-3-yl |
| 3-pyridazinethiol | pyridazin-3-yl |
| 3-methyl-1-phenyl-5-pyrazolethiol | 3-methyl-1-phenylpyrazol-5-yl |
| imidazole-2-thiol | imidazol-2-yl |
| 1-methyl-5-nitro-2-imidazole-thiol | 1-methyl-5-nitroimidazol-2-yl |
| thiazole-2-thiol | thiazol-2-yl |
| 5-methylthiazole-2-thiol | 5-methylthiazol-2-yl |
| oxazole-2-thiol | oxazol-2-yl |
| 5-methyloxazole-2-thiol | 5-methyloxazol-2-yl |
| 2-pyridinethiol | 2-pyridyl |
| 4-pyridinethiol | 4-pyridyl |
| 3-amino-2-pyridinethiol | 3-amino-2-pyridyl |
| 5-nitro-2-pyridinethiol | 5-nitro-2-pyridyl |
| 3-methyl-1-phenyl-5-pyrazolethiol | 3-methyl-1-phenyl-pyrazol-5-yl |
| 2-pyrazinethiol | pyrazine-2-yl |
| 4-pyrimidinethiol | pyrimidin-4-yl |
| 4-methyl-2-pyrimidinethiol | 4-methylpyrimid-2-yl |
| 3-methylisothiazole-5-thiol | 3-methylisothiazol-5-yl |
| isothiazole-5-thiol | isothiazol-5-yl |
| 1,2,3,4-thiatriazole-5-thiol | 1,2,3,4-thiatriazol-5-yl |
| 5-mercapto-3-methylthio-1,2,4-thiadiazole | 3-methylthio-1,2,4-thiadiazol-5-yl |
| 5-mercapto-3-methyl-1,2,4-thiadiazole | 3-methyl-1,2,4-thiadiazol-5-yl |
| 2-mercapto-1,3,4-thiadiazole | 1,3,4-thiadiazol-2-yl |
| 5-mercapto-2-ethyl-1,3,4-thiadiazole | 2-ethyl-1,3,4-thiadiazol-5-yl |
| 5-mercapto-2-n-butyl-1,3,4-thiadiazole | 2-n-butyl-1,3,4-thiadiazol-5-yl |
| 5-mercapto-2-amino-1,3,4-thiadiazole | 2-amino-1,3,4-thiadiazol-5-yl |
| 5-mercapto-2-methylamino-1,3,4-thiadiazole | 2-methylamino-1,3,4-thiadiazol-5-yl |
| 5-mercapto-2-trifluoromethyl-1,3,4-thiadiazole | 2-trifluoromethyl-1,3,4-thiadiazol-5-yl |
| 2-mercapto-5-p-chloro-phenyl-1,3,4-thiadiazole | 5-p-chlorophenyl-1,3,4-thiadiazol-2-yl |
| 3-mercapto-1,2,4-thiadiazole | 1,2,4-thiadiazol-3-yl |
| 5-mercapto-1-butyltetrazole | 1-butyltetrazol-5-yl |
| 5-mercapto-1-phenyl-tetrazole | 1-phenyltetrazol-5-yl |
| 1-benzyl-1H-tetrazole-5-thiol | 1-benzyl-1H-tetrazol-5-yl |
| 5-mercapto-1H-tetrazole | 1H-tetrazol-5-yl |
| 5-mercapto-1-p-chloro-phenyl-1H-tetrazole | 1-p-chlorophenyl-1H-tetrazol-5-yl |
| 2-mercapto-1,3,4-oxa-diazole | 1,3,4-oxadiazol-2-yl |
| 2-mercapto-5-phenyl-1,3,4-oxadiazole | 5-phenyl-1,3,4-oxadiazol-2-yl |

-continued

Product (same structure)

| Thiol | Z = |
|---|---|
| 2-mercapto-5-benzyl-1,3,4-oxadiazole | 5-benzyl-1,3,4-oxadiazol-2-yl |
| 5-mercapto-3-phenyl-1,2,4-oxadiazole | 3-phenyl-1,2,4-oxadiazol-5-yl |
| 2-mercapto-5-ethyl-1,3,4-oxadiazole | 5-ethyl-1,3,4-oxadiazol-2-yl |
| 2-mercapto-5-trifluoromethyl-1,3,4-oxadiazole | 5-trifluoromethyl-1,3,4-oxadiazol-2-yl |
| 1-methyl-5-mercapto-1,2,3-triazole | 1-methyl-1,2,3-triazol-5-yl |
| 1-ethyl-5-mercapto-1,2,3-triazole | 1-ethyl-1,2,3-triazol-5-yl |
| 4-methyl-5-mercapto-1,2,3-triazole | 4-methyl-1,2,3-triazol-5-yl |
| 4-allyl-3-mercapto-1,2,4-triazole | 4-allyl-1,2,4-triazol-3-yl |
| 4-ethyl-3-mercapto-1,2,4-triazole | 4-ethyl-1,2,4-triazol-3-yl |
| 3-mercapto-5-methyl-1,2,4-triazole | 5-methyl-1,2,4-triazol-3-yl |
| 3-mercapto-1,2,4-triazole | 1,2,4-triazol-3-yl |
| 4,5-diethyl-3-mercapto-1,2,4-triazole | 4,5-diethyl-1,2,4-triazol-3-yl |
| 1-cyclopropyl-3-mercapto-1,2,4-triazole | 1-cyclopropyl-1,2,4-triazol-3-yl |
| 3-mercapto-5-methoxymethyl-1,2,4-triazole | 5-methoxymethyl-1,2,4-triazol-3-yl |
| 5-mercapto-3-amino-1,2,4-triazole | 3-amino-1,2,4-triazol-5-yl |

EXAMPLE 6 p-Nitrobenzyl 7β-amino-3-(1-methyltetrazol-5-ylthiomethyl)-Δ³-O-2-isocephem-4-carboxylate

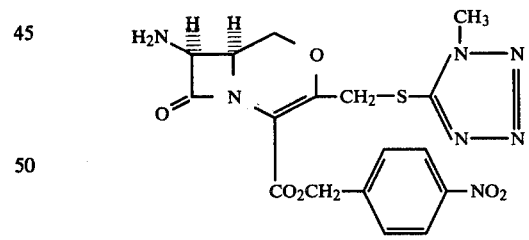

Hydrogen sulfide was slowly passed into a solution of the 7β-azido ester of Example 1 (340 mg., 0.72 mmole) and triethylamine (77 mg., 0.76 mmole) in 10 ml. of methylene chloride for 50 min. One ml. of 10% HCl was added and the mixture concentrated in vacuo. The residue was mixed with 25 ml. methylene chloride and washed with 25 ml. each of 10% NaHCO₃ and dilute NaCl. The methylene chloride solution was dried, treated with charcoal, filtered and evaporated in vacuo. The resulting residue was mixed with methylene chloride, the sulfur filtered off and the solvent evaporated in vacuo to give the title product, 276 mg. (86% yield), as a yellow tar. The IR and NMR spectra were consistent with the proposed structure.

Repeating the above procedure but using the benzyl 7β-azido ester instead of the p-nitrobenzyl ester gave benzyl 7β-amino-3-(1-methyltetrazol-5-ylthiomethyl)-Δ³-O-8c 2-isocephem-4-carboxylate.

EXAMPLE 7 p-Nitrobenzyl 7β-amino-3-(2-methyl-1,3,4-thiadiazol-5-ylthiomethyl)-Δ³-O-2-isocephem-4-carboxylate The procedure of Example 6 is repeated with the p-nitrobenzyl 7β-azido-3-(1-methyltetrazol-5-ylthiomethyl)-Δ³-O-2-isocephem-4-carboxylate used therein replaced by an equimolar weight of p-nitrobenzyl 7β-azido-3-(2-methyl-1,3,4-thiadiazol-5-ylthiomethyl)-Δ³-O-2-isocephem-4-carboxylate. The title product is produced as a yellow solid in 85% yield. The IR and NMR spectra of the product were consistent with the proposed structure.

EXAMPLE 8 p-Nitrobenzyl 7β-amino-3-(2-methyl-1,3,4-oxadiazol-5-ylthiomethyl)-Δ³-O-2-isocephem-4-carboxylate Hydrogen sulfide was bubbled through a solution of the 7β-azido ester of Example 3 (0.99 g., 2.1 mmole) and triethylamine (0.32 ml., 2.3 mmole) in 50 ml. of dichloromethane for 1 min. and the mixture was then stirred for an additional 45 min. Nitrogen was then bubbled through to remove excess H₂S and the solvent was evaporated in vacuo to leave a residue of title product.

EXAMPLE 9

Use of p-nitrobenzyl 7β-azido-3-(1,2,3-triazol-5-ylthiomethyl)-Δ³-O-2-isocephem-4-carboxylate, p-nitrobenzyl 7β-azido-3-(1-carboxymethyl-1,2,3,4-tetrazol-5ylthiomethyl)-Δ³-O-2-isocephem-4-carboxylate and p-nitrobenzyl 7β-azido-3-(1-carboxyethyl-1,2,3,4-tetrazol-5-ylthiomethyl)-Δ³-O-2-isocephem, respectively, in the procedures of Examples 6–8 gives the corresponding p-nitrobenzyl 7β-amino-3-(heterocyclic thiomethyl)-Δ³-O-2-isocephem-4-carboxylates.

EXAMPLE 10

Use of the 7β-azido esters of Example 5 in the procedures of Examples 6–8 gives the corresponding p-nitrobenzyl 7β-amino-3-(alkyl-, aryl-, aralkyl- or heterocyclicthiomethyl)-Δ³-O-2-isocephem-4-carboxylates.

EXAMPLE 11

7β-Amino-3-(1-methyltetrazol-5-ylthiomethyl)-Δ³-O-2-isocephem-4-carboxylic acid

Catalytic hydrogenation of the ester of Example 6 with a 20% palladium hydroxide on carbon catalyst gives the free acid title product.

EXAMPLE 12

Repeating the procedure of Example 11 with the 7β-amino esters of Examples 7–10 gives the corresponding 7β-amino free acid products.

EXAMPLE 13

Pivaloyloxymethyl 7β-amino-3-(1-methyltetrazol-5-ylthiomethyl)-Δ³-O-2-isocephem-4-carboxylate The title compound is produced according to the method of Example 2 of U.K. Specification 1,229,453 by replacing the 7-aminocephalosporanic acid used therein by 7β-amino-3-(1-methyltetrazol-5-ylthiomethyl)-Δ³-O-2-isocephem-4-carboxylic acid.

The respective acetoxymethyl, methoxymethyl, acetonyl and phenacyl esters of 7β-amino-3-(1-methyltetrazol-5-ylthiomethyl)-Δ³-O-2-isocephem-4-carboxylic acid are prepared by substituting in the method above for the chloromethyl pivalate used therein an equimolar weight of chloromethyl acetate, chloromethyl methyl ether, chloroacetone and phenacyl bromide, respectively.

EXAMPLE 14

The procedure of Example 13 is repeated using the 7β-amino carboxylic acids of Example 12 in place of the 7β-amino-3-(1-methyltetrazol-5-ylthiomethyl)-Δ³-O-2-isocephem-4-carboxylic acid used therein. There are produced the corresponding pivaloyloxymethyl esters. Replacement of chloromethyl pivalate by chloromethyl acetate, chloromethyl methyl ether, chloroacetone and phenacyl bromide, respectively, produces the corresponding acetoxymethyl, methoxymethyl, acetonyl and phenacyl esters.

EXAMPLE 15 p-Nitrobenzyl 7β-(2-thienylacetamido)-3-(1-methyltetrazol-5-ylthiomethyl)-Δ³-02-isocephem-4-carboxylate A solution of 2.0 mmole each of p-nitrobenzyl 7β-amino-3-(1-methyltetrazol-5-ylthiomethyl)-Δ³-O-2-isocephem-4-carboxylate, 2-thienyl acetic acid and EEDQ in 20 ml. of methylene chloride was stirred at 24° C. for 2 hours. The resulting solution was washed with 5% NaHCO₃, 10% HCl (2×) and dilute NaCl (20 ml. each), dried and the solvent evaporated in vacuo to give the product as a yellow oil. The product was crystallized from methylene chloride/ether to give the title product in 53% yield; m.p. 165°–168° (dec.). The IR and NMR of the product were consistent with the proposed structure.

EXAMPLE 16 p-Nitrobenzyl 7β-(2-thienylacetamido)-3-(2-methyl-1,3,4-thiadiazol-5-ylthiomethyl)-Δ³-O-2-isocephem-4-carboxylate

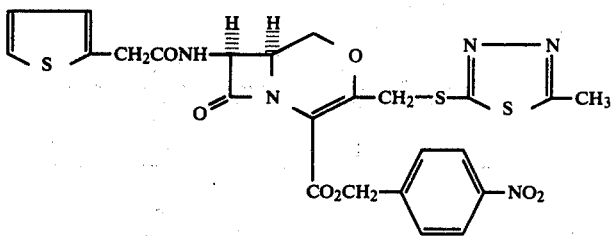

The procedure of Example 15 was repeated with the 7β-amino ester used therein replaced by p-nitrobenzyl 7β-amino-3-(2-methyl-1,3,4-thiadiazol-5-ylthiomethyl)-Δ³-O-2-isocephem-4-carboxylate. The product was absorbed onto 6 g. of silica gel and placed onto a 24 g. column of silica gel. The column was eluted with methylene chloride followed by ethyl acetate. The major fraction was obtained as a yellow foam in 55% yield. Upon recrystallization from methylene chloride/ether, the title product was obtained; m.p. 127°–129° C. The IR and NMR spectra were in agreement with the proposed structure.

Anal. Calc'd. for $C_{24}H_{21}N_5O_6S_3$: C, 49.05; H, 3.60; N, 11.92; S, 16.37. Found: C, 47.42; H, 3.54; N, 11.87; S, 16.20.

EXAMPLE 17 p-Nitrobenzyl 7β-phenoxyacetamido-3-(1-methyltetrazol-5-ylthiomethyl)-Δ³-O-2-isocephem-4-carboxylate

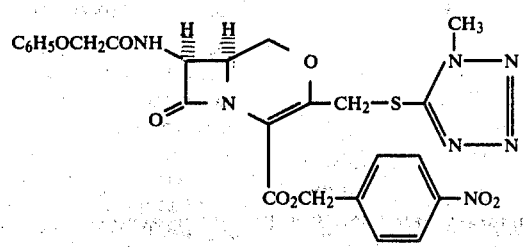

A solution of p-nitrobenzyl 7β-amino-3-(1-methyltetrazol-5-ylthiomethyl)-Δ³-O-2-isocephem-4-carboxylate (270 mg.), EEDQ (150 mg.) and phenoxyactic acid (92 mg.) (0.60 mmole each) in 6 ml. of methylene chloride was maintained at 24° C. for 2 hours. This solution was diluted to 15 ml. with methylene chloride, washed with 5% NaHCO₃ (25 ml.), 10% HCl (2×25 ml.) and saturated NaCl (25 ml.), and then dried and absorbed onto 1.7 g. of silica gel (grade III). The silica gel was placed on a chromatographic column containing 3.4 g. of silica gel (grade III). The column was eluted with ether changing to ether-methylene chloride (1:1) after fraction 4 (all fractions were 5 ml.). TLC of fractions 8–17 showed them to contain one compound (Rf=0.11 on silica gel eluted with ether). These fractions were combined and evaporated in vacuo to give the title product as a yellow tar, 236 mg. (67% yield). The IR and NMR spectra of the product were consistent with the proposed structure.

EXAMPLE 18

Benzyl 7β-phenoxyacetamido-3-(1-methyltetrazol-5-ylthiomethyl)-Δ³-O-2-isocephem-4-carboxylate The procedure of Example 17 was repeated except that the p-nitrobenzyl starting material was replaced by the corresponding benzyl ester. The title product was obtained upon recrystallization from methylene chloride-ether (1:1); m.p. 86°–88° C. U.V. $\lambda_{max}^{MeOH}$ 284 ($\epsilon$=10,400). The NMR and IR spectra of the product were consistent with the proposed structure.

EXAMPLE 19 p-Nitrobenzyl 7β-(2-thienylacetamido)-3-(2-methyl-1,3,4-oxadiazol-5-yl)-Δ³-O-2-isocephem-4-carboxylate

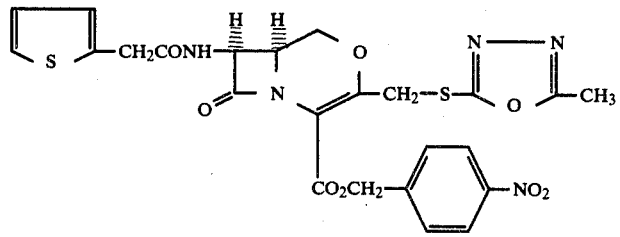

The p-nitrobenzyl ester residue of Example 8 was dissolved in 50 ml. of dichloromethane and treated with 2-thienylacetic acid (0.31 g., 2.2 mmoles) followed by EEDQ (0.54 g., 2.2 mmoles). The mixture was stirred at room temperature for 16 hours and then washed with water, 1% NaHCO₃, water, 10% HCl, water and brine. It was then dried over sodium sulfate and evaporated in vacuo. The residue was purified by dry-column chromatography on silica gel (50 g., activity III) eluting with 25% ethyl acetate in ether to give 0.61 g. of pure title product in 50% yield. The NMR of the product was in agreement with the proposed structure.

EXAMPLE 20

7β-(2-Thienylacetamido)-3-(1-methyltetrazol-5-ylthiomethyl)-Δ³-O-2-isocephem-4-carboxylic acid The p-nitrobenzyl ester from Example 15 (1.00 mmole) in 50 ml. of ethyl acetate and 25 ml. of n-butanol to which 10 ml. of 0.1 M HCl and 500 mg. of 20% palladium hydroxide-on-diatomaceous-earth had been added was hydrogenated on a Parr apparatus at 24° C. and 50 p.s.i. for 3 hours. The catalyst was filtered off and the solution extracted with 1% $NaHCO_3$ (containing some NaCl) (3×25 ml.). The aqueous extract was cooled to 0° C., acidified to pH 1 with 10% HCl and saturated with NaCl. The acidified aqueous was extracted with methylene chloride (4×50 ml.). The methylene chloride was concentrated in vacuo to 100 ml. and after standing, the title product was collected as a colorless solid in 18.5% yield; m.p. 182°–184° (dec.). U.V. $\lambda_{max}^{THF}$ 280 ($\epsilon$=8500). The IR spectrum was consistent with the proposed structure.

Anal. Calc'd. for $C_{16}H_{16}N_6O_5S_2$: C, 44.03; H, 3.70; N, 19.26. Found: C, 44.10, H, 3.71; N, 19.07.

A sample of the title product (called BC-L70) after solution in water and dilution with Nutrient Broth was found to exhibit the following Minimum Inhibitory Concentrations (M.I.C.) in mcg./ml. versus the indicated microorganisms as determined by overnight incubation at 37° C. by tube dilution.

| | | M.I.C. in mcg./ml. | | |
|---|---|---|---|---|
| Organism | | BC-L70 | Cephalexin | Cephalothin |
| D. pneumoniae +5% serum* | A9585 | .016 | .25 | .13 |
| Str. pyogenes +5% serum* | A9604 | .016 | .25 | .06 |
| S. aureus Smith ++ | A9537 | .13 | 1 | .13 |
| S. aureus Smith ++ +50% serum | A9537 | 1 | 1 | .5 |
| S. aureus BX1633-2 at 10⁻³ dil'n | A9606 | .5 | 2 | .25 |
| S. aureus BX1633-2 at 10⁻² dil'n | A9606 | 2 | 4 | .5 |
| S. aureus meth.-resist.; at 10⁻³ dil'n | A15097 | 1 | 8 | 1 |
| Sal. enteritidis ++ | A9531 | .03 | 4 | .5 |
| E. coli Juhl ++ | A15119 | 1 | 8 | 16 |
| E. coli ++ | A9675 | 16 | 8 | 63 |
| K. pneumoniae ++ | A9977 | .25 | 4 | 4 |
| K. pneumoniae ++ | A15130 | 8 | 16 | 16 |
| Pr. mirabilis ++ | A9900 | .13 | 4 | 1 |
| Pr. morganii ++ | A15153 | 32 | 125 | 125 |
| Ps. aeruginosa ++ | A9843A | 125 | 125 | 125 |
| Ser. marcescens ++ | A20019 | 125 | 125 | 125 |
| Ent. cloacae | A9656 | 125 | 125 | 125 |
| Ent. cloacae | A9657 | 1 | 4 | 4 |
| Ent. cloacae | A9659 | 125 | 125 | 125 |

*50% Nutrient Broth - 45% Antibiotic Assay Broth at 10⁻⁴ dilution.

EXAMPLE 21

7β-(2-Thienylacetamido)-3-(2-methyl-1,3,4-thiadiazol-5-ylthiomethyl)-Δ³-O-2-isocephem-4-carboxylic acid The procedure of Example 20 was repeated up to the point of preparing the acidified aqueous extract with the p-nitrobenzyl ester starting material replaced by p-nitrobenzyl 7β-(2-thienylacetamido)-3-(2-methyl-1,3,4-thiadiazol-5-ylthiomethyl)-Δ³-O-2-isocephem-4-carboxylate. The acidified aqueous was extracted with tetrahydrofuran/ethyl acetate (9:1) (2×50 ml.).

The organic extract was washed with saturated NaCl (50 ml.), dried, treated with charcoal and the solvent evaporated in vacuo to give a brown oil. The oil was crystallized from ethyl acetate/ether to give the title product in 39% yield; m.p. 100°–105° C. (dec.). U.V. $\lambda_{max}^{THF/H2O}$ 276 ($\epsilon$=12,500). The IR and NMR were consistent with the proposed structure.

Anal. Calc'd. for $C_{17}H_{16}N_4O_5S_3 \cdot \frac{1}{2} CH_3CO_2C_2H_5$: C, 45.96; H, 4.06; N, 11.29; S, 19.37. Found: C, 45.69; H, 3.97; N, 11.30; S, 19.63.

M.I.C. data for the product (called BC-L71) is shown in the following table.

| | | M.I.C. in mcg./ml. | | |
|---|---|---|---|---|
| Organism | | BC-L71 | Cephalexin | Cephalothin |
| D. pneumoniae +5% serum* | A9585 | .016 .008 | .5 .5 | .06 .06 |
| Str. pyogenes +5% serum* | A9604 | .016 .008 | .25 .13 | .06 .06 |
| S. aureus Smith ++ | A9537 | .25 .06 | 1 .5 | .13 .06 |
| S. aureus Smith ++ +50% serum | A9537 | 2 2 | 2 2 | .5 .5 |
| S. aureus BX1633-2 at 10⁻³ dil'n | A9606 | .5 .13 | 2 1 | .25 .13 |
| S. aureus BX1633-2 at 10⁻² dil'n | A9606 | 4 2 | 4 2 | .5 .25 |
| S. aureus meth.-resist.; at 10⁻³ dil'n | A15097 | 4 2 | 16 16 | 1 1 |
| Sal. enteritidis ++ | A9531 | .06 .016 | 2 2 | .13 .25 |
| E. coli Juhl ++ | A15119 | 8 4 | 8 8 | 8 8 |
| E. coli ++ | A9675 | 32 32 | 16 16 | 32 63 |
| K. pneumoniae ++ | A9977 | 1 .5 | 4 4 | 2 1 |
| K. pneumoniae ++ | A15130 | 32 32 | 16 16 | 16 16 |
| Pr. mirabilis ++ | A9900 | 1 .5 | 8 4 | 1 1 |
| Pr. morganii ++ | A15153 | 125 32 | 125 125 | 125 125 |
| Ps. aeruginosa ++ | A9843A | 125 125 | 125 125 | 125 125 |
| Ser. marcescens ++ | A20019 | 125 125 | 125 125 | 125 125 |
| Ent. cloacae | A9656 | 125 | 125 | 125 |
| Ent. cloacae | A9657 | 4 16 | 4 4 | 4 8 |
| Ent. cloacae | A9659 | 125 125 | 125 125 | 125 125 |

*50% Nutrient Broth - 45% Antibiotic Assay Broth at 10⁻⁴ dilution.

EXAMPLE 22

7β-(2-Thienylacetamido)-3-(2-methyl-1,3,4-oxadiazol-5-ylthiomethyl)-Δ³-O-2-isocephem-4-carboxylic acid The p-nitrobenzyl ester of Example 19 (0.60 g., 0.15 mmole) was dissolved in 125 ml. of ethyl acetate and 40 ml. of n-butanol. The solution was treated with 1.05 ml. of 1N HCl (1.05 mmole) and hydrogenated over 0.60 g. of 20% palladium hydroxide on carbon for 3¼ hours at 50 p.s.i.g. The mixture was then filtered, washing well with ethyl acetate, and evaporated in vacuo. The residue was slurried with ether and extracted with 1% $NaHCO_3$ (2×50 ml.) followed by 25 ml. of water. The aqueous extracts were acidified in the cold with 10% HCl and extracted with ethyl acetate (3×30 ml.). The solution was dried over sodium sulfate and evaporated in vacuo. The solid residue was slurried with ether, filtered and dried giving 69 mg. (15% yield) of the title product; m.p. 170°-173°. U.V. $\lambda_{max}^{THF} = 278$ nm ($\epsilon = 12,453$).

Anal. Calc'd. for $C_{17}H_{16}N_4O_6S_2$: C, 46.78; H, 3.70; N, 12.84. Found: C, 43.95; H, 3.57; N, 11.35; residue: 3.05.

M.I.C. data for the product (called BC-L76) is shown in the following table.

| Organism | | M.I.C. in mcg./ml. | | |
|---|---|---|---|---|
| | | BC-L76 | Cephalexin | Cephalothin |
| D. pneumoniae +5% serum* | A9585 | .016 | .25 | .016 |
| Str. pyogenes +5% serum* | A9604 | .008 | .13 | .03 |
| S. aureus Smith ++ | A9537 | .06 | .5 | .06 |
| S. aureus Smith ++ +50% serum | A9537 | 1 | 1 | .25 |
| S. aureus BX1633-2 at $10^{-3}$ dil'n | A9606 | .5 | 2 | .13 |
| S. aureus BX1633-2 at $10^{-2}$ dil'n | A9606 | .5 | 4 | .13 |
| S. aureus meth.-resist.; at $10^{-3}$ dil'n | A15097 | 2 | 32 | 2 |
| Sal. enteritidis ++ | A9531 | .5 | 2 | .13 |
| E. coli Juhl ++ | A15119 | 8 | 8 | 16 |
| E. coli ++ | A9675 | 63 | 16 | 63 |
| K. pneumoniae ++ | A9977 | 1 | 4 | 2 |
| K. pneumoniae ++ | A15130 | 63 | 8 | 32 |
| Pr. mirabilis ++ | A9900 | .5 | 4 | .5 |
| Pr. morganii ++ | A15153 | 125 | >125 | >125 |
| Ps. aeruginosa ++ | A9843A | >125 | >125 | >125 |
| Ser. marcescens ++ | A20019 | >125 | >125 | >125 |
| Ent. cloacae | A9656 | >125 | >125 | >125 |
| Ent. cloacae | A9657 | 16 | 4 | 8 |
| Ent. cloacae | A9659 | >125 | >125 | >125 |

*50% Nutrient Broth - 45% Antibiotic Assay Broth at $10^{-4}$ dilution.

EXAMPLE 23

7β-phenoxyacetamido-3-(1-methyltetrazol-5-ylthiomethyl)-Δ³-O-2-isocephem-4-carboxylic acid A solution of the p-nitrobenzyl ester prepared according to Example 17 (235 mg., 0.405 mmole) in 12 ml. of tetrahydrofuran (peroxide free) and 2.4 ml. of ethanol with 140 mg. of 10% palladium-on-charcoal was hydrogenated (Parr Shaker) at 24° and 50 p.s.i. for 4 hours. The catalyst was filtered off and the solvent evaporated in vacuo. The residue was dissolved in 25 ml. of ethyl acetate and washed with 25 ml. each of 10% HCl and water. The aqueous layers were combined and extracted with 10 ml. of ethyl acetate (which was washed with 10 ml. of water). The combined ethyl acetate was extracted with 1% NaHCO₃ (2×10 ml.). The combined bicarbonate extracts were acidified with 10% HCl and extracted with ethyl acetate. The ethyl acetate extract was washed with water and saturated NaCl and then dried and evaporated in vacuo to give 67 mg. (37% yield) of crude title product. The product was crystallized from chloroform to give title product with m.p. 136°-138° (dec.). U.V. $\lambda_{max}^{MeOH}$ 276 ($\epsilon = 10,600$).

Anal. Calc'd. for $C_{18}H_{18}N_6O_6S$: C, 48.43; H, 4.06; N, 18.83; S, 7.18. Found: C, 46.70; H, 3.94 N, 17.74; S, 6.98; Residue: 1.16.

M.I.C. data for the product (called BC-L62) is shown in the following table.

| Organism | | M.I.C. in mcg./ml. | | |
|---|---|---|---|---|
| | | BC-L62 | Cephalexin | Cephalothin |
| D. pneumoniae +5% serum* | A9585 | .13 | .13 | .03 |
| Str. pyogenes +5% serum* | A9604 | .13 | .06 | .03 |
| S. aureus Smith ++ | A9537 | .25 | .25 | .06 |
| S. aureus Smith ++ +50% serum | A9537 | 1 | 1 | .25 |
| S. aureus BX1633-2 at $10^{-3}$ dil'n | A9606 | 2 | 2 | .13 |
| S. aureus BX1633-2 at $10^{-2}$ dil'n | A9606 | 16 | 4 | .25 |
| S. aureus meth.-resist.; at $10^{-3}$ dil'n | A15097 | 4 | 16 | 1 |
| Sal. enteritidis ++ | A9531 | .5 | 4 | .13 |
| E. coli Juhl ++ | A15119 | 4 | 8 | 16 |
| E. coli ++ | A9675 | 32 | 16 | 32 |
| K. pneumoniae ++ | A9977 | 2 | 4 | 1 |
| K. pneumoniae ++ | A15130 | 32 | 16 | 32 |
| Pr. mirabilis ++ | A9900 | 2 | 4 | .5 |
| Pr. morganii ++ | A15153 | 63 | 125 | >125 |
| Ps. aeruginosa ++ | A9843A | >125 | >125 | >125 |
| Ser. marcescens ++ | A20019 | >125 | >125 | >125 |
| Ent. cloacae | A9656 | >125 | >125 | >125 |
| Ent. cloacae | A9657 | 32 | 4 | 4 |
| Ent. cloacae | A9659 | 125 | >125 | >125 |

*50% Nutrient Broth - 45% Antibiotic Assay Broth at $10^{-4}$ dilution.

EXAMPLE 24

7β-[D-α-amino-α-phenylacetamido]-3-(1-methyltetrazol-5-ylthiomethyl)-Δ³-O-2-isocephem-4-carboxylic acid (hydrochloride salt)

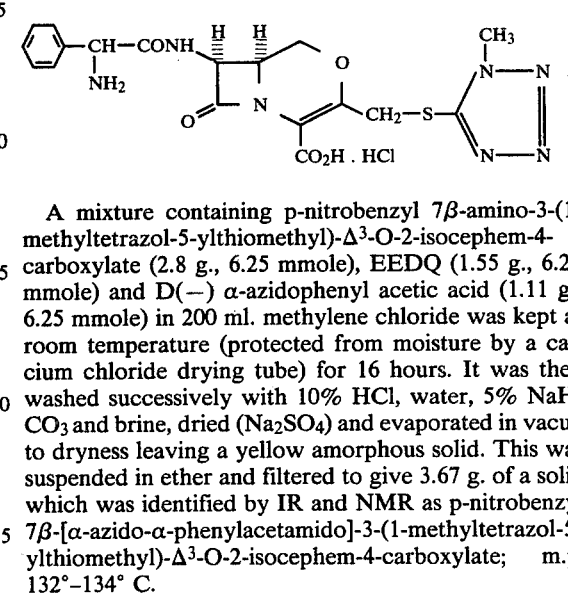

A mixture containing p-nitrobenzyl 7β-amino-3-(1-methyltetrazol-5-ylthiomethyl)-Δ³-O-2-isocephem-4-carboxylate (2.8 g., 6.25 mmole), EEDQ (1.55 g., 6.25 mmole) and D(−) α-azidophenyl acetic acid (1.11 g., 6.25 mmole) in 200 ml. methylene chloride was kept at room temperature (protected from moisture by a calcium chloride drying tube) for 16 hours. It was then washed successively with 10% HCl, water, 5% NaHCO₃ and brine, dried (Na₂SO₄) and evaporated in vacuo to dryness leaving a yellow amorphous solid. This was suspended in ether and filtered to give 3.67 g. of a solid which was identified by IR and NMR as p-nitrobenzyl 7β-[α-azido-α-phenylacetamido]-3-(1-methyltetrazol-5-ylthiomethyl)-Δ³-O-2-isocephem-4-carboxylate; m.p. 132°-134° C.

Anal. Calc'd. for $C_{25}H_{22}N_{10}O_7S$: C, 49.50; H, 3.65; N, 23.09. Found: C, 49.47; H, 3.64; N, 22.86.

A mixture consisting of the above ester (0.40 g., 0.65 mmole) and 20% Pd(OH)₂ on Celite (0.50 g.) in 50 ml. ethyl acetate, 50 ml. n-butanol and 6.5 ml. of 0.1 N HCl was shaken on a Parr apparatus under 60 p.s.i. of hydrogen for 6 hours. The solid was filtered off on a Celite pad which was washed well with absolute ethanol. The combined filtrates were evaporated in vacuo at 40° C. to leave a yellow amorphous solid. This was triturated with ether and collected by filtration to give 0.21 g.

solid; m.p. 110°-120° (decomp.). U.V. $\lambda_{max}^{THF}=274$, $\epsilon_{max}=7550$. The IR and NMR spectra of the product were in agreement with the proposed structure.

M.I.C. data for the product (called BC-L78) is shown in the following table. Purity of the sample was estimated to be about 25%.

| Organism | | M.I.C. in mcg./ml. | | |
|---|---|---|---|---|
| | | BC-L78 | Cepholexin | Cephalothin |
| D. pneumoniae +5% serum* | A9585 | 0.25 | 0.25 | .03 |
| Str. pyogenes +5% serum* | A9604 | 0.13 | 0.13 | .03 |
| S. aureus Smith ++ | A9537 | 2 | 0.5 | .06 |
| S. aureus Smith ++ +50% serum | A9537 | 8 | 1 | 0.5 |
| S. aureus BX1633-2 at $10^{-3}$ dil'n | A9606 | 8 | 2 | 0.25 |
| S. aureus BX1633-2 at $10^{-2}$ dil'n | A9606 | 63 | 8 | 0.5 |
| S. aureus meth.-resist.; at $10^{-3}$ dil'n | A15097 (37°) (28°) | 63 >125 | 32 125 | 1 63 |
| Sal. enteritidis++ | A9531 | 0.5 | 2 | 0.25 |
| E. coli Juhl ++ | A15119 | 2 | 8 | 16 |
| E. coli ++ | A9675 | 16 | 16 | 63 |
| K. pneumoniae ++ | A9977 | 1 | 4 | 1 |
| K. pneumoniae ++ | A15130 | 8 | 16 | 16 |
| Pr. mirabilis ++ | A9900 | 1 | 4 | 1 |
| Pr. morganii ++ | A9153 | 32 | >125 | >125 |
| Ps. aeruginosa ++ | A9843A | >125 | >125 | >125 |
| Ser. marcescens ++ | A20019 | >125 | >125 | >125 |
| Ent. cloacae | A9656 | >125 | >125 | >125 |
| Ent. cloacae | A9657 | 4 | 4 | 4 |
| Ent. cloacae | A9659 | 16 | >125 | >125 |

*50% Nutrient Broth - 45% Antibiotic Assay Broth at $10^{-4}$ dilution.

EXAMPLE 25

Repeating the general N-acylation procedures of Examples 15, 16, 17, 18, 19, or 24 to react the following acylating agents with 7β-amino-3-(1-methyltetrazol-5-ylthiomethyl)-Δ³-0-2-isocephem-4-carboxylic acid (or an ester or salt thereof), the following products are obtained after removal of any functional blocking groups.

| Acylating Agent | Product |
|---|---|
| mixed anhydride of potassium 2-(1-carbomethoxypropen-2-ylaminomethyl)phenylacetate with isobutyl chloroformate | 7β-(2-Aminomethylphenylacetamido)-3-(1-methyltetrazol-5-ylthiomethyl)-Δ³-0-2-isocephem-4-carboxylic acid |
| α-benzoylureidophenylacetic acid | 7β-(α-Benzoylureidophenylacetamido)-3-(1-methyltetrazol-5-ylthiomethyl)-Δ³-0-2-isocephem-4-carboxylic acid |
| 2,6-dimethoxybenzoyl chloride | 7β-(2,6-Dimethoxybenzamido)-3-(1-methyltetrazol-5-ylthiomethyl)-Δ³-0-2-isocephem-4-carboxylic acid |
| D-anhydro-o-carboxymandelic acid | 7β-(D-α-Hydroxyphenylacetamido)-3-(1-methyltetrazol-5-ylthiomethyl)-Δ³-0-2-isocephem-4-carboxylic acid |
| 3 benzyl-1,2,4-oxadiazole-5-one-4-acetic acid | 7β-[N-(Phenylacetimidoyl)-aminoacetamido]-3-(1-methyltetrazol-5-ylthiomethyl)-Δ³-0-2-isocephem-4-carboxylic acid |
| valeric acid | 7β-Valeramido-3-(1-methyltetrazol-5-ylthiomethyl)-Δ³-0-2-isocephem-4-carboxylic acid |
| phenylacetic acid | 7β-Phenylacetamido-3-(1-methyltetrazol-5-ylthiomethyl)-Δ³-0-2-isocephem-4-carboxylic acid |
| 3-thienylacetyl chloride | 7β-(3-Thienylacetamido)-3-(1-methyltetrazol-5-ylthiomethyl)-Δ³-0-2-isocephem-4-carboxylic acid |
| β-carboxybenzyl-phenylacetic acid | 7β-[α-carboxy-α-phenylacetamido]-3-(1-methyltetrazol-5-ylthiomethyl)-Δ³-0-2-isocephem-4-carboxylic acid |
| o-hydroxyphenylacetic acid | 7β-(o-Hydroxyphenylacetamido)-3-(1-methyltetrazol-5-ylthiomethyl)-Δ³-0-2-isocephem-4-carboxylic acid |
| cyanoacetic acid | 7β-[cyanoacetamido]-3-(1-methyltetrazol-5-ylthiomethyl)-Δ³-0-2-isocephem-4-carboxylic acid |
| α-cyanopropionic acid | 7β-(α-cyanopropionamido)-3-(1-methyltetrazol-5-ylthiomethyl)-Δ³-0-2-isocephem-4-carboxylic acid |
| 2-(2H)-tetrazoleacetic acid | 7β-[2-(2H)-tetrazolylacetamido]-3-(1-methyltetrazol-5-ylthiomethyl)-Δ³-0-2-isocephem-4-carboxylic acid |
| 3-(o-chlorophenyl)-5-methyl-4-isoxazole-carboxylic acid chloride | 7β-[3-(o-chlorophenyl)-5-methylisoxazol-4-ylcarboxamido]-3-(1-methyltetrazol-5-ylthiomethyl)-Δ³-0-2-isocephem-4-carboxylic acid |
| 1-(1H)-tetrazolylacetyl chloride | 7β-[1-(1H)-tetrazolylacetamido]-3-(1-methyltetrazol-5-ylthiomethyl)-Δ³-0-2-isocephem-4-carboxylic acid |

EXAMPLE 26

Repeating the general N-acylation procedures of the examples above to react the following acylating agents with 7β-amino-3-(1-methyltetrazol-5-ylthiomethyl)-Δ³-O2-isocephem-4-carboxylic acid (or an ester or salt thereof), the following products are obtained after removal of any functional blocking groups.

| Acylating Agents | Product |
|---|---|
| 4-nitrophenylacetyl chloride | 7β-(4-nitrophenylacetamido)-3-(1-methyltetrazol-5-ylthiometyl)-Δ³-0-2-isocephem-4-carboxylic acid |
| p-fluorophenylacetyl chloride | 7β-(p-fluorophenylacetamido)-3-(1-methyltetrazol-5-ylthiomethyl)-Δ³-0-2-isocephem-4-carboxylic acid |
| p-acetoxyphenylacetyl chloride | 7β-(p-acetoxyphenylacetamido)-3-(1-methyltetrazol-5-ylthiomethyl)-Δ³-0-2-isocephem-4-carboxylic acid |
| o-chlorophenylacetyl chloride | 7β-(o-chlorophenylacetamido)-3-(1-methyltetrazol-5-ylthiomethyl)-Δ³-0-2-isocephem-4-carboxylic acid |
| p-amionphenylacetyl chloride | 7β-(p-aminophenylacetamido)-3-(1-methyltetrazol-5-ylthiomethyl)-Δ³-0-2-isocephem-4-carboxylic acid |
| p-methylphenylacetyl chloride | 7β-(p-methylphenylacetamido)-3-(1-methyltetrazol-5-ylthiomethyl)-Δ³-0-2-isocephem-4-carboxylic acid |
| 4-guanidinophenylacetyl chloride hydrochlorie | 7β-(4-guanidinophenylacetamido)-3-(1-methyltetrazol-5-ylthiomethyl)-Δ³-0-2-isocephem-4-carboxylic acid |
| 4-isopropylphenylacetyl chloride | 7β-(4-isopropylphenylacetamido)-3-(1-methyltetrazol-5-ylthiomethyl)-Δ³-0-2-isocephem-4-carboxylic acid |

| Acylating Agents | Product |
| --- | --- |
| 4-methylthiophenylacetyl chloride | 7β-(4-methylthiphenylacetamido)-3-(1-methyltetrazol-5-ylthiomethyl)-Δ³-0-2-isocephem-4-carboxylic acid |
| 4-cyanophenylacetyl chloride | 7β-(4-cyanophenylacetamido)-3-(1-methyltetrazol-5-ylthiomethyl)-Δ³-0-2-isocephem-4-carboxylic acid |
| 4-methoxyphenylacetyl chloride | 7β-(4-methoxyphenylacetamido)-3-(1-methyltetrazol-5-ylthiomethyl)-Δ³-0-2-isocephem-4-carboxylic acid |
| 2,6-dimethoxyphenylacetyl chloride | 7β-(2,6-dimethoxyphenylacetamido)-3-(1-methyltetrazol-5-ylthiomethyl)-Δ³-0-2-isocephem-4-carboxylic acid |
| 3-sulfamylphenylacetyl chloride | 7β-(3-sulfamylphenylacetamido)-3-(1-methyltetrazol-5-ylthiomethyl)-Δ³-0-2-isocephem-4-carboxylic acid |
| 2-methyl-4-chlorophenyl-acetyl chloride | 7β-(2-methyl-4-chlorophenyl-acetamido)-3-(1-methyltetrazol-5-ylthiomethyl)-Δ³-0-2-isocephem-4-carboxylic acid |
| sydnone-3-acetyl chloride | 7β-(sydnone-3-acetamido)-3-(1-methyltetrazol-5-ylthiomethyl)-Δ³-0-2-isocephem-4-carboxylic acid |
| sydnone-4-acetyl chloride | 7β-(sydnone-4-acetamido)-3-(1-methyltetrazol-5-ylthiomethyl)-Δ³-0-2-isocephem-4-carboxylic acid |
| 2-furylacetyl chloride | 7β-(2-furylacetamido)-3-(1-methyltetrazol-5-ylthiomethyl)-Δ³-0-2-isocephem-4-carboxylic acid |
| 3-furylacetyl chloride | 7β-(3-furylacetamido)-3-(1-methyltetrazol-5-ylthiomethyl)-Δ³-0-2-isocephem-4-carboxylic acid |
| 1,2,5-thiadiazole-3-acetyl chloride | 7β-(1,2,5-thiadiazole-3-acetamido)-3-(1-methyltetrazol-5-ylthiomethyl)-Δ³-0-2-isocephem-4-carboxylic acid |
| 1-cyclohexenylacetyl chloride | 7β-(1-cyclohexenylacetamido)-3-(1-methyltetrazol-5-ylthiomethyl)-Δ³-0-2-isocephem-4-carboxylic acid |
| 1,4-cyclohexadienyl-acetyl chloride | 7β-(1,4-cyclohexadienyl-acetamido)-3-(1-methyletetrazol-5-ylthiomethyl)-Δ³-0-2-isocephem-4-carboxylic acid |
| 3-(1,4-cyclohexadien-1-yl)propionyl chloride | 7β-[3-(1,4-cyclohexadien-1-yl)-propionamido]-3-(1-methyltetrazol-5-ylthiomethyl)-Δ³-0-2-isocephem-4-carboxylic acid |
| isothiazol-4-yl-acetic acid | 7β-(isothioazol-4-yl-acetamido)-3-(1-methyltetrazol-5-ylthiomethyl)-Δ³-0-2-isocephem-4-carboxylic acid |
| isothiazl-5-ylacetic acid | 7β-(isothiazol-5-yl-acetamido)-3-(1-methyltetrazol-5-ylthiomethyl)-Δ³-0-2-isocephem-4-carboxylic acid |
| isothiazol-3-yl-acetic acid | 7β-(isothiazol-3-yl-acetamido)-3-(1-methyltetrazol-5-ylthiomethyl)-Δ³-0-2-isocephem-4-carboxylic acid |
| 5-phenyl-1,3,4-thiadiazolyl-2-yl-acetyl chloride | 7β-(5-phenyl-1,3,4-thiadiazol-2-yl-acetamido)-3-(1-methyltetrazol-5-ylthiomethyl)-Δ³-0-2-isocephem-4-carboxylic acid |
| thiazol-2-yl-acetyl chloride | 7β-(thiazol-2-yl-acetamido)-3-(1-methyltetrazol-5-ylthiomethyl)-Δ³-0-2-isocephem-4-carboxylic acid |
| imidazol-2-yl-acetyl chloride | 7β-(imidazol-2-yl-acetamido)-3-(1-methyltetrazol-5-ylthiomethyl)-Δ³-0-2-isocephem-4-carboxylic acid |
| 1,2,3-triazol-4-yl- | 7β-(1,2,3-triazol-4-yl-acetamido)- |
| acetic acid | 3-(1-methyltetrazol-5-ylthiomethyl)-Δ³-0-2-isocephem-4-carboxylic acid |
| oxazol-2-yl-acetyl chloride | 7β-(oxazol-2-yl-acetamido)-3-(1-methyltetrazol-5-ylthiomethyl)-Δ³-0-2-isocephem-4-carboxylic acid |
| 4-pyridylacetyl chloride | 7β-(4-pyridylacetamido)-3-(1-methyltetrazol-5-ylthiomethyl)-Δ³-0-2-isocephem-4-carboxylic acid |
| 3-pyridylacetyl chloride | 7β-(3-pyridylacetamido)-3-(1-methyltetrazol-5-ylthiomethyl)-Δ³-0-2-isocephem-4-carboxylic acid |
| 3-phenylpropionyl chloride | 7β-(3-phenylpropionamido)-3-(1-methyltetrazol-5-ylthiomethyl)-Δ³-0-2-isocephem-4-carboxylic acid |
| 3-(p-chlorophenyl)propionyl chloride | 7β-[3-(p-chlorophenyl)propionamido]-3-(1-methyltetrazol-5-ylthiomethyl)-Δ³-0-2-isocephem-4-carboxylic acid |
| 3-(p-methoxyphenyl)propionyl chloride | 7β-[p-methoxyphenyl)propionamido]-3-(1-methyltetrazol-5-ylthiomethyl)-Δ³-0-2-isocephem-4-carboxylic acid |
| 3-(p-sulfamylphenyl)-propionyl chloride | 7β[3-(p-sulfamylphenyl)propionamido]-3-(1-methyltetrazol-5-ylthiomethyl)-Δ³-0-2-isocephem-4-carboxylic acid |
| 3-(3,4-dimethoxyphenyl)-propionyl chloride | 7β-[3-(3,4-dimethoxyphenyl)-propionamido]-3-(1-methyltetrazol-5-ylthiomethyl)-Δ³-0-2-isocephem-4-carboxylic acid |
| 3-(p-hydroxyphenyl)-propionic acid | 7β-[3-(p-hydroxyphenyl)propionamido]-3-(1-methyltetrazol-5-ylthiomethyl)-Δ³-0-2-isocephem-4-carboxylic acid |
| 3-(p-nitrophenyl)-propionic acid | 7β[3-(p-nitrophenyl)propionamido]-3-(1-methyltetrazol-5-ylthiomethyl)-Δ³-0-2-isocephem-4-carboxylic acid |
| 3-(2-thienyl)propionyl | 7β-[3-(2-thienyl)propionamido]-3-(1-methyltetrazol-5-ylthiomethyl)-Δ³-0-2-isocephem-4-carboxylic acid |
| 3-(3-thienyl)propionyl | 7β-[3-(3-thienyl)propionamido]-3-(1-methyltetrazol-5-ylthiomethyl)-Δ³-0-2-isocephem-4-carboxylic acid |
| cyclohexylacetic acid | 7β-(cyclohexylacetamido)-3-(1-methyltetrazol-5-ylthiomethyl)-Δ³-0-2-isocephem-4-carboxylic acid |
| 3-phenyl-5-methylisoxazol-4-yl-acetic acid | 7β-(3-phenyl-5-methylisoxazol-4-yl-acetamido)-3-(1-methyltetrazol-5-ylthiomethyl)-Δ³-0-2-isocephem-4-carboxylic acid |
| o-aminomethylphenylacetic acid | 7β-(o-aminomethylphenyl-acetamido)-3-(1-methyltetrazol-5-ylthiomethyl)-Δ³-0-2-isocephem-4-carboxylic acid |
| 3-methoxy-4-furazanacetyl chloride | 7β-(3-methoxy-4-furazan-acetamido)-3-(1-methyltetrazol-5-ylthiomethyl)-Δ³-0-2-isocephem-4-carboxylic acid |
| acetic acid | 3-(1-methyltetrazol-5-ylthiomethyl)-Δ³-0-2-isocephem-4-carboxylic acid |

EXAMPLE 27

Repeating the general N-acylation procedures of the examples above to react the following acylating agents with 7β-amino-3-(1-methyltetrazol-5-ylthiomethyl)-Δ³-0-2-isocephem-4-carboxylic acid (or an ester or salt thereof), the following products are obtained after removal of any functional blocking groups.

| Acylating Agent | Product |
|---|---|
| p-nitrophenoxyacetic acid | 7β-(p-nitrophenoxyacetamido)-3-(1-methyltetrazol-5-ylthiomethyl)-$\Delta^3$-0-2-isocephem-4-carboxylic acid |
| p-fluorophenoxyacetic acid | 7β-(p-fluorophenoxyacetamido)-3-(1-methyltetrazol-5-ylthiomethyl)-$\Delta^3$-0-2-isocephem-4-carboxylic acid |
| o-chlorophenoxyacetic acid | 7β-(o-chlorophenoxyacetamido)-3-(1-methyltetrazol-5-ylthiomethyl)-$\Delta^3$-0-2-isocephem-4-carboxylic acid |
| p-sulfamylphenoxyacetic acid | 7β-(p-sulfamylphenoxyacetamido)-3-(1-methyltetrazol-5-ylthiomethyl)-$\Delta^3$-0-2-isocephem-4-carboxylic acid |
| p-methylphenoxyacetic acid | 7β-(p-methylphenoxyacetamido)-3-(1-methyltetrazol-5-ylthiomethyl)-$\Delta^3$-0-2-isocephem-4-carboxylic acid |
| 4-hydroxyphenoxyacetic | 7β-(4-hydroxyphenoxyacetamido)-3-(1-methyltetrazol-5-ylthiomethyl)-$\Delta^3$-0-2-isocephem-4-carboxylic acid |
| 2,4-dichlorophenoxyacetic acid | 7β(2,4-dichlorophenoxyacetamido)-3-(1-methyltetrazol-5-ylthiomethyl)-$\Delta^3$-0-2-isocephem-4-carboxylic acid |
| 2,6-dimethoxyphenoxyacetic acid | 7β-(2,6-dimethoxyphenoxyacetamido)-3-(1-methyltetrazol-5-ylthiomethyl)-$\Delta^3$-0-2-isocephem-4-carboxylic acid |
| 4-cyanophenoxyacetic acid | 7β-(4-cyanophenoxyacetamido)-3-(1-methyltetrazol-5-ylthiomethyl)-$\Delta^3$-0-2-isocephem-4-carboxylic acid |
| α-phenoxypropionic acid | 7β-(α-phenoxypropionamido)-3-(1-methyltetrazol-5-ylthiomethyl)-$\Delta^3$-0-2-isocephem-4-carboxylic acid |
| α-(2-chlorophenoxy)-propionic acid | 7β-[α-(2-chlorophenoxy)propionamido]-3-(1-methyltetrazol-5-ylthiomethyl)-$\Delta^3$-0-2-isocephem-4-carboxylic acid |
| α-(2,4-dichlorophenoxy)-n-butyric acid | 7β-[α-(2,4-dichlorophenoxy)-n-butyramido]-3-(1-methyltetrazol-5-ylthiomethyl)-$\Delta^3$-0-2-isocephem-4-carboxylic acid |
| α-phenoxyphenylacetic acid | 7β-(αphenoxyphenylacetamido)-3-(1-methyltetrazol-5-ylthiomethyl)-$\Delta^3$-0-2-isocephem-4-carboxylic acid |
| α-phenoxybutyric acid | 7β-(α-phenoxybutyramido)-3-(1-methyltetrazol-5-ylthiomethyl)-$\Delta^3$-0-2-isocephem-4-carboxylic acid |
| 4-trifluoromethylphenoxyacetic acid | 7β-(4-trifluoromethylphenoxyacetamido)-3-(1-methyltetrazol-5-ylthiomethyl)-$\Delta^3$-0-2-isocephem-4-carboxylic acid |
| benzyloxyacetyl chloride | 7β-(benzyloxyacetamido)-3-(1-methyltetrazol-5-ylthiomethyl)-$\Delta^3$-0-2-isocephem-4-carboxylic acid |
| β-naphthoxyacetyl chloride | 7β-(β-naphthoxyacetamdio)-3-(1-methyltetrazol-5-ylthiomethyl)-$\Delta^3$-0-2-isocephem-4-carboxylic acid |

Example 28

Following the general N-acylation methods of the preceeding examples, the compounds listed below are prepared by acylating 7β-amino-3-(1-methyltetrazol-5-ylthiomethyl)-$\Delta^3$-0-2-isocephem-4-carboxylic acid with an acylating acid of the formula

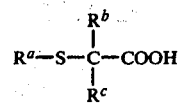

or a functional equivalent, e.g. acid halide, thereof.

| $R^a$ | $R^b$ | $R^c$ |
|---|---|---|
| Cl—C6H4— | H | H |
| 2-CF3-C6H4— | H | H |
| 2-Cl,3-CH3-C6H4— | H | H |
| C6H5— | H | H |
| 2-CH2NH2-C6H4— | H | H |
| 4-H2NCH2-C6H4— | H | H |
| C6H5— | H | H |
| 4-F-C6H4— | H | H |
| 4-pyridyl | H | H |
| 3-pyridyl | H | H |
| C6H5—CH2— | H | H |
| 2-CN-C6H4— | H | H |
| imidazolyl (2) | H | H |
| imidazolinyl (2) | H | H |
| thiazolyl (2) | H | H |
| thiazolinyl (2) | H | H |
| triazolyl (2) | H | H |
| 1-methyl-imidazolyl (2) | H | H |
| 2-thienyl | H | H |
| 3-thienyl | H | H |
| n-butyl | H | H |
| isobutyl | H | H |
| 2-acetamido-thiazol-5-yl | H | H |
| 2-phenyl-1,3,4-thiadiazol-5-yl | H | H |
| 2-methyl-1,3,4-oxadiazol-5-yl | H | H |

EXAMPLE 29

Following the general N-acylation methods of the proceeding examples, the compounds listed below are prepared by acylation of 7β-amino-3-(1-methyltetrazol-5-ylthiomethyl)-$\Delta^3$-0-2-isocephem-4-carboxylic acid with the appropriate acylating acid of the general formula $R^a$—COOH or a functional equivlent thereof.

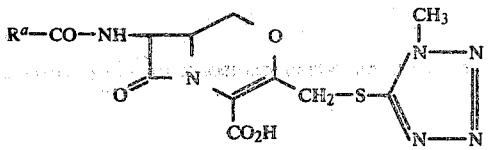

7β-(3-phenyl-5-methyl-isoxazol-4-ylcarboxamido)-3-(1-methyltetrazol-5-ylthiomethyl)-$\Delta^3$-0-2-isocephem-4-carboxylic acid;

7β-[3-(2,6-dichlorophenyl)-5-methylisoxazol-4-ylcarboxamido]-3-(1-methyltetrazol-5-ylthiomethyl)-$\Delta^3$-0-2-isocephem-4-carboxylic acid;

7β-(2,6-dichlorobenzamido)-3-(1-methyltetrazol-5-ylthiomethyl)-$\Delta^3$-0-2-isocephem-4-carboxylic acid;

7β-(2-phenylbenzamido)-3-(1-methyltetrazol-5-ylthiomethyl)-$\Delta^3$-0-2-isocephem-4-carboxylic acid;

7β-(2-aminomethylbenzamido)-3-(1-methyltetrazol-5-ylthiomethyl)-$\Delta^3$-0-2-isocephem-4-carboxylic acid;

7β-(2-carboxybenzamido)-3-(1-methyltetrazol-5-ylthiomethyl)-$\Delta^3$-0-2-isocephem-4-carboxylic acid;

7β-(cyclopentanecarboxamido)-3-(1-methyltetrazol-5-ylthiomethyl)-$\Delta^3$-0-2-isocephem-4-carboxylic acid;

7β-(1-aminocyclohexanecarboxamido)-3-(1-methyltetrazol-5-ylthiomethyl)-$\Delta^3$-0-2-isocephem-4-carboxylic acid;

7β-(cyclohexanecarboxamido)-3-(1-methyltetrazol-5-ylthiomethyl)-$\Delta^3$-0-2-isocephem-4-carboxylic acid;

7β-(1,4-cyclohexadienylcarboxamido)-3-(1-methyltetrazol-5-ylthiomethyl)-$\Delta^3$-0-2-isocephem-4carboxylic acid;

7β-(4-nitrobenzamido)-3-(1-methyltetrazol-5-ylthiomethyl)-$\Delta^3$-0-2-isocephem-4-carboxylic acid;

7β-(4-methylbenzamido)-3-(1-methyltetrazol-5-ylthiomethyl)-$\Delta^3$-0-2-isocephem-4-carboxylic acid;

7β-(o-methoxybenzamido)-3-(1-methyltetrazol-5-ylthiomethyl)-$\Delta^3$-0-2-isocephem-4-carboxylic acid;

7β-(o-bromobenzamido)-3-(1-methyltetrazol-5-ylthiomethyl)-$\Delta^3$-0-2-isocephem-4-carboxylic acid;

7β-(p-ethoxybenzamido)-3-(1-methyltetrazol-5-ylthiomethyl)-$\Delta^3$-0-2-isocephem-4-carboxylic acid;

7β-(o-acetamidobenzamido)-3-(1-methyltetrazol-5-ylthiomethyl)-$\Delta^3$-0-2-isocephem-4-carboxylic acid;

7β-(p-allylbenzamido)-3-(1-methyltetrazol-5-ylthiomethyl)-$\Delta^3$-0-2-isocephem-4-carboxylic acid;

7β-(2,5-dihydroxybenzamido)-3-(1-methyltetrazol-5-ylthiomethyl)-$\Delta^3$-0-2-isocephem-4-carboxylic acid;

7β-(2-ethoxy-1-naphthamido)-3-(1-methyltetrazol-5-ylthiomethyl)-$\Delta^3$-0-2-isocephem-4-carboxylic acid;

7β-(2-methoxy-1-naphthamido)-3-(1-methyltetrazol-5-ylthiomethyl)-$\Delta^3$-0-2-isocephem-4-carboxylic acid;

7β-(o-dimethylaminobenzamido)-3-(1-methyltetrazol-5-ylthiomethyl)-$\Delta^3$-0-2-isocephem-4-carboxylic acid;

7β-(benzamido)-3-(1-methyltetrazol-5-ylthiomethyl)-$\Delta^3$-0-2-isocephem-4-carboxylic acid;

7β-(p-chlorobenzamido)-3-(1-methyltetrazol-5-ylthiomethyl)-$\Delta^3$-0-2-isocephem-4-carboxylic acid;

7β-(2-thienylcarboxamido)-3-(1-methyltetrazol-5-ylthiomethyl)-$\Delta^3$-0-2-isocephem-4-carboxylic acid;

7β-(3-thienylcarboxamido)-3-(1-methyltetrazol-5-ylthiomethyl)-$\Delta^3$-0-2-isocephem-4-carboxylic acid;

7β-(2-furylcarboxamido)-3-(1-methyltetrazol-5-ylthiomethyl)-$\Delta^3$-0-2-isocephem-4-carboxylic acid;

7β-(3-furylcarboxamido)-3-(1-methyltetrazol-5-ylthiomethyl)-$\Delta^3$-0-2-isocephem-4-carboxylic acid;

7β-(2'-chlorocyclobutanecarboxamido)-3-(1-Methyltetrazol-5-ylthiomethyl)-$\Delta^3$-0-2-isocephem-4-carboxylic acid;

7β-(3'-fluorocyclopentanecarboxamido)-3-(1-methyltetrazol-5-ylthiomethyl)-$\Delta^3$-0-2-isocephem-4-carboxylic acid;

7β-(3'-methylcyclopentanecarboxamido)-3-(1-methyltetrazol-5-ylthiomethyl)-$\Delta^3$-0-2-isocephem-4-carboxylic acid;

7β-(3'-methoxycyclopentanecarboxamido)-3-(1-methyltetrazol-5-ylthiomethyl)-$\Delta^3$-0-2-isocephem-4-carboxylic acid;

7β-(α-naphthamido)-3-(1-methyltetrazol-5-ylthiomethyl)-$\Delta^3$-0-2-isocephem-4-carboxylic acid;

7β-(β-naphthamido)-3-(1-methyltetrazol-5-ylthiomethyl)-$\Delta^3$-0-2-isocephem-4-carboxylic acid; 7β-(1-aminocyclopentanecarboxamido)-3-(1-methyltetrazol-5-ylthiomethyl)-$\Delta^3$-0-2-isocephem-4-carboxylic acid;

7β-(1-aminocycloheptanecarboxamido)-3-(1-methyltetrazol-5-ylthiomethyl)-$\Delta^3$-0-2-isocephem-4-carboxylic acid;

7β-(1-cyclohexenecarboxamido)-3-(1-methyltetrazol-5-ylthiomethyl)-$\Delta^3$-0-2-isocephem-4-carboxylic acid.

EXAMPLE 30

Repeating the general N-acylation procedures of the above examples to react trityl chloride with 7β-amino-3-(1-methyltetrazol-5-ylthiomethyl)-$\Delta^3$-0-2-isocephem-4-carboxylic acid (or an ester or salt thereof), there is obtained after removal of any carboxyl-protecting group, 7β-triphenylmethylcarboxamido-3-(1-methyltetrazol-5-ylthiomethy)-$\Delta^3$-0-2-isocephem-4-carboxylic acid.

EXAMPLE 31

Following the acylation methods of the preceeding examples and in particular those disclosed in U.S. Pat. No. 3,546,219, the compounds listed below are prepared by reacting 7β-amino-3-(1-methyltetrazol-5-ylthiomethyl)-$\Delta^3$-0-2-isocephem-4-carboxylic acid (or an ester or salt thereof), with the appropriate acylating agent.

| $R^y$ |
|---|
| phenyl |
| p-acetamidophenyl |
| p-methoxyphenyl |
| p-methylphenyl |
| 2-methoxy-5-methylphenyl |
| m-chlorophenyl |
| o-nitrophenyl |
| 2,4-dichlorophenyl |
| α-naphthyl |
| 2-phenanthryl |
| p-aminophenyl |
| 2-thienyl |
| p-dimethylaminophenyl. |

EXAMPLE 32

Following the acylation methods of the preceeding examples and in particular those disclosed in U.K. Pat. Nos. 1,296,081 and 1,294,541, the compounds listed below are prepared by reacting 7β-amino-3-(1-methyltetrazol-5-ylthiomethyl)-Δ³-0-2-isocephem-4-carboxylic acid or an ester or salt thereof with an acylating agent of the formula

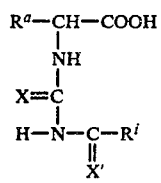

or a functional equivalent thereof.

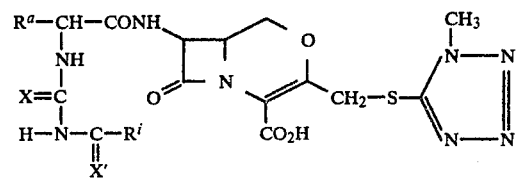

| R$^a$ | X | X' | R$^i$ |
|---|---|---|---|
| phenyl | O | imino | NH$_2$ |
| 2-thienyl | O | imino | NH$_2$ |
| 3-thienyl | O | imino | NH$_2$ |
| m-nitrophenyl | O | imino | NH$_2$ |
| m-aminophenyl | O | imino | NH$_2$ |
| p-methylphenyl | O | imino | NH$_2$ |
| p-chlorophenyl | O | imino | NH$_2$ |
| p-methoxyphenyl | O | imino | NH$_2$ |
| P-hydroxyphenyl | O | imino | NH$_2$ |
| p-dimethylaminophenyl | O | imino | NH$_2$ |
| 3,4-dimethoxyphenyl | O | imino | NH$_2$ |
| m-methoxyphenyl | O | imino | NH$_2$ |
| p-acetamidophenyl | O | imino | NH$_2$ |
| m-hydroxyphenyl | O | imino | NH$_2$ |
| 3,5-dichloro-4-hydroxyphenyl | O | imino | NH$_2$ |
| 3-chloro-4-hydroxyphenyl | O | imino | NH$_2$ |
| phenyl | O | O | 2-furyl |
| 2-thienyl | O | O | 2-furyl |
| 3-thienyl | O | O | 2-furyl |
| phenyl | O | O | phenyl |
| 2-thienyl | O | O | phenyl |
| phenyl | O | O | 2-thienyl |
| p-chlorophenyl | O | O | 2-furyl |
| p-hydroxyphenyl | O | O | 2-furyl |
| 3-chloro-4-hydroxyphenyl | O | O | 2-furyl |
| 3,5-dichloro-4-hydroxyphenyl | O | O | 2-furyl |
| m-aminophenyl | O | O | 2-furyl |
| p-methylphenyl | O | O | 2-furyl |
| p-dimethylaminophenyl | O | O | 2-furyl |
| p-methoxyphenyl | O | O | 2-furyl |
| m-hydroxyphenyl | O | O | 2-furyl |
| p-acetamidophenyl | O | O | 2-furyl |
| m-nitrophenyl | O | O | 2-furyl |
| phenyl | O | O | CH$_3$ |
| 2-thienyl | O | O | CH$_3$ |
| 3-theinyl | O | O | CH$_3$ |
| phenyl | O | O | —CH$_2$—C$_6$H$_5$ |
| phenyl | O | O | 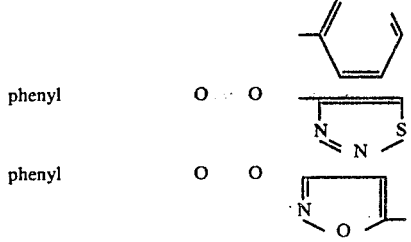 |
| phenyl | O | O | |
| phenyl | O | O | |

-continued

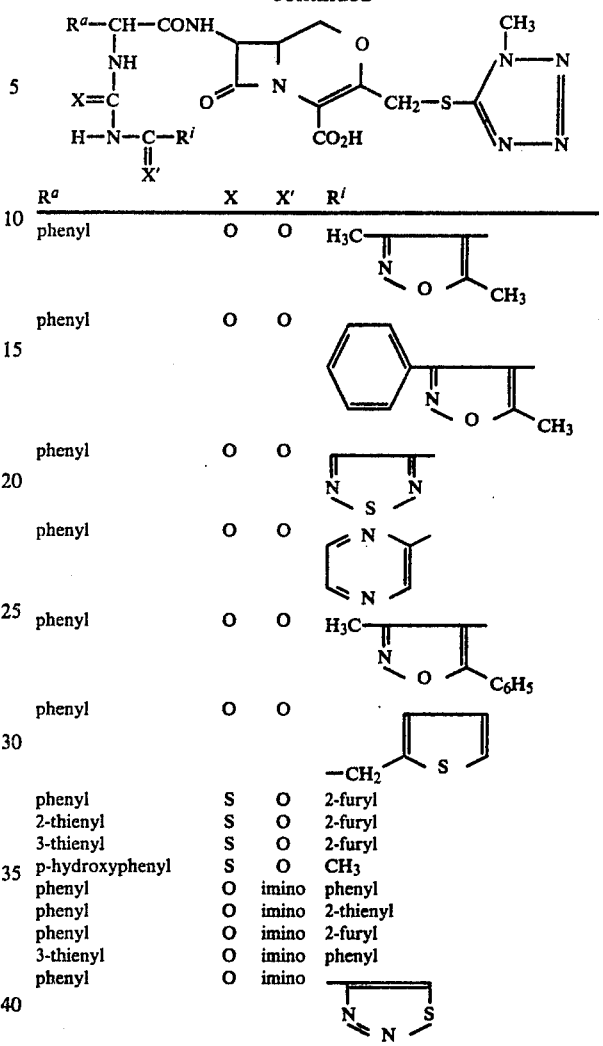

| R$^a$ | X | X' | R$^i$ |
|---|---|---|---|
| phenyl | O | O | |
| phenyl | O | O | |
| phenyl | O | O | |
| phenyl | O | O | |
| phenyl | O | O | |
| phenyl | O | O | |
| phenyl | S | O | 2-furyl |
| 2-thienyl | S | O | 2-furyl |
| 3-thienyl | S | O | 2-furyl |
| p-hydroxyphenyl | S | O | CH$_3$ |
| phenyl | O | imino | phenyl |
| phenyl | O | imino | 2-thienyl |
| phenyl | O | imino | 2-furyl |
| 3-thienyl | O | imino | phenyl |
| phenyl | O | imino | |

EXAMPLE 33

When 7β-amino-3-(1-methyltetrazol-5-ylthiomethyl)-Δ³-0-2-isocephem-4-carboxylic acid or an ester or salt thereof is acylated according to the procedures above and in particular those disclosed in U.S. Pat. No. 3,692,779 with an acid chloride of the formula

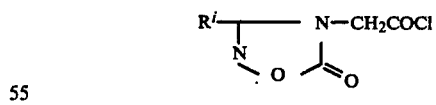

there are produced the compounds listed below.

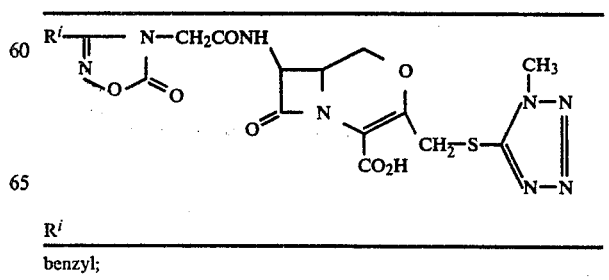

R$^i$ benzyl;

-continued

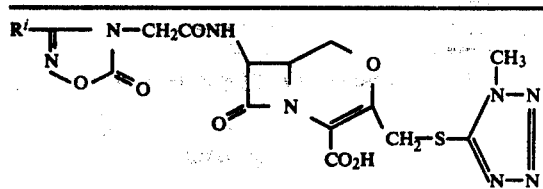

R<sup>i</sup>

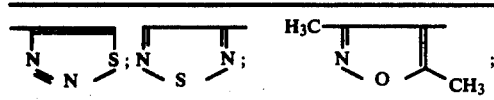

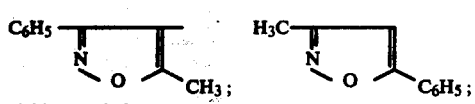

dichloromethyl;
n-propyl;
cyclopentyl;
cyclohexyl;
p-chlorobenzyl;
phenyl;
2-thienyl;
3-thienyl.

EXAMPLE 34

When the 7-acylamido-3-(1-methyltetrazol-5-ylthiomethyl)-Δ³-0-2-isocephem-4-carboxylic acid compounds of Example 33 are hydrogenated as by the process of U.S. Pat. No. 3,692,779, there are produced the compounds listed below.

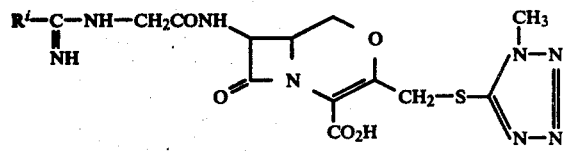

where R$^i$ is as defined in Example 33.

EXAMPLE 35

When 7β-amino-3-(1-methyltetrazol-5-ylthiomethyl)-Δ³-0-2-isocephem-4-carboxylic acid or an ester or salt thereof is acylated according to the procedures of the above examples (and in particular the procedures disclosed in U.S. Pat. No. 3,646,024) with an acid chloride of the formula

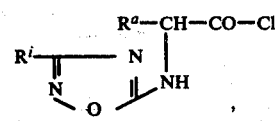

there are produced the compounds listed below.

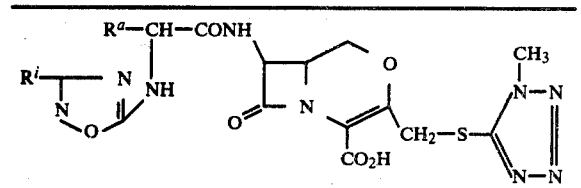

| R$^a$ | R$^i$ |
|---|---|
| phenyl | phenyl |
| phenyl | 2-thienyl |
| phenyl | 2-furyl |
| 2-thienyl | phenyl |
| 3-thienyl | 2-furyl |
| p-hydroxyphenyl | phenyl |

EXAMPLE 36

When 7β-amino-3-(1-methyltetrazol-5-ylthiomethyl)-Δ³-0-2-isocephem-4-carboxylic acid or an ester or salt thereof is acylated according to the procedures above and in particular according to the methods of U.S. Pat. No. 3,778,436 with an acylating agent of the formula

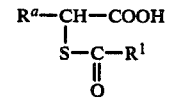

or a functional equivalent thereof, there are produced the compounds listed below

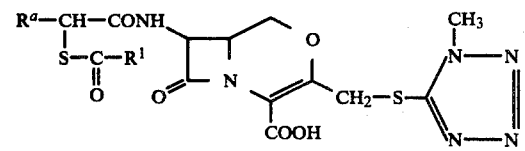

| R$^a$ | R$^1$ |
|---|---|
| 3,4-dimethoxyphenyl | ethyl |
| p-methylphenyl | 2-thienyl |
| 2,4-dichlorophenyl | ethyl |
| 5-methyl-3-phenyl-isoxazol-4-yl | ethyl |
| 2-thienyl | ethyl |
| 2-furyl | 2-furyl |
| phenyl | phenyl |
| 1,4-cyclohexadien-1-yl | methyl |

EXAMPLE 37

When p-nitrobenzyl 7β-amino-3-(1-methyltetrazol-5-ylthiomethyl)-Δ³-0-2-isocephem-4-carboxylate is reacted with equimolar quantities of EEDQ and the N-t-butoxycarbonylamino acylating acids listed below, there are produced after catalytic hydrogenation the following compounds.

| Acylating Agent | Product |
|---|---|
| D-(-)-α-(3,5-dichloro-4-hydroxyphenyl)-α-(t-butoxycarbonylamino)acetic acid | 7β-[D-(-)-α-amino-α-(3,5-dichloro-4-hydroxyphenyl)-acetamido]-3-(1-methyl-tetrazol-5-ylthiomethyl)-Δ³- |

-continued

| Acylating Agent | Product |
|---|---|
| D-(-)-α-(3-chloro-4-hydroxyphenyl)-2-(t-butoxy-carbonylamino)acetic acid | O-2-isocephem-4-carboxylic acid 7β-[D-(-)-α-amino-α-(3-chloro-4-hydroxyphenyl)acetamido]-3-(1-methyltetrazol-5-ylthiomethyl)-Δ³-O-2-isocephem-4-carboxylic acid |
| D-(-)-α-(p-hydroxyphenyl)-α-(t-butoxycarbonylamino)-acetic acid | 7β-[D-(-)-α-amino-α-(p-hydroxyphenyl)acetamido]-3-(1-methyltetrazol-5-ylthiomethyl)-Δ³-O-2-isocephem-4-carboxylic acid |
| 2-(N-t-butoxycarbonyl-amino)-2-(2,4,6-cyclo-heptatrien-1-yl-acetic acid | 7β-[α-amino-α-(2,4,6-cyclo-heptatrien-1-yl)acetamido]-3-(1-methyltetrazol-5-ylthiomethyl)-Δ³-O-2-isocephem-4-carboxylic acid |
| D-2-(t-butoxycarbonyl-amino)-2-(3'-hydroxy-phenyl)acetic acid | 7β-[D-α-amino-α-(3'-hydroxyphenyl)acetamido]-3-(1-methyltetrazol-5-ylthiomethyl)-Δ³-O-2-isocephem-4-carboxylic acid |
| D-α-(t-butoxycarbonyl-amino)-α-4-acetamido-phenylacetic acid | 7β-[D-α-amino-α-(4-acetamidophenyl)acetamido]-3-(1-methyltetrazol-5-ylthiomethyl)-Δ³-O-2-isocephem-4-carboxylic acid |
| D-2-(t-butoxycarbonyl-amino)-2-(1,4-cyclo-hexadienyl)acetic acid | 7β-[D-α-amino-α-(1,4-cyclohexadienyl)acetamido]-3-(1-methyltetrazol-5-ylthiomethyl)-Δ³-O-2-isocephem-4-carboxylic acid |
| D-3-(t-butoxycarbonyl-amino)-3-(1,4-cyclo-hexadienyl)propionic acid | 7β-[D-3'-amino-3'-(1,4-cyclohexadienyl)propionamido]-3-(1-methyltetrazol-5-ylthiomethyl)-Δ³-O-2-isocephem-4-carboxylic acid |
| D-(-)-α-(2-thienyl)-α-(t-butoxycarbonylamino)-acetic acid | 7β-[D-α-amino-α-(2-thienyl)-acetamido]-3-(1-methyltetrazol-5-ylthiomethyl)-Δ³-O-2-isocephem-4-carboxylic acid |
| D-(-)-α-(3-thienyl)-α-(t-butoxycarbonylamino)-acetic acid | 7β-[-α-amino-α-(3-thienyl)-acetamido]-3-(1-methyltetrazol-5-ylthiomethyl)-Δ³-O-2-isocephem-4-carboxylic acid |
| D-α-(t-butoxycarbonyl-amino)-α-(o-hydroxyphenyl)-acetic acid | 7β-[D-α-amino-α-(o-hydroxyphenyl)acetamido]-3-(1-methyltetrazol-5-ylthiomethyl)-Δ³-O-2-isocephem-4-carboxylic acid |
| D-α-(t-butoxycarbonyl-amino)-α-(p-nitrophenyl)-acetic acid | 7β-[D-α-amino-α-(p-nitrophenyl)acetamido]-3-(1-methyltetrazol-5-ylthiomethyl)-Δ³-O-2-isocephem-4-carboxylic acid |
| D-α-(t-butoxycarbonyl-amino)-α-(p-methoxyphenyl)-acetic acid | 7β-[D-α-amino-α-(p-methoxyphenyl)acetamido]-3-(1-methyltetrazol-5-ylthiomethyl)-Δ³-O-2-isocephem-4-carboxylic acid |
| D-α-(t-butoxycarbonyl-amino)-α-(p-cyanophenyl)-acetic acid | 7β-[D-α-amino-α-(p-cyanophenyl)-acetamido]-3-(1-methyltetrazol-5-ylthiomethyl)-Δ³-O-2-isocephem-4-carboxylic acid |
| D-α-(t-butoxycarbonyl-amino)-α-(p-methylthio-phenyl)acetic acid | 7β-[D-α-amino-α-(p-methylthiophenyl)acetamido]-3-(1-methyltetrazol-5-ylthiomethyl)-Δ³-O-2-isocephem-4-carboxylic acid |
| D-α-(t-butoxycarbonyl-amino)-α-(p-isopropyl-phenyl)acetic acid | 7β-[D-α-amino-α-(p-isopropylphenyl)acetamido]-3-(1-methyltetrazol-5-ylthiomethyl)-Δ³-O-2-isocephem-4-carboxylic acid |
| D-α-(t-butoxycarbonyl-amino)-α-(o-sulfamyl-phenyl)acetic acid | 7β-[D-α-amino-α-(o-sulfamylphenyl)acetamido]-3-(1-methyltetrazol-5-ylthiomethyl)-Δ³-O-2-isocephem-4-carboxylic acid |
| D-α-(t-butoxycarbonyl-amino)-α-(o-aminomethyl-phenyl)acetic acid | 7β-[D-α-amino-α-(o-aminomethylphenyl)acetamido]-3-(1-methyltetrazol-5-ylthiomethyl)-Δ³-O-2-isocephem-4-carboxylic acid |
| D-α-(t-butoxycarbonyl-amino)-α-(o-dimethylamino-phenyl)acetic acid | 7β-[D-α-amino-α-(o-dimethylaminophenyl)acetamido]-3-(1-methyltetrazol-5-ylthiomethyl)-Δ³-O-2-isocephem-4-carboxylic acid |
| D-α-(t-butoxycarbonyl-amino)-α-(4-chloro-2-thienyl)acetic acid | 7β-[D-α-amino-α-(4-chloro-2-thienyl)acetamido]-3-(1-methyltetrazol-5-ylthiomethyl)-Δ³- |

| Acylating Agent | Product |
| --- | --- |
| D-α-(t-butoxycarbonyl-amino)-α-(cyclohexyl)-acetic acid | O-2-isocephem-4-carboxylic acid 7β-[D-α-amino-α-(cyclohexyl)-acetamido]-3-(1-methyltetrazol-5-ylthiomethyl)-Δ³-O-2-isocephem-4-carboxylic acid |
| D-α-(t-butoxycarbonyl-amino)-α-(3-trifluoro-methylphenyl)acetic acid | 7β-[D-α-amino-α-(3-trifluoro-methylphenyl)acetamido]-3-(1-methyltetrazol-5-ylthiomethyl)-Δ³-O-2-isocephem-4-carboxylic acid |

EXAMPLE 38

When 7β-amino-3-(1-methyltetrazol-5-ylthiomethyl)-Δ³-O-0-2-isocephem-4-carboxylic acid or an ester or salt thereof is acylated according to the general procedures of the preceedding examples with the acylating agents listed below (suitably protected), there are produced the following compounds.

When 7β-amino-3-(1-methyltetrazol-5-ylthiomethyl)-Δ³-O-2-isocephem-4-carboxylic acid or an ester or salt thereof is acylated according to the general procedures of the preceeding examples with the acylating agents listed below (suitably protected), there are produced the following compounds.

| Acylating Agent | Product |
| --- | --- |
| α-amino-α-(1-cyclohexenyl)-acetic acid | 7β-[α-amino-α-(1-cyclohexenyl)-acetamido]-3-(1-methyltetrazol-5-ylthiomethyl)-Δ³-O-2-isocephem-4-carboxylic acid |
| α-amino-α-(isothiazol-4-yl)acetyl chloride | 7β-[α-amino-α-(isothiazol-4-yl)acetamido]-3-(1-methyltetrazol-5-ylthiomethyl)-Δ³-O-2-isocephem-4-carboxylic acid |
| α-amino-α-(5-phenyl-1,3,4-thiadiazol-2-yl)acetyl chloride | 7β-[α-amino-α-(5-phenyl-1,3,4-thiadiazol-2-yl)acetamido]-3-(1-methyltetrazol-5-ylthiomethyl)-Δ³-O-2-isocephem-4-carboxylic acid |
| α-amino-α-(5-phenyl-1,3,4-oxadiazol-2-yl)acetyl chloride | 7β-[α-amino-α-(5-phenyl-1,3,4-oxadiazol-2-yl)acetamido]-3-(1-methyltetrazol-5-ylthiomethyl)-Δ³-O-2-isocephem-4-carboxylic acid |
| α-amino-α-(3-methyl-1,2,5-oxadiazol-4-yl)acetyl chloride | 7β-[α-amino-α-(3-methyl-1,2,5-oxadiazol-4-yl)acetamido]-3-(1-methyltetrazol-5-ylthiomethyl)-Δ³-O-2-isocephem-4-carboxylic acid |
| α-amino-α-(oxazol-2-yl)-acetyl chloride | 7β-[α-amino-α-(oxazol-2-yl)-acetamido]-3-(1-methyltetrazol-5-ythiomethyl)-Δ³-O-2-isocephem-4-carboxylic acid |
| α-amino-α-(1H)-tetra-zolylacetyl chloride | 7β-[α-amino-α-(1H)-tetrazolyl-acetamido]-3-(1-methyltetrazol-5-ylthiomethyl)-Δ³-O-2-isocephem-4-carboxylic acid |
| α-amino-α-4-isoxazolyl-acetyl chloride | 7β-[α-amino-α-(4-isoxazolyl)-acetamido]-3-(1-methyltetrazol-5-ylthiomethyl)-Δ³-O-2-isocephem-4-carboxylic acid |
| α-amino-α-(2-thiazolyl)-acetyl chloride | 7β-(α-amino-α-(2-thiazolyl)-acetamido]-3-(1-methyltetrazol-5-ylthiomethyl)-Δ³-O-2-isocephem-4-carboxylic acid |
| α-amino-α-(2-furyl)-acetyl chloride | 7β-[α-amino-α-(2-furyl)-acetamido]-3-(1-methyltetrazol-5-ylthiomethyl)-Δ³-O-2-isocephem-4-carboxylic acid |
| α-amino-α-(1,2,5-thiadiazol-3-yl)acetyl chloride | 7β-[α-amino-α-(1,2,5-thiadizaol-3-yl)acetamido]-3-(1-methyl-tetrazol-5-ylthiomethyl)-Δ³-O-2-isocephem-4-carboxylic acid |
| α-amino-α-(3-furyl)acetyl chloride | 7β-[α-amino-α-(3-furyl)-acetamido]-3-(1-methyltetrazol-5-ylthiomethyl-Δ³-O-2-isocephem-4-carboxylic acid |

EXAMPLE 39

When benzyl 7β-amino-3-(1-methyltetrazol-5-ylthiomethyl)-Δ³-0-2-isocephem-4-carboxylate is acylated according to the general acylation procedures above with the acylating agents listed below (suitably protected if necessary), there are produced the following compounds after removal of any protecting groups:

| Acylating Agent | Product |
|---|---|
| D-3-chloromandelic acid | 7β-[D-α-hydroxy-α-(3-chlorophenyl)acetamido]-3-(1-methyltetrazol-5-ylthiomethyl)-Δ³-O-2-isocephem-4-carboxylic acid |
| D-2-trifluoromethylmandelic acid | 7β-[D-α-hydroxy-α-(2-trifluoromethylphenyl)acetamido]-3-(1-methyltetrazol-5-ylthiomethyl)-Δ³-O-2-isocephem-4-carboxylic acid |
| D-3-nitromandelic acid | 7β-[D-α-hydroxy-α-(3-nitrophenyl)acetamido]-3-(1-methyltetrazol-5-ylthiomethyl)-Δ³-O-2-isocephem-4-carboxylic acid |
| D-p-hydroxymandelic acid | 7β-[D-α-hydroxy-α-(p-hydroxyphenyl)acetamido]-3-(1-methyltetrazol-5-ylthiomethyl)-Δ³-O-2-isocephem-4-carboxylic acid |
| D-3-chloro-4-hydroxymandelic acid | 7β-[D-α-hydroxy-α-(3-chloro-4-hydroxyphenyl)acetamido]-3-(1-methyltetrazol-5-ylthiomethyl)-Δ³-O-2-isocephem-4-carboxylic acid |
| D-3,5-dichloro-4-hydroxymandelic acid | 7β-[D-α-hydroxy-α-(3,5-dichloro-4-hydroxyphenyl)acetamido]-3-(1-methyltetrazol-5-ylthiomethyl)-Δ³-O-2-isocephem-4-carboxylic acid |
| D-o-methylaminomandelic acid | 7β-[D-α-hydroxy-α-(o-methylaminophenyl)acetamido]-3-(1-methyltetrazol-5-ylthiomethyl)-Δ³-O-2-isocephem-4-carboxylic acid |
| D-p-methoxymandelic acid | 7β-[D-α-hydroxy-α-(p-methoxyphenyl)acetamido]-3-(1-methyltetrazol-5-ylthiomethyl)-Δ³-O-2-isocephem-4-carboxylic acid |
| D-m-methylthiomandelic acid | 7β-[D-α-hydroxy-α-(m-methylthiophenyl)acetamido]-3-(1-methyltetrazol-5-ylthiomethyl)-Δ³-O-2-isocephem-4-carboxylic acid |
| D-m-iodomandelic acid | 7β-[D-α-hydroxy-α-(m-iodophenyl)acetamido]-3-(1-methyltetrazol-5-ylthiomethyl)-Δ³-O-2-isocephem-4-carboxylic acid |
| 4-isoxazoleglycolic acid | 7β-[α-hydroxy-α-(4-isoxazolyl)-acetamido]-3-(1-methyltetrazol-5-ylthiomethyl)-Δ³-O-2-isocephem-4-carboxylic acid |
| 4-thiazoleglycolic acid | 7β-[α-hydroxy-α-(4-thiazolyl)-acetamido]-3-(1-methyltetrazol-5-ylthiomethyl)-Δ³-O-2-isocephem-4-carboxylic acid |
| 4-oxazoleglycolic acid | 7β-[α-hydroxy-α-(4-oxazolyl)-acetamido]-3-(1-methyltetrazol-5-ylthiomethyl)-Δ³-O-2-isocephem-4-carboxylic acid |
| 3-isothiazoleglycolic acid | 7β-[α-hydroxy-α-(3-isothiazolyl)-acetamido]-3-(1-methyltetrazol-5-ylthiomethyl)-Δ³-O-2-isocephem-3-O-2-iocephem-4-carboxylic acid |
| 1,2,3-triazole-4-glycolic acid | 7β-[α-hydroxy-α-(1,2,3-triazol-4-yl)acetamido]-3-(1-methyltetrazol-5-ylthiomethyl)-Δ³-O-2-isocephem-4-carboxylic acid |
| 5-isoxazoleglycolic acid | 7β-[α-hydroxy-α-(5-isoxazolyl)-acetamido]-3-(1-methyltetrazol-5-ylthiomethyl)-Δ³-O-2-isocephem-4-carboxylic acid |
| 1,2,4-triazole-3-glycolic acid | 7β-[α-hydroxy-α-(1,2,4-triazol-3-yl)acetamido]-3-(1-methyltetrazol-5-ylthiomethyl)-Δ³-O-2-isocephem-4-carboxylic acid |
| 2-thienylglycolic acid | 7β-[α-hydroxy-α-(2-thienyl)-acetamido]-3-(1-methyltetrazol-5-ylthiomethyl)-Δ³-O-2-isocephem-4-carboxylic acid |
| 3-thienylglycolic acid | 7β-[α-hydroxy-α-)3-thienyl)-acetamidpo]-3-(1-methyltetrazol-5-ylthiomethyl)-Δ³-O-2-isocephem-4-carboxylic acid |
| 1,4-cyclohexadien-1-yl-glycolic acid | 7β[α-hydroxy-α-(1,4-cyclohexadien-1-yl)acetamido]-3-(1-methyltetrazol-5-ylthiomethyl)-Δ³-O-2-isocephem-4-carboxylic acid |
| 1-cyclohexenylglycolic acid | 7β-[α-hydroxy-α-(1-cyclohexenyl)acetamido]-3-(1-methyltetrazol-5-ylthiomethyl)-Δ³-O-2-isocephem-4-carboxylic acid |
| 2-pyrrolylglycolic acid | 7β-[α-hydroxy-α-(2-pyrrolyl)-acetamido]-3-(1-methyltetrazol-5-ylthiomethyl)-Δ³-O-2-isocephem-4-carboxylic acid |
| 2-furylglycolic acid | 7β-[α-hydroxy-α-(2-furyl)-acetamido]-3-(1-methyltetrazol-5-ylthiomethyl)-Δ³-O-2-isocephem-4-carboxylic acid |
| 3-pyridylglycolic acid | 7β-[α-hydroxy-α-(3-pyridyl)-acetamido]-3-(1-methyltetrazol-5-ylthiomethyl)-Δ³-O-2-isocephem-4-carboxylic acid |

EXAMPLE 40

When benzyl 7β-amino-3-(1-methyltetrazol-5-ylthiomethyl)-Δ³-0-2-isocephem-4-carboxylate is acylated according to the general acylation procedures described above with the acylating agents listed below (suitably protectted if desired), there are produced the following compounds after removal of any protecting groups:

| Acylating Agent | Product |
|---|---|
| p-hydroxyphenylmalonic acid | 7β-[α-carboxy-α-(p-hydroxyphenyl)acetamido]-3-(1-methyltetrazol-5-ylthiomethyl)-Δ³-O-2-isocephem-4-carboxylic acid |
| 3-chloro-4-hydroxyphenylmalonic acid | 7β-[α-carboxy-α-(3-chloro-4-hydroxyphenyl)acetamido]-3-(1-methyltetrazol-5-ylthiomethyl)-Δ³-O-2-isocephem-4-carboxylic acid |
| 3,5-dichloro-4-hydroxyphenylmalonic acid | 7β-[α-carboxy-α-(3,5-dichloro-4-hydroxyphenyl)acetamido]-3-(1-methyltetrazol-5-ylthiomethyl)-Δ³-O-2-isocephem-4-carboxylic acid |
| o-chlorophenylmalonic acid | 7β-[α-carboxy-α-(o-chlorophenyl)acetamido]-3-(1-methyltetrazol-5-ylthiomethyl)-Δ³-O-2-isocephem-4-carboxylic acid |
| p-nitrophenylmalonic acid | 7β-[α-carboxy-α-(p-nitrophenyl)acetamido]-3-(1-methyltetrazol-5-ylthiomethyl)-Δ³-O-2-isocephem-4-carboxylic acid |

-continued

| Acylating Agent | Product |
|---|---|
| p-acetoxyphenylmalonic acid | 7β-[α-carboxy-α-(p-acetoxyphenyl)acetamido]-3-(1-methyltetrazol-5-ylthiomethyl)-Δ³-O-2-isocephem-4-carboxylic acid |
| p-methoxyphenylmalonic acid | 7β-[α-carboxy-α-(p-methoxyphenyl)acetamido]-3-(1-methyltetrazol-5-ylthiomethyl)-Δ³-O-2-isocephem-4-carboxylic acid |
| p-methylthiophenylmalonic acid | 7β-[α-carboxy-α-(p-methylthiophenyl)acetamido]-3-(1-methyltetrazol-5-ylthiomethyl)-Δ³-O-2-isocephem-4-carboxylic acid |
| p-cyanophenylmalonic acid | 7β-[α-carboxy-α-(p-cyanophenyl)-acetamido]-3-(1-methyltetrazol-5-ylthiomethyl)-Δ³-O-2-isocephem-4-carboxylic acid |
| m-isopropylphenylmalonic acid | 7β-[α-carboxy-α-(m-isopropylphenyl)acetamido]-3-(1-methyltetrazol-5-ylthiomethyl)-Δ³-O-2-isocephem-4-carboxylic acid |
| o-aminomethylphenyl-malonic acid | 7β-[α-carboxy-α-(o-aminomethylphenyl)acetamido]-3-(1-methyltetrazol-5-ylthiomethyl)-Δ³-O-2-isocephem-4-carboxylic acid |
| o-dimethylaminophenyl-malonic acid | 7β-[α-carboxy-α-(o-dimethylainophenyl)acetamido]-3-(1-methyltetrazol-5-ylthiomethyl)-Δ³-O-2-isocephem-4-carboxylic acid |
| 2-thienylmalonic acid | 7β-[-60-carboxy-α-(2-thienyl)-acetamido]-3-(1-methyltetrazol-5-ylthiomethyl)-Δ³-O-2-isocephem-4-carboxylic acid |
| 3-thienylmalonic acid | 7β-[α-carboxy-α-(3-thienyl)-acetamido]-3-(1-methyltetrazol-5-ylthiomethyl)-Δ³-O-2-isocephem-4-carboxylic acid |
| 1,4-cyclohexadienyl-malonic acid | 7β-[α-carboxy-α-(1,4-cyclohexadien-1-yl)acetamido]-3-(1-methyltetrazol-5-ylthiomethyl)-Δ³-O-2-isocephem-4-carboxylic acid |
| 1-cyclohexenylmalonic acid | 7β-[α-carboxy-α-(1-cyclohexenyl)acetamido]-3-(1-methyltetrazol-5-ylthiomethyl)-Δ³-O-2-isocephem-4-carboxylic acid |
| 2-furylmalonic acid | 7β-[α-carboxy-α-(2-furyl)-acetamido]-3-(1-methyltetrazol-5-ylthiomethyl)-Δ³-O-2-isocephem-4-carboxylic acid |
| 3-pyridylmalonic acid | 7β-[α-carboxy-α-(4-pyridyl)-acetamido]-3-(1-methyltetrazol-5-ythiomethyl)-Δ³-O-2-isocephem-4-carboxylic acid |

EXAMPLE 41

When 7β-amino-3-(1-methyltetrazol-5-ylthiomethyl)-Δ³-0-2-isocephem-4-carboxylic acid or an ester or salt thereof is acylated according to the general procedures of the preceeding examples with an acylating agent of the formula

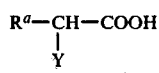

or a functional equivalent thereof, there are produced the compounds listed below

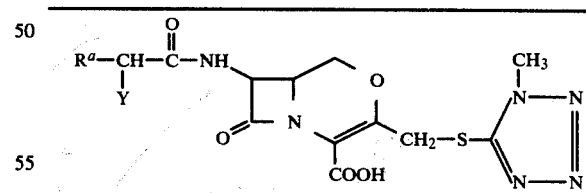

| $R^a$ | Y |
|---|---|
| phenyl | guanidino |
| 2-thienyl | guanidino |
| 3-thienyl | guanidino |
| 1,4-cyclohexadienyl | guanidino |
| 1-cyclohexenyl | guanidino |
| p-hydroxyphenyl | guanidino |
| 3-chloro-4-hydroxyphenyl | guamnidino |
| 3,5-dichloro-4-hydroxyphenyl | guanidino |
| phenyl | ureido |
| 2-thienyl | ureido |
| 3-thienyl | ureido |
| 1-cyclohexenyl | ureido |
| 1,4-cyclohexadienyl | ureido |

-continued

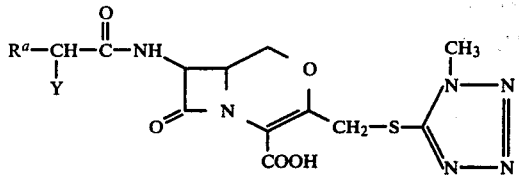

| Rᵃ | Y |
|---|---|
| p-hydroxyphenyl | ureido |
| 3,5-dichloro-4-hydroxyphenyl | ureido |
| o-aminomethylphenyl | ureido |
| p-methylphenyl | ureido |
| m-chlorophenyl | ureido |
| phenyl | thioureido |
| 2-thienyl | thioureido |
| 3-thienyl | thioureido |
| 1-cyclohexenyl | thioureido |
| 1,4-cyclohexadienyl | thioureido |
| p-hydroxyphenyl | thioureido |
| 3-chloro-4-hydroxyphenyl | thioureido |
| 3,5-dichloro-4-hydroxyphenyl | thioureido |
| o-aminomethylphenyl | methylthioureido |
| m-chlorophenyl | allylthioureido |
| phenyl | chloro |
| 2-thienyl | bromo |
| 3-thienyl | chloro |
| 1,4-cyclohexadienyl | methoxy |
| 1-cyclohexenyl | ethoxy |
| phenyl | phenyl |
| 2-thienyl | methoxy |
| 3-thienyl | ethoxy |
| p-hydroxyphenyl | iodo |
| p-trifluoromethylphenyl | methoxy |
| 3,4-dichlorophenyl | methoxy |
| phenyl | acetoxy |
| 2-thienyl | acetoxy |
| 2-furyl | acetoxy |
| p-nitrophenyl | acetoxy |
| p-methoxyphenyl | acetoxy |
| phenyl | propionyloxy |
| phenyl | cyano |
| phenyl | SO₃H |
| phenyl | azido |
| phenyl | methylsulfonyl |
| phenyl | 5-indanyloxycarbonyl |
| p-hydroxyphenyl | 5-indanyloxycarbonyl |
| 3-chloro-4-hydroxyphenyl | 5-indanyloxycarbonyl |
| 3,5-dichloro-4-hydroxyphenyl | 5-indanyloxycarbonyl |

EXAMPLE 42

Preparation of 7β-[α-(2-Aminomethyl-1,4-cyclohexadienyl)-acetamido]-3-(1-methyltetrazol-5-ylthiomethyl)-Δ³-0-2-isocephem-4-carboxylic acid

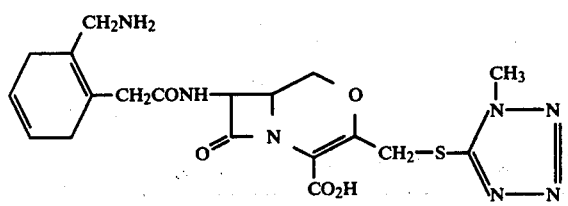

A. α-(2-Aminomethyl-1,4-cyclohexadienyl)acetic acid

A solution of 16.5 g. (0.1 mole) of o-aminomethylphenylacetic acid in 1.5 l of liquid ammonia (which had been treated with 50 mg. of Li to remove a trace of moisture) was slowly diluted with 500 ml. of dry t-BuOH. To the solution was added in small portions 3.4 g. (0.5g. atom) of Li over a period of 4 hours and the mixture was stirred for 16 hours at room temperature removing the liquid ammonia in a hood and finally evaporated to dryness below 40° C. The residue was dissolved in 500 ml. of water and the solution was chromatographed on a column of IR-120 (H⁺, 700 ml.) resin and eluted with 1% NH₄OH solution. Ninhydrin positive fractions of the eluate were combined and evaporated to dryness. The residue was washed with four 50 ml. portions of hot acetone and recrystallized from 500 ml. of ethanol water (1:1) to give 11.2 g. (67%) of α-(2-aminomethyl-1,4-cyclohexadienyl)acetic acid as colorless needles. M.p. 183° C.

IR: $\nu^{maxnuj}$ 1630, 1520, 1380, 1356 cm⁻¹. NMR: $\delta D_2O + K_2CO_3$ 2.72

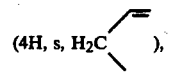

3.01 (2H, s, C$\underline{H}_2$CO), 3.29 (2H, s, C$\underline{H}_2$-N), 5.78

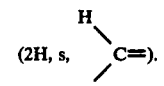

Anal. Calcd. for $C_9H_{13}NO_2$: C, 64.65; H, 7.84; n, 8.38. Found: C, 64.77; H, 8.06; N, 8.44.

B. α-[2-(t-Butoxycarbonylaminomethyl)-1,4-cyclohexadienyl]-acetic acid

To a stirred solution of 8.0 g. (0.048 mole) of α-(2-aminomethyl-1,4-cyclohexadienyl)acetic acid and 3.8 g. (0.096 mole) of NaOH in 150 ml. of water was added a solution of 10.3 g. (0.072 mole) of t-butoxycarbonylazide in 80 ml. of THF and the mixture was stirred for 18 hours at room temperature. The THF was removed under reduced pressure and the residual solution was washed with ether (2×100 ml.), acidified with 6 N HCl and extracted with ether (3×100 ml.). The combined extracts were washed with water (2×100 ml.) and a saturated NaCl solution (100 ml.), dried with Na₂SO₄ and evaporated to dryness. The oily residue was triturated with n-hexane to give 10.5 g. (82%) of colorless powder melting at 113° C.

IR: $\nu^{maxnuj}$ 3370, 1715, 1640, 1530, 1280, 1160 cm⁻¹.

NMR: $\delta_{ppm}^{CDCl_3}$ 1.45 (9H, s, t-Bu-H), 2.73

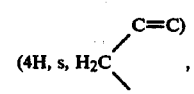

3.16 (2H, s, C$\underline{H}_2$CO), 3.76 (2H, d, 6Hz, C$\underline{H}_2$N) 4.90 (1H, m, N$\underline{H}$), 5.66

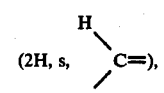

10.6 (1H, br-s, COO$\underline{H}$).

Anal. Calcd. for $C_{14}H_{21}NO_4$: C, 62.90; H, 7.92; N, 5.24. Found: C, 63.13; H, 8.21; N, 5.26.

C.

7β-[α-t-Butoxycarbonylaminomethyl-1,4-cyclohexadienyl)-acetamido]-3-(1-methyltetrazol-5-ylthiomethyl)-Δ³-0-2-isocephem-4-carboxylic acid To a stirred solution of equimolar amounts of α-[2-(t-butoxycarbonylaminomethyl)-1,4-cyclohexadienyl)acetic acid and 2,4-dinitrophenyl in ethyl acetate is added an equimolar amount of N,N'-dicyclohexylcarbodiimide. The reaction mixture is stirred at room temperature for 3 hours. The separated dicyclohexylurea is filtered off. The filtrate is evaporated to dryness to give the activated ester which is dissolved in tetrahydrofuran. To this solution is added a solution of 7β-amino-3-(1-methyltetrazol-5-ylthiomethyl)-Δ³-0-2-isocephem-4-carboxylic acid and triethylamine in approximately a 1:2 molar proportion, respectively, relative to the α[2-(t-butoxycarbonylaminomethyl)-1,4-cyclohexadienyl]acetic acid. The mixture is stirred at room temperature for several hours and concentrated in vacuo. The concentrate is washed with ether, acidified with dilute mineral acid and estracted with ethyl acetate. The extracts are washed with water and saturated NaCl solution and dried to give the title product.

D.

7β-[α-(2-Aminomethyl-1,4-cyclohexadienyl)acetamido]-3-(1-methyltetrazol-5-ylthiomethyl)-Δ³-0-2-isocephem-4-carboxylic acid A solution of 7β-[α-(2-t-butoxycarbonylaminomethyl-1,4-cyclohexadienyl)acetamido]-3-(1-methyltetrazol-5-ylthiomethyl)-Δ³-0-2-isocephem-4-carboxylic acid in trifluoroacetic acid is stirred at 0° C. for one hour. To the solution is added dry ether until a precipitate forms. The precipitate is collected by filtration, suspended in water and adjusted to pH6 to give the title product.

EXAMPLE 43

7β-[α-(2-Aminomethyl-1-cyclohexenyl)acetamido]-3-(1-methyltetrazol-5-ylthiomethyl)-Δ³-0-2-isocephem-4-carboxylic acid

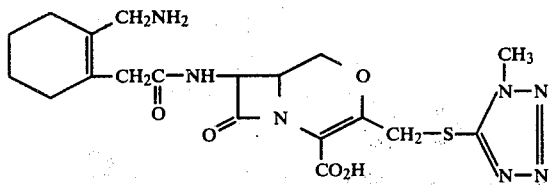

A.

[2-(N-t-Butoxycarbonylaminomethyl)-1-cyclohexen-1-yl]-acetic acid

A solution of α-[2-(t-butoxycarbonylaminomethyl)-1,4-cyclohexadienyl]-acetic acid (1.33 g., 5 mmoles) in 3% ammonium hydroxide (10 ml.) was hydrogenated at 40 psi with palladium on charcoal (10%, 0.2 g.). A theoretical amount of hydrogen was taken up in 3 hours. The catalyst was removed and the filtrate was acidified to pH 2 with dil. HCl and extracted with ethyl acetate (2×50 ml.). The combined extracts were washed with water (20 ml.), dried with Na₂SO₄ and evaporated under reduced pressure to afford an oil (1.34 g.) which solidified on standing for several days. Recrystallization from n-hexane - ethyl acetate gave 1.2 g. title product as colorless prisms melting at 118°–119° C.

IR: $\nu_{max}^{nujol}$ 3450, 1730, 1660, 1510 cm⁻¹.

NMR: $\delta_{ppm}^{CDCl_3}$ 1.58 (9H, s, t-butyl-H), 1.50–1.90 (4H, m, —CH₂—), 1.90–2.20 (4H, m, allylic methylene-H), 3.18 (2H, s, CH₂—CO), 3.78 (2H, d, 6 Hz, CH₂—N), 5.00 (1H, br-s, NH), 8.98 (1H, br-s, COOH).

Anal. Calcd. for C₁₄H₂₃NO₄: C, 62.43; H, 8.61; N, 5.20 Found: C, 62.12; H, 8.77; N, 5.37.

B.

7β-[α-(2-t-Butoxycarbonylaminomethyl-1-cyclohexenyl)acetamido]-3-(1-methyltetrazol-5-ylthiomethyl)-Δ³-0-2-isocephem-4-carboxylic acid To a stirred solution of equimolar amounts of [2-(N-t-butoxycarbonylaminomethyl)-1-cyclohexen-1-yl]acetic acid and 2,4-dinitrophenol in ethyl acetate is added an equimolar amount of N,N'-dicyclohexylcarbodiimide. The reaction mixture is stirred for 1 hour at room temperature and the precipitated dicyclohexylurea is filtered off. The filtrate is cooled to 5° C. and poured into a cold solution of 7β-amino-3-(1-methyltetrazol-5-ylthiomethyl)-Δ³-0-2-isocephem-4-carboxylic acid and excess triethylamine in 50% aqueous THF. The mixture is stirred overnight at room temperature and washed with ether. The aqueous layer is acidified with dilute HCl to precipitate the title product.

C.

7β-[α-Aminomethyl-1-cyclohexenyl)acetamido]-3-(1-methyltetrazol-5-ylthiomethyl)-Δ³-0-2-isocephem-4-carboxylic acid A solution of 7β-[α-(2-t-butoxycarbonylaminomethyl-1-cyclohexenyl)acetamido]-3-(1-methyltetrazol-5-ylthiomethyl)-Δ³-0-2-isocephem-4-carboxylic acid in trifluoroacetic acid is stirred at 0° C. for 1.5 hours. The mixture is diluted with ether to separate the trifluoroacetate salt which is dissolved in water and neutralized to give the title product.

EXAMPLE 44

When the p-nitrobenzyl 7β-amino-3-(1-methyltetrazol-5-ylthiomethyl)-Δ³-0-2-isocephem-4-carboxylate of Example 15 is replaced by an equimolar weight of p-nitrobenzyl preceeding 7β-amino-3-(1,2,3-triazol-5-ylthiomethyl)-Δ³-0-2-isocephem-4-carboxylate, p-nitrobenzyl 7β-amino-3-(1-carboxymethyl-1,2,3,4-tetrazol-5-ylthiomethyl)-Δ³-0-2-isocephem-4-carboxylate and p-nitrobenzyl 7β-amino-3-(1-carboxyethyl-1,2,3,4-tetrazol-5-ylthiomethyl)-Δ³-0-2-isocephem-4-carboxylate, respectively, there are produced after catalytic hydrogenation as in the procedure of Example 20 7β-(2-thienylacetamido)-3-(1,2,3-triazol-5-ylthiomethyl)-Δ³-0-2-isocephem-4-carboxylic acid, 7β-(2-thienylacetamido)-3-(1-carboxymethyl-1,2,3,4-tetrazol-5-ylthiomethyl)-Δ³-0-2-isocephem-4-carboxylic acid and 7β-(2-thienylacetamido)-3-(1-carboxyethyl-1,2,3,4-tetrazol-5-ylthiomethyl)-Δ³-0-2-isocephem-4-carboxylic acid, respectively.

EXAMPLE 45

When the 7β-amino-3-(1-methyltetrazol-5-ylthiomethyl)-Δ³-0-2-isocephem-4-carboxylic acid (or ester or salt thereof) in the procedures of Examples 17, 18, 24 and 25–43 is replaced by an equimolar amount of 7β-amino-3-(1,2,3-triazol-5-ylthiomethyl)-Δ³-0-2-isocephem-4-carboxylic acid, 7β-amino-3-(2-methyl-1,3,4-thiadiazol-5-ylthiomethyl)-Δ³-0-2-isocephem-4carboxy-

103 lic acid, 7β-amino-3-(2-methyl-1,3,4-oxadiazol-5-ylthiomethyl)-Δ³-0-2-isocephem-4-carboxylic acid, 7β-amino-3-(1-carboxymethyltetrazol-5-ylthiomethyl)-Δ³-0-2-isocephem-4-carboxylic acid or 7β-amino-3-(1-carboxyethyltetrazol-5-ylthiomethyl)-Δ³-0-2-isocephem-4-carboxylic acid (or an ester or salt thereof, any reactive functional groups other than 7- amino group being suitably protected if necessary), respectively, there are produced (after any necessary deblocking of functional protecting groups) the corresponding 7β-acylamino carboxylic acids of each of the above-named nuclei.

EXAMPLE 46

When the 7β-amino-3-(1-methyltetrazol-5-ylthiomethyl)-Δ³-0-2-isocephem-4-carboxylic acid (or ester or salt thereof) in the procedures of Examples 15, 17, 24, and 25–43 is replaced by an equimolar amount of each of the 7β-amino esters of Example 10 (any reactive functional groups other than the 7-amino group being suitably protected if necessary), there are produced (after any necessary de-blocking of functional protecting groups and the p-nitrobenzyl ester group) the corresponding 7β-acylamino carboxylic acids of each of the 7β-amino esters.

EXAMPLE 47

When the α-amino products of Examples 24 and 37–38, 45 and 46 are reacted with acetone according to the procedure of U.S. Pat. No. 3,303,193, there are obtained the corresponding 0-2-isocephem derivatives of the formula

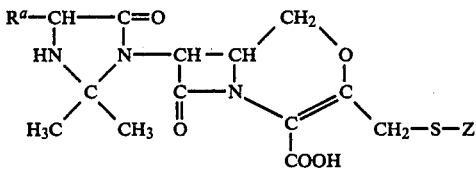

where $R^a$ is as defined in the above-mentioned examples and Z represents the appropriate alkyl, aryl, aralkyl or heterocyclic group of the selected nucleus, or pharmaceutically acceptable salts thereof.

EXAMPLE 48

When the α-amino products of Examples 24, 37–38, 45 or 46 are reacted with dicyanogen or cyanogen bromide or cyanogen chloride according to the procedure disclosed in U.S. Pat. No. 3,796,709, the corresponding α-cyanamino products are obtained.

EXAMPLE 49

When the α-amino products of Examples 24, 37–38, 45 or 46 are reacted with a triethylamine —SO₃ complex according to the procedure of U.S. Pat. No. 3,381,001, the corresponding α-sulfoamino products are obtained.

EXAMPLE 50

When the α-amino products of Examples 24, 37–38, 45 or 46 are reacted with 1-methyl-1-nitrosobiuret or a 1-methyl-5-(lower)alkyl-1-nitrosobiuret according to the procedure of U.S. Pat. No. 3,483,188, there are produced the compounds of the general formula

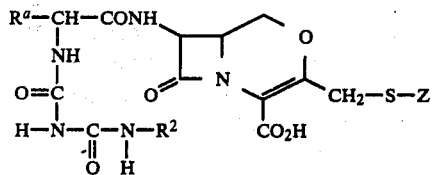

where $R^2$ is hydrogen or (lower)alkyl, Z represents the appropriate alkyl, aryl, aralkyl or heterocyclic group of the selected nucleus and $R^a$ is as defined in the above-mentioned examples.

EXAMPLE 51

When the 7-amino intermediates in the acylation procedures of Examples 15, 16, 17, 19, 24 and 25–46 are replaced by the corresponding pivaloyloxymethyl, acetoxymethyl, methoxymethyl, acetonyl and phenacyl esters, respectively, and the ester group of the 7-acylamido product is not removed, there are obtained the corresponding pivaloyloxymethyl, acetoxymethyl, methoxymethyl, acetonyl and phenacyl esters, respectively, of the 7-acylamido end-products.

EXAMPLE 52

7β-Phenoxyacetamido-3-(1-methyltetrazol-5-ylthiomethyl)-Δ³-0-2-isocephem-4-carboxylic acid (alternate process)

A mixture of benzyl 7β-phenoxyacetamido-3 -methylsulfonyloxymethyl-Δ³-0-2-isocephem-4-carboxylate (0.22 g., 0.43 mmole; prepared according to preparation 4 above), triethylamine (0.07 ml., 0.5 mmole) and 1-methyltetrazole thiol (0.05 g., 0.5 mmole) in methylene chloride (50 ml.) was stirred at room temperature for 16 hours, washed with 10% HCl (20 ml.) and brine (2×50 ml.), dried and concentrated to give a semi-solid (0.24 g.) which was purified by column chromatography to afford 0.15 g. of pure benzyl 7β-phenoxyacetamido-3-(1-methyltetrazol-5-ylthiomethyl)-Δ³-0-2-isocephem-4-carboxylate as a white semi-solid. The product was shown by IR and NMR to be identical with the product of Example 18.

Anal. Calc'd. for $C_{25}H_{24}N_6O_6S$: C, 55.97; H, 4.50; N, 15.66. Found: C, 55.89; H, 4.55; N, 15.34.

The benzyl ester is subjected to catalytic hydrogenation following the procedure of Example 23 to give the title product.

We claim:

1. A compound having the formula

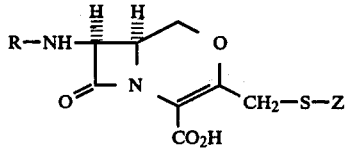

wherein R is an acyl group of the formula

wherein $R^a$ is (a) aryl selected from the group consisting of phenyl, 2-thienyl, 3-thienyl, furyl, 4-isoxazolyl, pyridyl, tetrazolyl, sydnone-3 or -4, imidazolyl, naphthoyl, quinoxalinyl, triazolyl, isothiazolyl, thiadiazolyl, thiazolyl, oxazolyl, oxadiazolyl, pyrazolyl, furazan, pyrazinyl, pyrimidinyl, pyridazinyl and triazinyl; (b) substituted aryl in which the aryl groups defined above under (a) are substituted by one or more chloro, bromo, iodo, fluoro, nitro, amino, cyano, (lower)alkanoyloxy, (lower)alkanoyl, (lower)alkoxyamino, (lower)alkoxy, (lower)alkyl, (lower)alkylamino, hydroxy, guanidino, (lower)alkylthio, carboxy, phenyl, halophenyl, trifluoromethyl, di(lower)alkylamino, sulfamyl, (lower)alkanoylamino, phenyl(lower)alkylamido, cycloalkylamino, allylamido, morpholinocarbonyl, pyrrolidinocarbonyl, piperidinocarbonyl, tetrahydropyridino, furfurylamido or N-alkyl-N-anilino radicals; (c) $C_3$-$C_{12}$ cycloalkyl; (d) substituted $C_3$-$C_{12}$ cycloalkyl in which the substituents are one or more chloro, bromo, fluoro, iodo, nitro, trifluoromethyl, $C_1$-$C_4$ alkyl, $C_1$-$C_4$ alkylamino, $C_1$-$C_2$ alkoxy or amino radicals; (e) $C_3$-$C_{12}$ cycloalkenyl, said cycloalkenyl group having 1 or 2 double bonds; or (f) substituted $C_3$-$C_{12}$ cycloalkenyl, said cycloalkenyl group having 1 to 2 double bonds and being substituted by one or more chloro, bromo, fluoro, iodo, nitro, trifluoromethyl, $C_1$-$C_4$ alkyl, $C_1$-$C_4$ alkylamino, $C_1$-$C_2$ alkoxy or amino radicals; and n is an integer from 1–4;

 (ii)

wherein n is an integer from 1–7, the alkyl portion of said acyl group being straight or branched and optionally interrupted by an oxygen or sulfur atom;

 (iii)

wherein n is an integer from 2–7, the alkenyl portion of said acyl group being straight or branched and optionally interrupted by an oxygen or sulfur atom;

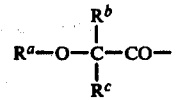 (iv)

wherein $R^a$ is as defined above under (i) and in addition may be benzyl, $C_1$-$C_6$ alkyl or (lower)alkoxy carbonyl and $R^b$ and $R^c$ which may be the same or different each represent hydrogen, phenyl, benzyl, phenethyl or $C_1$-$C_6$ alkyl;

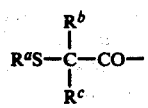 (v)

wherein $R^a$ is as defined above under (i) and in addition may be benzyl or $C_1$-$C_6$ alkyl and $R^b$ and $R^c$ are as defined under (iv);

 (vi)

wherein $R^a$ is as defined under (i) and in addition may be benzyl; X is oxygen or sulfur; and m is an integer of 2–5;

 (vii)

wherein $R^a$ is as defined under (i);

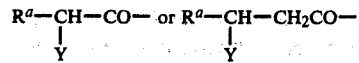 (viii)

wherein $R^a$ is as defined under (i) and Y is hydrazino, guanidino, ureido; substituted ureido of the formula

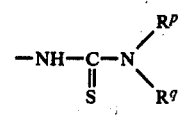

in which $R^p$ is hydrogen or $C_1$-$C_8$ alkyl and $R^q$ is hydrogen, $C_1$-$C_8$ alkyl, $C_2$-$C_8$ alkenyl, phenyl, benzoyl, $C_1$-$C_8$ alkoxy-$C_1$-$C_8$ alkyl or (carbo-$C_1$-$C_8$ alkoxy)C-1-$C_8$ alkyl; allophanamido; 3-guanyl-1-ureido; 3-(2-furoyl)ureido; 3-(benzoyl)ureido; cyano; cyanamino; azido; amino; a group obtained by reacting the amino group Y with acetone, formaldehyde, acetaldehyde; butyraldehyde, acetylacetone, methyl acetoacetate, benzaldehyde, salicylaldehyde, methyl ethyl ketone or ethyl acetoacetate; hydroxy; (lower)alkoxy; carboxy; 5-indanyloxycarbonyl; triazolyl; tetrazolyl; halogeno; formyloxy; (lower)alkanoyloxy; sulfo; or sulfoamino;

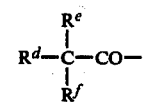 (ix)

wherein $R^d$, $R^e$ and $R^f$ which may be the same or different may each represent $C_1$-$C_6$ alkyl, phenyl or phenyl substituted by one or more chloro, bromo, iodo, fluoro, trifluoromethyl, nitro, amino, cyano, (lower)alkanoyloxy, (lower)alkanoyl, (lower)alkoxyamino, (lower)alkoxy, (lower)alkyl, (lower)alkylamino, hydroxy, (lower)alkylthio, carboxy, di(lower)alkylamino or sulfamyl radicals;

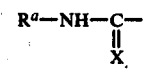 (x)

wherein $R^a$ is as defined under (i) and in addition may be hydrogen, $C_1$-$C_6$ alkyl, halogen-substituted $C_1$-$C_6$ alkyl, phenethyl, phenoxymethyl, benzyl or $R^a$—CO— and X is oxygen or sulfur;

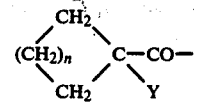 (xi)

wherein Y is as defined under (viii) and n is an integer of 1–4;

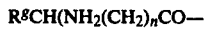 (xii)

wherein n is an integer of 1–10, or

wherein m is 0 or an integer from 1–10, and n is 0, 1 or 2; $R^g$ is hydrogen, (lower)alkyl, phenyl, benzyl or carboxy and Ar is p-phenylene or 1,4-naphthylene;

 (xiii)

wherein $R^h$ is 2-thienyl; 3-thienyl; α-naphthyl; 2-phenanthryl or a mono-, di- or tri-substituted phenyl group, the substituents being chloro, bromo, iodo, fluoro, amino, di(lower)-alkylamino, (lower)alkyl, (lower)alkoxy, nitro or (lower)-alkanoylamino;

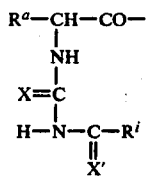   (xiv)

wherein $R^a$ is as defined under (i); X is oxygen or sulfur; X' is oxygen or imino; and $R^i$ is (lower)alkyl, cycloalkyl having 4, 5, 6 or 7 carbon atoms, monohalo (lower)alkyl, dichloromethyl, trichloromethyl, (lower)alkenyl of 2–6 carbon atoms,

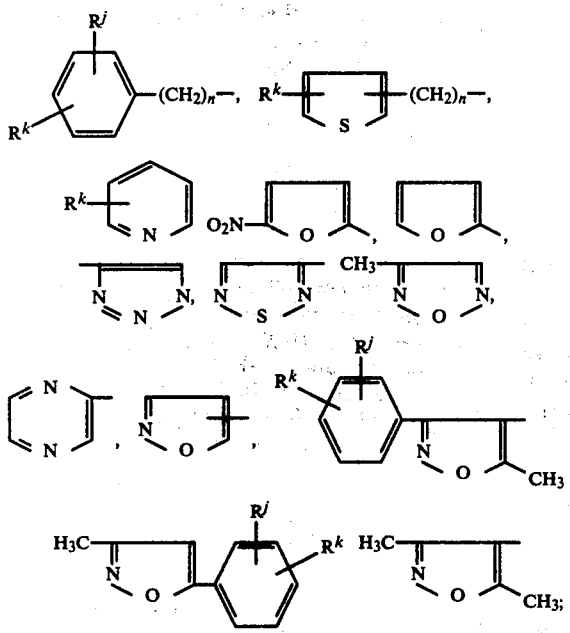

n is an integer from 0 to 3 inclusive and each of $R^k$ and $R^j$ is hydrogen, nitro, di(lower)alkylamino, (lower)alkanoylamino, (lower)alkanoyloxy, $C_1$–$C_6$ alkyl, $C_1$–$C_6$ alkoxy, sulfamyl, chloro, iodo, bromo, fluoro, or trifluoromethyl;

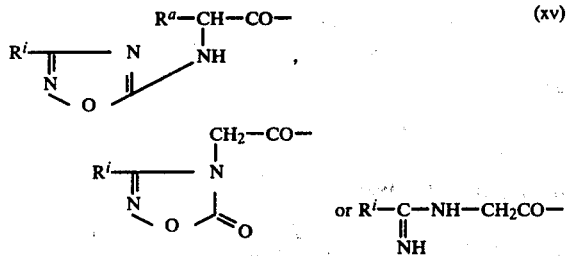   (xv)

wherein $R^a$ is as defined under (i) and $R^i$ is as defined under (xiv); or

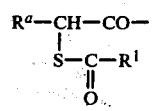   (xvi)

wherein $R^a$ is as defined under (i) and $R^1$ is (lower)alkyl, cycloalkyl of 3–12 carbon atoms, phenyl, a monocyclic heterocyclic radical having 5 or 6 atoms exclusive of hydrogen which are C, S, N or O, no more than 2 atoms being other than C, or a substituted monocyclic heterocyclic radical as defined above having one or more halo, (lower)alkyl, (lower)alkoxy or phenyl substituents, Z represents a member selected from the group consisting of $C_1$–$C_6$ alkyl optionally substituted by one or more hydroxy, halo, amino, nitro, di($C_1$–$C_4$ alkyl)amino, carboxy, sulfo or cyano substituents and a radical of the formula aryl-$(ALK)_m$- in which aryl is phenyl or naphthyl, ALK represents a straight or branched chain alkylene radical and m is 0 or an integer from 1 to 4, said radical being optionally substituted by one or more substituents selected from the group consisting of halo, $C_1$–$C_4$ alkyl, $C_1$–$C_4$ alkoxy, cyano, carboxyl, amino, nitro, $C_3$–$C_4$ cycloalkyl, $C_2$–$C_4$ alkenyl, trifluoromethyl, hydroxy, hydroxymethyl, $C_1$–$C_4$-alkylthio, $C_1$–$C_4$ alkylamino, di($C_1$–$C_4$ alkyl)amino, mercapto, phenyl, benzyl, alkoxyalkyl of up to 4 carbons and —$(CH_2)_n$COOH in which n is an integer of 1 to 4 and R″ is hydrogen or an easily cleavable ester selected from the group consisting of benzhydryl, benzyl, p-nitrobenzyl, p-methoxybenzyl, trichloroethyl, trimethylsilyl, phenacyl, acetonyl, (lower)alkyl, triphenylmethyl, methoxymethyl, indanyl, phthalidyl, pivaloyloxymethyl and acetoxymethyl, or a pharmaceutically acceptable salt thereof.

2. A compound of claim 1 wherein R is an acyl group of the formula $$R^a C_n H_{2n} CO—$$

in which $R^a$ is phenyl; phenyl substituted by one or more chloro, bromo, iodo, fluoro, nitro, amino, (lower)alkyl, guanidino, (lower)alkylthio, cyano, (lower)alkoxy, sulfamyl, (lower)alkylamino, hydroxy, acetoxy or trifluoromethyl radicals; 2-thienyl; 3-thienyl; tetrazolyl; sydnone-3- or sydnone-4; furyl; isothiazolyl; thiadiazolyl optionally substituted with phenyl; oxadiazolyl optionally substituted with phenyl; thiazolyl; imidazolyl; triazolyl; oxazolyl; pyridyl; furazan optionally substituted at the 3-position with methoxy; 4-isoxazolyl optionally substituted at the 5-position with methyl and at the 3-position with phenyl or halophenyl; 1,4-cyclohexadienyl; 1-cyclohexenyl or 1-aminocyclohexyl.

3. A compound of claim 2 wherein n is 1.

4. A compound of claim 1 wherein R is an acyl group of the formula

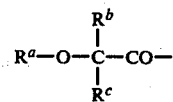

in which $R^a$ is phenyl and $R^b$ and $R^c$ which may be the same or different each represent hydrogen, phenyl, benzyl, phenethyl or $C_1$–$C_6$ alkyl.

5. A compound of claim 1 wherein R is an acyl group of the formula

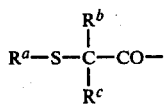

in which $R^a$ is phenyl; phenyl substituted with one or more chloro, bromo, iodo, fluoro, nitro, amino, (lower-)alkyl, (lower)alkylthio, cyano, (lower)alkoxy, (lower-)alkylamino, hydroxy, acetoxy or trifluoromethyl radicals; 3-pyridyl or 4-pyridyl; and $R^b$ and $R^c$ are hydrogen.

6. A compound of claim 1 wherein R is an acyl group of the formula

in which $R^a$ is phenyl; phenyl substituted with one or more chloro, bromo, iodo, fluoro, nitro, amino, (lower-)alkyl, (lower)alkylthio, cyano, (lower)alkoxy, (lower-)alkylamino, di(lower)alkylamino, hydroxy, acetoxy or trifluoromethyl radicals; 2-ethoxynaphthoyl; 3-phenyl-5-methylisoxazol-4-yl; 3-o-chlorophenyl-5-methylisoxazol-4-yl; 3-(2,6-dichlorophenyl)-5-methylisoxazol-4-yl; or 1-aminocyclohexyl.

7. A compound of claim 1 wherein R is an acyl group of the formula

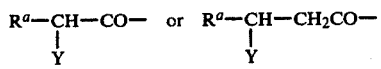

in which $R^a$ is (a) aryl selected from the group consisting of phenyl, 2-thienyl, 3-thienyl, furyl, 4-isoxazolyl, pyridyl, tetrazolyl, sydnone-3 or -4, imidazolyl, naphthoyl, quinoxalinyl, triazolyl, isothiazolyl, thiadiazolyl, thiazolyl, oxazolyl, oxadiazolyl, pyrazolyl, furazan, pyrazinyl, pyrimidinyl, pyridazinyl and triazinyl; (b) substituted aryl in which the aryl groups defined above under (a) are substituted by one or more chloro, bromo, iodo, fluoro, nitro, amino, cyano, (lower)alkanoyloxy, (lower)alkanoyl, (lower)alkoxyamino, (lower)alkoxy, (lower)alkyl, (lower)alkylamino, hydroxy, guanidino, (lower)alkylthio, carboxy, phenyl, halophenyl, trifluoromethyl, di(lower)alkylamino, sulfamyl, (lower)alkanoylamino, phenyl(lower)alkylamido, cycloalkylamino, allylamido, morpholinocarbonyl, pyrrolidinocarbonyl, piperidinocarbonyl, tetrahydropyridino, furfurylamido or N-alkyl-N-anilino radicals; (c) $C_3$-$C_{12}$ cycloalkyl; (d) substituted $C_3$-$C_{12}$ cycloalkyl in which the substitutents are one or more chloro, bromo, fluoro, iodo, nitro, trifluoromethyl, $C_1$-$C_4$ alkyl, $C_1$-$C_4$ alkylamino, $C_1$-$C_2$ alkoxy or amino radicals; (e) $C_3$-$C_{12}$ cycloalkenyl, said cycloalkenyl group having 1 or 2 double bonds; or (f) substituted $C_3$-$C_{12}$ cycloalkenyl, said cycloalkenyl group having 1 or 2 double bonds and being substituted by one or more chloro, bromo, fluoro, iodo, nitro, trifluoromethyl, $C_1$-$C_4$ alkyl, $C_1$-$C_4$ alkylamino, $C_1$-$C_2$ alkoxy or amino radicals; and Y is hydrazino, guanidino, ureido; substituted ureido or the formula

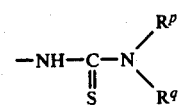

in which $R^p$ is hydrogen or $C_1$-$C_8$ alkyl and $R^q$ is hydrogen, $C_1$-$C_8$ alkyl, $C_2$-$C_8$ alkenyl, phenyl, benzoyl, $C_1$-$C_8$ alkoxy-$C_1$-$C_8$ alkyl or (carbo-$C_1$-$C_8$ alkyl; allophanamido; 3-guanyl-1-ureido; 3-(2-furoyl)ureido; 3-(benzoyl)ureido; cyano; cyanamino; azido; amino; a group obtained by reacting the amino group Y with acetone, formaldehyde, acetaldehyde, butyraldehyde, acetylacetone, methyl acetoacetate, benzaldehyde, salicylaldehyde, methyl ethyl ketone or ethyl acetoacetate; hydroxy; (lower)alkoxy; carboxy; 5-indanyloxycarbonyl; triazolyl; tetrazolyl; halogeno; formyloxy; (lower)alkanoyloxy; sulfo; or sulfoamino.

8. A compound of claim 1 wherein R is an acyl group of the formula

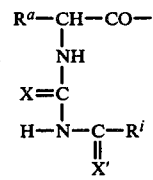

in which $R^a$ is 2-thienyl; 3-thienyl; phenyl; or phenyl substituted by one or more nitro, di(lower)alkylamino, (lower)alkanoylamino, amino, hydroxy, (lower)alkanoyloxy, $C_1$-$C_6$ alkyl, $C_1$-$C_6$ alkoxy, sulfamyl, chloro, bromo, iodo, fluoro, or trifluoromethyl radicals; X is oxygen; X' is oxygen or imino; and $R^i$ is (lower)alkyl, phenyl, 2-thienyl, 3-thienyl, 2-furyl or 5-nitro-2-furyl.

9. A compound of claim 8 wherein $R^a$ is phenyl, p-hydroxyphenyl, 2-thienyl or 3-thienyl; X' is oxygen; and $R^i$ is phenyl or 2-furyl.

10. A compound of claim 1 wherein R is an acyl group of the formula

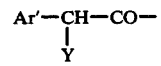

in which Ar' is a radical of the formula

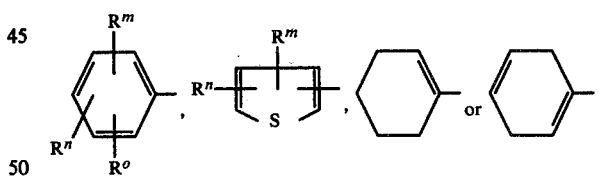

in which $R^m$, $R^n$ and $R^o$ are alike or different and each is hydrogen, hydroxy, (lower)alkyl, cyano, (lower)alkoxy, chloro, bromo, iodo, fluoro, trifluoromethyl, nitro, amino, (lower)-alkylamino, di(lower)alkylamino, (lower)alkanoyl, (lower)-alkanoyloxy and Y is amino or a group obtained by reacting the amino group with acetaldehyde, formaldehyde or acetone; fluoro; chloro bromo; iodo; hydroxy; (lower)alkanoyloxy; carboxy; guanidino; 3-guanyl-1-ureido; 3-(2-furoyl)ureido; 3-benzoylureido; sulfo; sulfoamino, ureido; thioureido; (lower)alkoxy; cyano, cyanamino; or indanyloxycarbonyl.

11. A compound of claim 10 wherein Ar' is phenyl, p-hydroxyphenyl, 4-hydroxy-3,5-dichlorophenyl, 3-chloro-4-hydroxyphenyl, o-, m- or p-aminomethylphenyl, 2-thienyl, 3-thienyl, 1-cyclohexenyl or 1,4-cyclohexadienyl and Y is amino, hydroxy or carboxy.

12. A compound of claim 1 wherein R is an acyl group of the formula
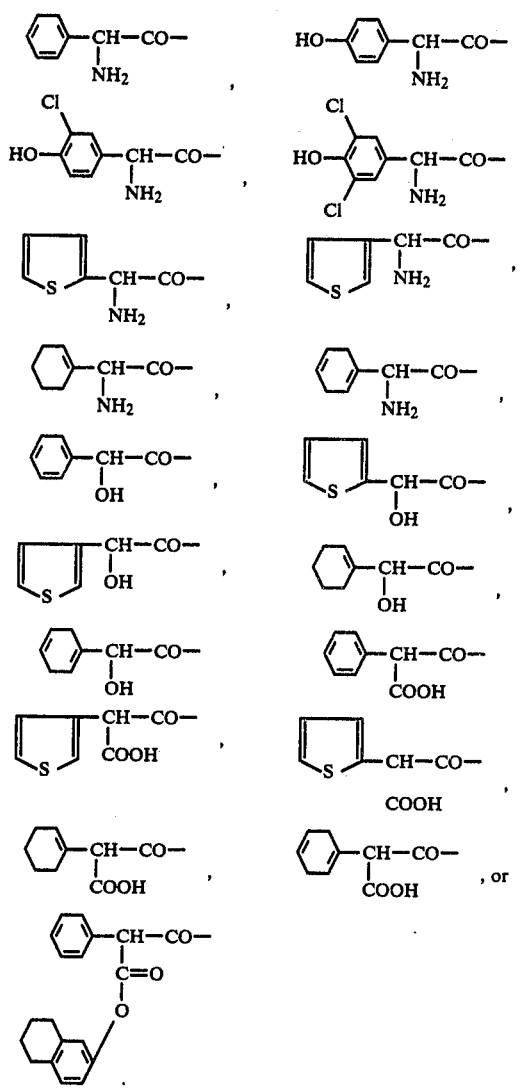
13. A compound of claim 1 wherein R is an acyl group of the formula
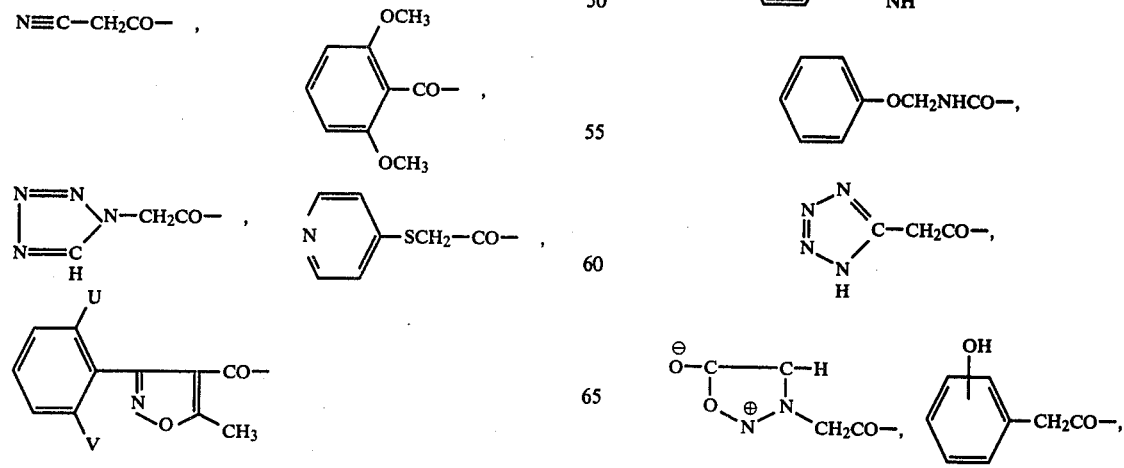
wherein U and V are alike or different and each is hydrogen, chloro or fluoro;
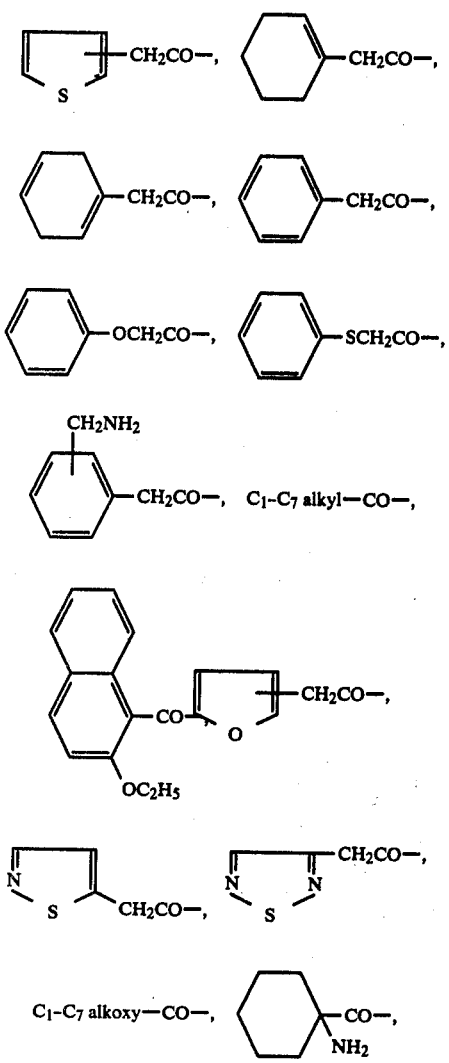

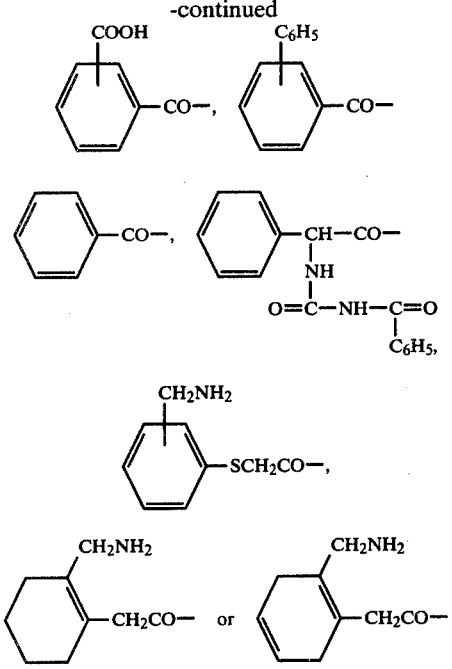

14. An acid of claim 1 wherein R″ is hydrogen and R is α-carboxyphenyl, cyanoacetyl, α-amino-α-(p-hydroxyphenyl)-acetyl, α-amino-α-(3-chloro-4-hydrox- yphenyl)acetyl, α-amino-α-(3,5-dichloro-4-hydroxyphenyl)acetyl, α-amino-α-(2-thienyl)-acetyl, α-amino-α-(3-thienyl)acetyl, α-amino-α-(1-cyclohexenyl)-acetyl, α-amino-α-(1,4-cyclohexadienyl)acetyl, α-hydroxyacetyl, α-hydroxy-α-(2-thienyl)acetyl, α-hydroxy-α-(3-thienyl)acetyl, α-hydroxy-α-(1-cyclohexenyl)acetyl, α-hydroxy-α-(1,4-cyclohexadienyl)acetyl, α-carboxy-α-(2-thienyl)acetyl, α-carboxy-α-(3-thienyl)acetyl, α-carboxy-α-(1-cyclohexenyl)acetyl, α-carboxy-α-(1,4-cyclohexadienyl)acetyl, α-indanyloxycarbonyl-α-phenylacetyl, 1-(1H)-tetrazolyl, 4-pyridylthioacetyl, 2-thienylacetyl, 3-thienylacetyl, 1-cyclohexenylacetyl, 1,4-cyclohexadienylacetyl, o-aminomethylphenylacetyl, 1-aminocyclohexylcarbonyl, 2,6-dimethoxybenzoyl, sydnone-acetyl or α-azidophenylacetyl, or a parmaceutically acceptable salt thereof.

15. The D-isomer of an acid of claim 1 wherein R″ is hydrogen and R is α-amino-α-(p-hydroxyphenyl)acetyl, α-amino-α-(3-chloro-4-hydroxyphenyl)acetyl, α-amino-α-(3,5-dichloro-4-hydroxyphenyl)-acetyl, α-amino-α-(2-thienyl)acetyl, α-amino-α-(3-thienyl)acetyl, α-amino-α-(1-cyclohexenyl)acetyl, α-amino-α-(1,4-cyclohexadienyl)acetyl, α-hydroxyacetyl, α-hydroxy-α-(2-thienyl)-acetyl, α-hydroxy-α-hydroxy-α-(3-thienyl)acetyl, α-hydroxy-α-(1-cyclohexenyl)acetyl or α-hydroxy-α-(1,4-cyclohexadienyl)acetyl, or a pharmaceutically acceptable salt thereof.

* * * * *

UNITED STATES PATENT AND TRADEMARK OFFICE
CERTIFICATE OF CORRECTION

PATENT NO. : 4,171,438
DATED : October 16, 1979
INVENTOR(S) : Donald E. Horning et al.

It is certified that error appears in the above–identified patent and that said Letters Patent are hereby corrected as shown below:

In Claim 7, column 110, line 3, the term "(carbo-$C_1$-$C_8$ alkyl" should read --(carbo-$C_1$-$C_8$ alkoxy)$C_1$-$C_8$ alkyl--.

In Claim 13, column 112, lines 28-35, the structural formula should read:

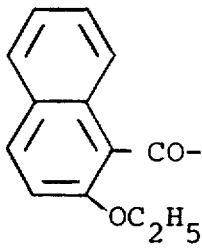 , 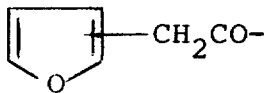 ,

Signed and Sealed this

Twelfth Day of February 1980

[SEAL]

Attest:

SIDNEY A. DIAMOND

Attesting Officer  Commissioner of Patents and Trademarks